(12) United States Patent
Ghislieri et al.

(10) Patent No.: US 12,264,355 B2
(45) Date of Patent: Apr. 1, 2025

(54) PROCESS FOR PRODUCING AMMONIUM (METH-) ACRYLATE

(71) Applicant: BASF SE, Ludwigshafen am Rhein (DE)

(72) Inventors: Diego Ghislieri, Ludwigshafen (DE); Peter Oedman, Saint Joseph, MO (US); Tobias Joachim Zimmermann, Ludwigshafen (DE); Anna-Corina Schmidt, Trostberg (DE)

(73) Assignee: BASF SE, Ludwigshafen am Rhein (DE)

(*) Notice: Subject to any disclaimer, the term of this patent is extended or adjusted under 35 U.S.C. 154(b) by 697 days.

(21) Appl. No.: 17/286,372

(22) PCT Filed: Oct. 17, 2019

(86) PCT No.: PCT/EP2019/078158
§ 371 (c)(1),
(2) Date: Apr. 16, 2021

(87) PCT Pub. No.: WO2020/079120
PCT Pub. Date: Apr. 23, 2020

(65) Prior Publication Data
US 2021/0348200 A1 Nov. 11, 2021

(30) Foreign Application Priority Data
Oct. 18, 2018 (EP) .................................. 18201231

(51) Int. Cl.
C12P 7/40 (2006.01)
C12M 1/00 (2006.01)
C12M 1/02 (2006.01)
C12N 9/78 (2006.01)

(52) U.S. Cl.
CPC ............. C12P 7/40 (2013.01); C12M 29/18 (2013.01); C12M 41/18 (2013.01); C12N 9/78 (2013.01); *C12Y 305/05001* (2013.01)

(58) Field of Classification Search
CPC ........... C12P 7/40; C12P 13/00; C12M 21/18; C12M 41/18; C12M 29/18; C12N 9/78; C12Y 305/05001
See application file for complete search history.

(56) References Cited

U.S. PATENT DOCUMENTS

| 6,162,624 A | 12/2000 | Symes et al. |
| 6,361,981 B1 | 3/2002 | Symes et al. |
| 6,670,158 B2 | 12/2003 | Dicosimo et al. |
| 8,409,854 B2 * | 4/2013 | Erhardt ................. C12M 29/04 435/304.2 |
| 2004/0175809 A1 | 9/2004 | Peterson et al. |
| 2009/0311759 A1 | 12/2009 | Abe et al. |
| 2021/0179758 A1 | 6/2021 | Sprafke et al. |

FOREIGN PATENT DOCUMENTS

| EA | 202091019 A1 | 9/2020 |
| EA | 202091021 A1 | 9/2020 |
| JP | 2007-002033 A | 1/2007 |
| JP | 4476822 B2 | 6/2010 |
| WO | 97/21817 A1 | 6/1997 |
| WO | 2005/054456 A1 | 6/2005 |
| WO | 2005/054489 A1 | 6/2005 |
| WO | 2010/133527 A2 | 11/2010 |
| WO | 2012/069478 A1 | 5/2012 |
| WO | 2015/024865 A1 | 2/2015 |
| WO | 2015/086468 A1 | 6/2015 |
| WO | 2015/158517 A1 | 10/2015 |
| WO | 2016/050817 A1 | 4/2016 |
| WO | 2016/131940 A1 | 8/2016 |
| WO | 2016/131941 A1 | 8/2016 |
| WO | 2019/081003 A1 | 5/2019 |
| WO | 2019/081004 A1 | 5/2019 |
| WO | 2019/081008 A1 | 5/2019 |
| WO | 2019/081318 A1 | 5/2019 |
| WO | 2019/081319 A1 | 5/2019 |
| WO | 2019/081320 A1 | 5/2019 |
| WO | 2019/081321 A1 | 5/2019 |
| WO | 2019/081323 A1 | 5/2019 |
| WO | 2019/081327 A1 | 5/2019 |
| WO | 2019/081330 A1 | 5/2019 |
| WO | 2019/081331 A1 | 5/2019 |

OTHER PUBLICATIONS

European Search Report for EP Patent Application No. 18201231.0, Issued on Apr. 3, 2019, 3 pages.
International Preliminary Report on Patentability received for PCT Patent Application No. PCT/EP2019/078158, mailed on Apr. 29, 2021, 13 pages.

(Continued)

*Primary Examiner* — Sean C. Barron
(74) *Attorney, Agent, or Firm* — Faegre Drinker Biddle & Reath LLP

(57) ABSTRACT

The present invention relates to a process for preparing ammonium (meth-) acrylate, aqueous ammonium (meth-) acrylate solutions obtainable by such process, and (meth-) acrylic acid homopolymers or copolymers obtainable by polymerizing such ammonium (meth-) acrylate. The invention furthermore relates to a modular, relocatable bioconversion unit for manufacturing aqueous ammonium (meth-) acrylate solutions.

9 Claims, 2 Drawing Sheets

Specification includes a Sequence Listing.

(56) References Cited

OTHER PUBLICATIONS

International Search Report and Written Opinion received for PCT Patent Application No. PCT/EP2019/078158, mailed on Feb. 4, 2020, 16 pages.

Tevatia et al: "Kinetic modeling of photoautotrophic growth and neutral lipid accumulation in terms of ammonium concentration in Chlamydomonas reinhardtii", Bioresource Technology, vol. 119, 2012, pp. 419-424.

Meledina T.V. et al., Equipment-specific methodological base of experiments in the field of food biotechnology of products from vegetable raw materials, Tutorial, St. Petersburg,ITMO University, 2017, p. 27.

* cited by examiner

SEQUENCE LISTING

<160> NUMBER OF SEQ ID NOS: 75

<210> SEQ ID NO 1
<211> LENGTH: 1011
<212> TYPE: DNA
<213> ORGANISM: Unknown
<220> FEATURE:
<223> OTHER INFORMATION: Unknown prokaryotic organism

<400> SEQUENCE: 1
atgaaagaag cgattaaagt ggcgtgcgtg caggcggcgc cgatttatat ggatctggaa    60

```
gcgaccgtgg ataaaaccat tgaactgatg gaagaagcgg cgcgcaacaa cgcgcgcctg      120
attgcgtttc cggaaacctg gattccgggc tatccgtggt ttctgtggct ggatagcccg      180
gcgtgggcga tgcagtttgt gcgccagtat catgaaaaca gcctggaact ggatggcccg      240
caggcgaaac gcattagcga tgcggcgaaa cgcctgggca ttatggtgac cctgggcatg      300
agcgaacgcg tgggcggcac cctgtatatt agccagtggt ttattggcga taacggcgat      360
accattggcg cgcgccgcaa actgaaaccg acctttgtgg aacgcaccct gtttggcgaa      420
ggcgatggca gcagcctggc ggtgtttgaa accagcgtgg gccgcctggg cggcctgtgc      480
tgctgggaac atctgcagcc gctgaccaaa tatgcgctgt atgcgcagaa cgaagaaatt      540
cattgcgcgg cgtggccgag ctttagcctg tatccgaacg cggcgaaagc gctgggcccg      600
gatgtgaacg tggcggcgag ccgcatttat gcggtggaag ccagtgcttt gtgctggcg      660 agctgcgcgc tggtgagcca gagcatgatt gatatgctgt gcaccgatga tgaaaaacat      720
gcgctgctgc tggcgggcgg cggccatagc cgcattattg cccggatgg cggcgatctg      780 gtggcgccgc tggcggaaaa cgaagaaggc attctgtatg cgaacctgga tccgggcgtg      840
cgcattctgg cgaaaatggc ggcggatccg gcgggccatt atagccgccc ggatattacc      900
cgcctgctga ttgatcgcag cccgaaactg ccggtggtgg aaattgaagg cgatctgcgc      960
ccgtatgcgc tgggcaaagc gagcgaaacc ggcgcgcagc tggaagaaat t            1011
```

```
<210> SEQ ID NO 2
<211> LENGTH: 337
<212> TYPE: PRT
<213> ORGANISM: Unknown
<220> FEATURE:
<223> OTHER INFORMATION: Unknown prokaryotic organism

<400> SEQUENCE: 2
```

```
Met Lys Glu Ala Ile Lys Val Ala Cys Val Gln Ala Ala Pro Ile Tyr
1               5                   10                  15

Met Asp Leu Glu Ala Thr Val Asp Lys Thr Ile Glu Leu Met Glu Glu
            20                  25                  30

Ala Ala Arg Asn Asn Ala Arg Leu Ile Ala Phe Pro Glu Thr Trp Ile
        35                  40                  45

Pro Gly Tyr Pro Trp Phe Leu Trp Leu Asp Ser Pro Ala Trp Ala Met
    50                  55                  60

Gln Phe Val Arg Gln Tyr His Glu Asn Ser Leu Glu Leu Asp Gly Pro
65                  70                  75                  80

Gln Ala Lys Arg Ile Ser Asp Ala Ala Lys Arg Leu Gly Ile Met Val
                85                  90                  95

Thr Leu Gly Met Ser Glu Arg Val Gly Gly Thr Leu Tyr Ile Ser Gln
            100                 105                 110

Trp Phe Ile Gly Asp Asn Gly Asp Thr Ile Gly Ala Arg Arg Lys Leu
        115                 120                 125

Lys Pro Thr Phe Val Glu Arg Thr Leu Phe Gly Glu Gly Asp Gly Ser
    130                 135                 140

Ser Leu Ala Val Phe Glu Thr Ser Val Gly Arg Leu Gly Gly Leu Cys
145                 150                 155                 160

Cys Trp Glu His Leu Gln Pro Leu Thr Lys Tyr Ala Leu Tyr Ala Gln
                165                 170                 175

Asn Glu Glu Ile His Cys Ala Ala Trp Pro Ser Phe Ser Leu Tyr Pro
            180                 185                 190
```

Asn Ala Ala Lys Ala Leu Gly Pro Asp Val Asn Val Ala Ser Arg
        195                 200                 205

Ile Tyr Ala Val Glu Gly Gln Cys Phe Val Leu Ala Ser Cys Ala Leu
    210                 215                 220

Val Ser Gln Ser Met Ile Asp Met Leu Cys Thr Asp Glu Lys His
225                 230                 235                 240

Ala Leu Leu Leu Ala Gly Gly His Ser Arg Ile Ile Gly Pro Asp
                245                 250                 255

Gly Gly Asp Leu Val Ala Pro Leu Ala Glu Asn Glu Glu Gly Ile Leu
            260                 265                 270

Tyr Ala Asn Leu Asp Pro Gly Val Arg Ile Leu Ala Lys Met Ala Ala
        275                 280                 285

Asp Pro Ala Gly His Tyr Ser Arg Pro Asp Ile Thr Arg Leu Leu Ile
    290                 295                 300

Asp Arg Ser Pro Lys Leu Pro Val Val Glu Ile Glu Gly Asp Leu Arg
305                 310                 315                 320

Pro Tyr Ala Leu Gly Lys Ala Ser Glu Thr Gly Ala Gln Leu Glu Glu
                325                 330                 335

Ile

<210> SEQ ID NO 3
<211> LENGTH: 942
<212> TYPE: DNA
<213> ORGANISM: Unknown
<220> FEATURE:
<223> OTHER INFORMATION: Unknown prokaryotic organism

<400> SEQUENCE: 3

| | | | | | |
|---|---|---|---|---|---|
| atgggtgaat | tcggtgaagt | taccctgggt | gttgctcagg | ctgctccggt | ttacttcgac | 60 |
| cgtgaagctt | ctaccgaaaa | agctcgtggt | ctgatccgtg | aagctggtga | aaaaggtgtt | 120 |
| gacctgctgg | ctttcggtga | aacctggctg | accggttacc | gtactggaa | agacgctccg | 180 |
| tggtctcgtg | aatacaacga | cctgcgtgct | cgttacgttg | ctaacggtgt | tatgatcccg | 240 |
| ggtccggaaa | ccgacgctct | gtgccaggct | gctgctgaag | ctggtgttga | cgttgctatc | 300 |
| ggtgttgttg | aactggaacc | gggttctctg | tcttctgttt | actgcaccct | gctgttcatc | 360 |
| tctcgtgaag | gtgaaatcct | gggtcgtcac | cgtaaactga | aaccgaccga | ctctgaacgt | 420 |
| cgttactggt | ctgaaggtga | cgctaccggt | ctgcgtgttt | acgaacgtcc | gtacggtcgt | 480 |
| ctgtctggtc | tgaactgctg | gaacacctg | atgatgctgc | cgggttacgc | tctggctgct | 540 |
| cagggtaccc | agttccacgt | tgctgcttgg | ccgaacatgg | cttcttctgc | ttctgaactg | 600 |
| ctgtctcgtg | cttacgctta | ccaggctggt | tgctacgttc | tgtgcgctgg | tggtctgggt | 660 |
| ccggctccgg | gtgaactgcc | ggacggtatc | gctgctgaat | ctctggacca | cctgaccggt | 720 |
| gaatcttgca | tcatcgaccc | gtggggtaaa | gttatcgctg | gtccggtttc | ttgcgaagaa | 780 |
| accctgatca | ccgctcgtgt | ttctaccgct | tctatctacc | gtcgtaaatc | tctgaccgac | 840 |
| gttggtggtc | actactctcg | tccggacgtt | ttccgtttcg | aagttgaccg | ttctgaacgt | 900 |
| ccgcgtgttg | ttttccgtga | cggtgacgtt | gacgaccgtg | gt | | 942 |

<210> SEQ ID NO 4
<211> LENGTH: 314
<212> TYPE: PRT
<213> ORGANISM: Unknown
<220> FEATURE:
<223> OTHER INFORMATION: Unknown prokaryotic organism

<400> SEQUENCE: 4

| | | | | | | | | | | | | | | | |
|---|---|---|---|---|---|---|---|---|---|---|---|---|---|---|---|
| Met | Gly | Glu | Phe | Gly | Glu | Val | Thr | Leu | Gly | Val | Ala | Gln | Ala | Ala | Pro |
| 1 | | | | 5 | | | | | 10 | | | | | 15 | |

| | | | | | | | | | | | | | | | |
|---|---|---|---|---|---|---|---|---|---|---|---|---|---|---|---|
| Val | Tyr | Phe | Asp | Arg | Glu | Ala | Ser | Thr | Glu | Lys | Ala | Arg | Gly | Leu | Ile |
| | | | 20 | | | | | 25 | | | | | 30 | | |

| | | | | | | | | | | | | | | | |
|---|---|---|---|---|---|---|---|---|---|---|---|---|---|---|---|
| Arg | Glu | Ala | Gly | Glu | Lys | Gly | Val | Asp | Leu | Leu | Ala | Phe | Gly | Glu | Thr |
| | | | | 35 | | | | | 40 | | | | | 45 | |

| | | | | | | | | | | | | | | | |
|---|---|---|---|---|---|---|---|---|---|---|---|---|---|---|---|
| Trp | Leu | Thr | Gly | Tyr | Pro | Tyr | Trp | Lys | Asp | Ala | Pro | Trp | Ser | Arg | Glu |
| | 50 | | | | | 55 | | | | | 60 | | | | |

| | | | | | | | | | | | | | | | |
|---|---|---|---|---|---|---|---|---|---|---|---|---|---|---|---|
| Tyr | Asn | Asp | Leu | Arg | Ala | Arg | Tyr | Val | Ala | Asn | Gly | Val | Met | Ile | Pro |
| 65 | | | | | 70 | | | | | 75 | | | | | 80 |

| | | | | | | | | | | | | | | | |
|---|---|---|---|---|---|---|---|---|---|---|---|---|---|---|---|
| Gly | Pro | Glu | Thr | Asp | Ala | Leu | Cys | Gln | Ala | Ala | Glu | Ala | Gly | Val |
| | | | | 85 | | | | | 90 | | | | | 95 |

| | | | | | | | | | | | | | | | |
|---|---|---|---|---|---|---|---|---|---|---|---|---|---|---|---|
| Asp | Val | Ala | Ile | Gly | Val | Val | Glu | Leu | Glu | Pro | Gly | Ser | Leu | Ser | Ser |
| | | | | 100 | | | | | 105 | | | | | 110 | |

| | | | | | | | | | | | | | | | |
|---|---|---|---|---|---|---|---|---|---|---|---|---|---|---|---|
| Val | Tyr | Cys | Thr | Leu | Leu | Phe | Ile | Ser | Arg | Glu | Gly | Glu | Ile | Leu | Gly |
| | | | 115 | | | | | 120 | | | | | 125 | | |

| | | | | | | | | | | | | | | | |
|---|---|---|---|---|---|---|---|---|---|---|---|---|---|---|---|
| Arg | His | Arg | Lys | Leu | Lys | Pro | Thr | Asp | Ser | Glu | Arg | Arg | Tyr | Trp | Ser |
| 130 | | | | | 135 | | | | | 140 | | | | | |

| | | | | | | | | | | | | | | | |
|---|---|---|---|---|---|---|---|---|---|---|---|---|---|---|---|
| Glu | Gly | Asp | Ala | Thr | Gly | Leu | Arg | Val | Tyr | Glu | Arg | Pro | Tyr | Gly | Arg |
| 145 | | | | | 150 | | | | | 155 | | | | | 160 |

| | | | | | | | | | | | | | | | |
|---|---|---|---|---|---|---|---|---|---|---|---|---|---|---|---|
| Leu | Ser | Gly | Leu | Asn | Cys | Trp | Glu | His | Leu | Met | Met | Leu | Pro | Gly | Tyr |
| | | | | 165 | | | | | 170 | | | | | 175 | |

| | | | | | | | | | | | | | | | |
|---|---|---|---|---|---|---|---|---|---|---|---|---|---|---|---|
| Ala | Leu | Ala | Ala | Gln | Gly | Thr | Gln | Phe | His | Val | Ala | Ala | Trp | Pro | Asn |
| | | | 180 | | | | | 185 | | | | | 190 | | |

| | | | | | | | | | | | | | | | |
|---|---|---|---|---|---|---|---|---|---|---|---|---|---|---|---|
| Met | Ala | Ser | Ser | Ala | Ser | Glu | Leu | Leu | Ser | Arg | Ala | Tyr | Ala | Tyr | Gln |
| | | 195 | | | | | 200 | | | | | 205 | | | |

| | | | | | | | | | | | | | | | |
|---|---|---|---|---|---|---|---|---|---|---|---|---|---|---|---|
| Ala | Gly | Cys | Tyr | Val | Leu | Cys | Ala | Gly | Gly | Leu | Gly | Pro | Ala | Pro | Gly |
| | 210 | | | | | 215 | | | | | 220 | | | | |

| | | | | | | | | | | | | | | | |
|---|---|---|---|---|---|---|---|---|---|---|---|---|---|---|---|
| Glu | Leu | Pro | Asp | Gly | Ile | Ala | Ala | Glu | Ser | Leu | Asp | His | Leu | Thr | Gly |
| 225 | | | | | 230 | | | | | 235 | | | | | 240 |

| | | | | | | | | | | | | | | | |
|---|---|---|---|---|---|---|---|---|---|---|---|---|---|---|---|
| Glu | Ser | Cys | Ile | Ile | Asp | Pro | Trp | Gly | Lys | Val | Ile | Ala | Gly | Pro | Val |
| | | | | 245 | | | | | 250 | | | | | 255 | |

| | | | | | | | | | | | | | | | |
|---|---|---|---|---|---|---|---|---|---|---|---|---|---|---|---|
| Ser | Cys | Glu | Glu | Thr | Leu | Ile | Thr | Ala | Arg | Val | Ser | Thr | Ala | Ser | Ile |
| | | | 260 | | | | | 265 | | | | | 270 | | |

| | | | | | | | | | | | | | | | |
|---|---|---|---|---|---|---|---|---|---|---|---|---|---|---|---|
| Tyr | Arg | Arg | Lys | Ser | Leu | Thr | Asp | Val | Gly | His | Tyr | Ser | Arg | Pro |
| | | 275 | | | | | 280 | | | | | 285 | | | |

| | | | | | | | | | | | | | | | |
|---|---|---|---|---|---|---|---|---|---|---|---|---|---|---|---|
| Asp | Val | Phe | Arg | Phe | Glu | Val | Asp | Arg | Ser | Glu | Arg | Pro | Arg | Val | Val |
| | | 290 | | | | | 295 | | | | | 300 | | | |

| | | | | | | | |
|---|---|---|---|---|---|---|---|
| Phe | Arg | Asp | Gly | Asp | Val | Asp | Asp | Arg | Gly |
| 305 | | | | 310 | | | | | |

<210> SEQ ID NO 5
<211> LENGTH: 969
<212> TYPE: DNA
<213> ORGANISM: Flavihumibacter solisilvae

<400> SEQUENCE: 5

```
atgagccata gtaccaataa taacagcagc accgttgttc gtgcagcagc cgtgcagatt    60
agcccggttc tgtatagtcg cgaaggcacc acccagaaag tggtgaatac cattcgtgaa   120
ctgggtaaac agggcgtgca gtttgcagtg tttccggaaa cctttattcc gtattatccg   180
tattttagtt tcgttcagcc gccgtatatg caggcagaac agcatctgaa actgatggaa   240
gaagcagtga ccgttccgag tgccaccacc gatgcaattg gcgaagccgc ccgtgaagcc   300
```

```
ggtattgttg ttagtattgg cgtgaatgaa cgtgatggtg gtagtctgta taatacccag    360
ctgctgtttg atgccgatgg taccctgatt cagcgccgtc gcaaaattac cccgacctat    420
catgaacgca tggtttgggg tcagggcgat ggtagcggcc tgcgcgctgt ggatagtaaa    480
gcaggccgta ttggccagct ggcatgttgg gaacattata atccgctggc ccgttatgca    540
atgattgccg atggtgaaca gattcatgca gcaatgtatc cgggcagcag ctttggcgaa    600
ctgtttagcc agcagattga agttagtgtt cgtcagcatg ccctggaaag tgccgccttt    660
gttgttagta gcaccgcatg gctggatgcc gatcagcagg cccagattat gaaagatacc    720
ggcagcccga ttggtccgat tagcggtggt aattttaccg ccattattgc cccggatggt    780
accattattg gcgaaccgat tcgtagcggc gaaggctttg tgattgcaga tttggatttt    840
aatctgattg agaaacgcaa acgtctgatg gatctgaaag ccattataa tcgcccggaa    900 ctgctgagtc tgctgattga tcgcacccc  gccgaatatg ttcaggaagt gaataagagt    960
gttagcgaa                                                            969
```

<210> SEQ ID NO 6
<211> LENGTH: 323
<212> TYPE: PRT
<213> ORGANISM: Flavihumibacter solisilvae
<400> SEQUENCE: 6

```
Met Ser His Ser Thr Asn Asn Ser Ser Thr Val Val Arg Ala Ala
1               5                   10                  15

Ala Val Gln Ile Ser Pro Val Leu Tyr Ser Arg Glu Gly Thr Thr Gln
            20                  25                  30

Lys Val Val Asn Thr Ile Arg Glu Leu Gly Lys Gln Gly Val Gln Phe
        35                  40                  45

Ala Val Phe Pro Glu Thr Phe Ile Pro Tyr Tyr Pro Tyr Phe Ser Phe
    50                  55                  60

Val Gln Pro Pro Tyr Met Gln Ala Glu Gln His Leu Lys Leu Met Glu
65                  70                  75                  80

Glu Ala Val Thr Val Pro Ser Ala Thr Thr Asp Ala Ile Gly Glu Ala
                85                  90                  95

Ala Arg Glu Ala Gly Ile Val Val Ser Ile Gly Val Asn Glu Arg Asp
            100                 105                 110

Gly Gly Ser Leu Tyr Asn Thr Gln Leu Leu Phe Asp Ala Asp Gly Thr
        115                 120                 125

Leu Ile Gln Arg Arg Arg Lys Ile Thr Pro Thr Tyr His Glu Arg Met
    130                 135                 140

Val Trp Gly Gln Gly Asp Gly Ser Gly Leu Arg Ala Val Asp Ser Lys
145                 150                 155                 160

Ala Gly Arg Ile Gly Gln Leu Ala Cys Trp Glu His Tyr Asn Pro Leu
                165                 170                 175

Ala Arg Tyr Ala Met Ile Ala Asp Gly Glu Gln Ile His Ala Ala Met
            180                 185                 190

Tyr Pro Gly Ser Ser Phe Gly Glu Leu Phe Ser Gln Gln Ile Glu Val
        195                 200                 205

Ser Val Arg Gln His Ala Leu Glu Ser Ala Ala Phe Val Val Ser Ser
    210                 215                 220

Thr Ala Trp Leu Asp Ala Asp Gln Gln Ala Gln Ile Met Lys Asp Thr
225                 230                 235                 240

Gly Ser Pro Ile Gly Pro Ile Ser Gly Gly Asn Phe Thr Ala Ile Ile
```

245                 250                 255
Ala Pro Asp Gly Thr Ile Ile Gly Glu Pro Ile Arg Ser Gly Glu Gly
            260                 265                 270

Phe Val Ile Ala Asp Leu Asp Phe Asn Leu Ile Glu Lys Arg Lys Arg
            275                 280                 285

Leu Met Asp Leu Lys Gly His Tyr Asn Arg Pro Glu Leu Leu Ser Leu
            290                 295                 300

Leu Ile Asp Arg Thr Pro Ala Glu Tyr Val Gln Glu Val Asn Lys Ser
305                 310                 315                 320

Val Ser Glu

<210> SEQ ID NO 7
<211> LENGTH: 1107
<212> TYPE: DNA
<213> ORGANISM: Acidovorax facilis
<220> FEATURE:
<223> OTHER INFORMATION: Acidovorax facilis 72W

<400> SEQUENCE: 7

```
atggtttctt acaactctaa attcctggct gctaccgttc aggctgaacc ggtttggctg     60
gacgctgacg ctaccatcga caaatctatc ggtatcatcg aagaagctgc tcagaaaggt    120
gcttctctga tcgctttccc ggaagttttc atcccgggtt accgtactg gcttggctg     180
ggtgacgtta atactctct gtctttcacc ctctcgttacc acgaaaactc tctgaactg    240
ggtgacgacc gtatgcgtcg tctgcagctg gctgctcgtc gtaacaaaat cgctctggtt    300
atgggttact ctgaacgtga agctggttct cgttacctgt ctcaggtttt catcgacgaa    360
cgtggtgaaa tcgttgctaa ccgtcgtaaa ctgaaaccga cccacgttga acgtaccatc    420
tacggtgaag taacggtac cgacttcctg acccacgact cgctttcgg tcgtgttggt    480
ggtctgaact gctgggaaca cttccagccg ctgtctaaat tcatgatgta ctctctgggt    540
gaacaggttc acgttgcttc ttggccggct atgtctccgc tgcagccgga cgttttccag    600
ctgtctatcg aagctaacgc taccgttacc cgttcttacg ctatcgaagg tcagaccttc    660
gttctgtgct ctacccaggt tatcggtccg tctgctatcg aaaccttctg cctgaacgac    720
gaacagcgtg ctctgctgcc gcagggttgc ggttgggctc gtatctacgg tccggacggt    780
tctgaactgg ctaaaccgct ggctgaagac gctgaaggta tcctgtacgc tgaaatcgac    840
ctggaacaga tcctgctggc taaagctggt gctgacccgg ttggtcacta ctctcgtccg    900
gacgttctgt ctgttcagtt cgacccgcgt aaccacaccc cggttcaccg tatcggtatc    960
gacggtcgtc tggacgttaa cacccgttct cgtgttgaaa acttccgtct gcgtcaggct   1020
gctgaacagg aacgtcaggc ttctaaacgt ctgggtacca aactgttcga acagtctctg   1080
ctggctgaag aaccggttcc ggctaaa                                       1107
```

<210> SEQ ID NO 8
<211> LENGTH: 369
<212> TYPE: PRT
<213> ORGANISM: Acidovorax facilis
<220> FEATURE:
<223> OTHER INFORMATION: Acidovorax facilis 72W

<400> SEQUENCE: 8

Met Val Ser Tyr Asn Ser Lys Phe Leu Ala Ala Thr Val Gln Ala Glu
1               5                   10                  15

Pro Val Trp Leu Asp Ala Asp Ala Thr Ile Asp Lys Ser Ile Gly Ile
            20                  25                  30

Ile Glu Glu Ala Ala Gln Lys Gly Ala Ser Leu Ile Ala Phe Pro Glu
             35                   40                  45

Val Phe Ile Pro Gly Tyr Pro Tyr Trp Ala Trp Leu Gly Asp Val Lys
         50                  55                  60

Tyr Ser Leu Ser Phe Thr Ser Arg Tyr His Glu Asn Ser Leu Glu Leu
 65                  70                  75                  80

Gly Asp Asp Arg Met Arg Arg Leu Gln Leu Ala Ala Arg Arg Asn Lys
                 85                  90                  95

Ile Ala Leu Val Met Gly Tyr Ser Glu Arg Glu Ala Gly Ser Arg Tyr
            100                 105                 110

Leu Ser Gln Val Phe Ile Asp Glu Arg Gly Ile Val Ala Asn Arg
            115                 120                 125

Arg Lys Leu Lys Pro Thr His Val Glu Arg Thr Ile Tyr Gly Glu Gly
        130                 135                 140

Asn Gly Thr Asp Phe Leu Thr His Asp Phe Ala Phe Gly Arg Val Gly
145                 150                 155                 160

Gly Leu Asn Cys Trp Glu His Phe Gln Pro Leu Ser Lys Phe Met Met
                165                 170                 175

Tyr Ser Leu Gly Glu Gln Val His Val Ala Ser Trp Pro Ala Met Ser
            180                 185                 190

Pro Leu Gln Pro Asp Val Phe Gln Leu Ser Ile Glu Ala Asn Ala Thr
        195                 200                 205

Val Thr Arg Ser Tyr Ala Ile Glu Gly Gln Thr Phe Val Leu Cys Ser
    210                 215                 220

Thr Gln Val Ile Gly Pro Ser Ala Ile Glu Thr Phe Cys Leu Asn Asp
225                 230                 235                 240

Glu Gln Arg Ala Leu Leu Pro Gln Gly Cys Gly Trp Ala Arg Ile Tyr
                245                 250                 255

Gly Pro Asp Gly Ser Glu Leu Ala Lys Pro Leu Ala Glu Asp Ala Glu
            260                 265                 270

Gly Ile Leu Tyr Ala Glu Ile Asp Leu Glu Gln Ile Leu Leu Ala Lys
        275                 280                 285

Ala Gly Ala Asp Pro Val Gly His Tyr Ser Arg Pro Asp Val Leu Ser
    290                 295                 300

Val Gln Phe Asp Pro Arg Asn His Thr Pro Val His Arg Ile Gly Ile
305                 310                 315                 320

Asp Gly Arg Leu Asp Val Asn Thr Arg Ser Arg Val Glu Asn Phe Arg
                325                 330                 335

Leu Arg Gln Ala Ala Glu Gln Glu Arg Gln Ala Ser Lys Arg Leu Gly
            340                 345                 350

Thr Lys Leu Phe Glu Gln Ser Leu Leu Ala Glu Glu Pro Val Pro Ala
        355                 360                 365

Lys

<210> SEQ ID NO 9
<211> LENGTH: 975
<212> TYPE: DNA
<213> ORGANISM: Pseudomonas sp
<220> FEATURE:
<223> OTHER INFORMATION: Pseudomonas sp. RIT357

<400> SEQUENCE: 9
atgaccagca aacgtgaaaa aaccgtggcc attgtgcaga tgccggcagc actgctggat      60
cgcgccgaaa gtatgcgccg cgcagccgaa catattaaga aagcagccct gcaagaagca     120

```
cagctggtta ttttccgga aacctggctg agttgttatc cggcctgggt gtttggtatg      180
gccggttggg atgatgcaca ggcaaaaagc tggtatgcaa aactgctggc agatagtccg      240
gttattggtc agccggaaga tatgcatgat gatctggcag aactgcgtga agccgcccgc      300
gtgaatgccg tgaccgtggt tatgggcatg aatgaacgta gtcgtcatca tggtggtagc      360
ctgtataata gtctggttac cattggtccg gatggtgcaa ttctgaatgt tcatcgtaaa      420
ctgaccccga cccataccga acgtaccgtt tgggcaaatg gtgacgcagc aggtctgcgc      480
gtggttgata ccgtggttgg tcgtgtgggt ggcctggttt gctgggaaca ttggcatccg      540
ctggcccgcc aggccctgca tgctcaagat gaacagattc atgttgcagc ctggccggat      600
atgccggaaa tgcatcatgt ggccgcccgc agctatgcat ttgaaggtcg ttgttttgtt      660
ctgtgtgcag gccagtatct ggcagcaggc gatgtgccgg cagaactgct ggccgcatat      720
cgccgtggcg ttggtggtaa agccctggaa gaagatgttc tgtttaatgg tggtagtggc      780
gttattgcac cggatggtag ttgggtgacc gcaccgctgt ttggcgaacc gggtattatt      840
ctggccacca ttgatctggc ccagattgat gcccagcatc atgatctgga tgtggcaggc      900
cattatctgc gtccggatgt gtttgaactg agtattgatc gccgcgttcg caccggtctg      960
accctgcgtg atgca                                                      975
```

<210> SEQ ID NO 10
<211> LENGTH: 325
<212> TYPE: PRT
<213> ORGANISM: Pseudomonas sp.
<220> FEATURE:
<223> OTHER INFORMATION: Pseudomonas sp. RIT357

<400> SEQUENCE: 10

```
Met Thr Ser Lys Arg Glu Lys Thr Val Ala Ile Val Gln Met Pro Ala
1               5                   10                  15

Ala Leu Leu Asp Arg Ala Glu Ser Met Arg Arg Ala Ala Glu His Ile
            20                  25                  30

Lys Lys Ala Ala Leu Gln Glu Ala Gln Leu Val Ile Phe Pro Glu Thr
        35                  40                  45

Trp Leu Ser Cys Tyr Pro Ala Trp Val Phe Gly Met Ala Gly Trp Asp
    50                  55                  60

Asp Ala Gln Ala Lys Ser Trp Tyr Ala Lys Leu Leu Ala Asp Ser Pro
65                  70                  75                  80

Val Ile Gly Gln Pro Glu Asp Met His Asp Asp Leu Ala Glu Leu Arg
                85                  90                  95

Glu Ala Ala Arg Val Asn Ala Val Thr Val Val Met Gly Met Asn Glu
            100                 105                 110

Arg Ser Arg His His Gly Gly Ser Leu Tyr Asn Ser Leu Val Thr Ile
        115                 120                 125

Gly Pro Asp Gly Ala Ile Leu Asn Val His Arg Lys Leu Thr Pro Thr
    130                 135                 140

His Thr Glu Arg Thr Val Trp Ala Asn Gly Asp Ala Ala Gly Leu Arg
145                 150                 155                 160

Val Val Asp Thr Val Val Gly Arg Val Gly Gly Leu Val Cys Trp Glu
                165                 170                 175

His Trp His Pro Leu Ala Arg Gln Ala Leu His Ala Gln Asp Glu Gln
            180                 185                 190

Ile His Val Ala Ala Trp Pro Asp Met Pro Glu Met His His Val Ala
        195                 200                 205
```

Ala Arg Ser Tyr Ala Phe Glu Gly Arg Cys Phe Val Leu Cys Ala Gly
    210                 215                 220

Gln Tyr Leu Ala Ala Gly Asp Val Pro Ala Glu Leu Leu Ala Ala Tyr
225                 230                 235                 240

Arg Arg Gly Val Gly Lys Ala Leu Glu Glu Asp Val Leu Phe Asn
                245                 250                 255

Gly Gly Ser Gly Val Ile Ala Pro Asp Gly Ser Trp Val Thr Ala Pro
                260                 265                 270

Leu Phe Gly Glu Pro Gly Ile Ile Leu Ala Thr Ile Asp Leu Ala Gln
        275                 280                 285

Ile Asp Ala Gln His His Asp Leu Asp Val Ala Gly His Tyr Leu Arg
    290                 295                 300

Pro Asp Val Phe Glu Leu Ser Ile Asp Arg Arg Val Arg Thr Gly Leu
305                 310                 315                 320

Thr Leu Arg Asp Ala
            325

<210> SEQ ID NO 11
<211> LENGTH: 924
<212> TYPE: DNA
<213> ORGANISM: Nocardia brasiliensis
<220> FEATURE:
<223> OTHER INFORMATION: Nocardia brasiliensis NBRC 14402

<400> SEQUENCE: 11

```
atgcgtattg cagcagcaca ggcccgtccg gcatggctgg accctaccgc tggtaccaaa    60
attgtggtgg attggctgac caaagcagcc gccgcaggtg cagaactggt tgcatttccg   120
gaaacctttc tgagtggcta tccgatttgg ctggcccgta ccggtggtgc acgctttgat   180
aatccggcac agaaagccgc atacgcttat tatctgggcg ccgcagtgac cctggatggt   240
ccgcagctgg ataccgtgcg caccgcagca ggtgacctgg cgttttctg ttatctgggc    300
attaccgaac gtgttcgtgg taccgtttat tgcaccctgg tggccattga tccggatcgt   360
ggcattgtgg gtgcccatcg caaactgatg ccgacccatg aagaacgtat ggtttgggcc   420
attggcgatg gtaatggcct gcgtgcccat gattttggcg ttttcgtgt tagtggcctg    480
agttgttggg aaaattggat gccgcaggcc cgccatgccc tgtatgcaga tggtaccacc   540
ctgcatgtta gcacctggcc gggtagtatt cgtaatacca agatattac ccgttttatt    600
gccctggaag tcgtgtgta gcctggcc gtgggtgccg tgctggatta tgcagatgtg      660
ccgaccgatt ttccgctgta tgaagaactg agcgcactgg ataaaccggc cggctatgat   720
ggcggcagtg ccgtggcagc cccggatggt acctggctgg ttgaaccggt ggtgggcacc   780
gaacgcctga ttctgcagga tttggacccct gccgaagtgg caaagaacg tcagaatttt    840
gatccgaccg ccattatgc acgcccggat attttagtg tgaccgtgaa tcgccatcgt    900
cgtaccccgg caacctttct ggat                                           924
```

<210> SEQ ID NO 12
<211> LENGTH: 308
<212> TYPE: PRT
<213> ORGANISM: Nocardia brasiliensis
<220> FEATURE:
<223> OTHER INFORMATION: Nocardia brasiliensis NBRC 14402

<400> SEQUENCE: 12

Met Arg Ile Ala Ala Ala Gln Ala Arg Pro Ala Trp Leu Asp Pro Thr
1               5                   10                  15

```
Ala Gly Thr Lys Ile Val Val Asp Trp Leu Thr Lys Ala Ala Ala Ala
            20                  25                  30

Gly Ala Glu Leu Val Ala Phe Pro Glu Thr Phe Leu Ser Gly Tyr Pro
        35                  40                  45

Ile Trp Leu Ala Arg Thr Gly Ala Arg Phe Asp Asn Pro Ala Gln
 50                  55                  60

Lys Ala Ala Tyr Ala Tyr Tyr Leu Gly Ala Val Thr Leu Asp Gly
 65                  70                  75                  80

Pro Gln Leu Asp Thr Val Arg Thr Ala Ala Gly Asp Leu Gly Val Phe
                85                  90                  95

Cys Tyr Leu Gly Ile Thr Glu Arg Val Arg Gly Thr Val Tyr Cys Thr
            100                 105                 110

Leu Val Ala Ile Asp Pro Asp Arg Gly Ile Val Gly Ala His Arg Lys
            115                 120                 125

Leu Met Pro Thr His Glu Glu Arg Met Val Trp Gly Ile Gly Asp Gly
            130                 135                 140

Asn Gly Leu Arg Ala His Asp Phe Gly Val Phe Arg Val Ser Gly Leu
145                 150                 155                 160

Ser Cys Trp Glu Asn Trp Met Pro Gln Ala Arg His Ala Leu Tyr Ala
            165                 170                 175

Asp Gly Thr Thr Leu His Val Ser Thr Trp Pro Gly Ser Ile Arg Asn
            180                 185                 190

Thr Lys Asp Ile Thr Arg Phe Ile Ala Leu Glu Gly Arg Val Tyr Ser
            195                 200                 205

Leu Ala Val Gly Ala Val Leu Asp Tyr Ala Asp Val Pro Thr Asp Phe
210                 215                 220

Pro Leu Tyr Glu Glu Leu Ser Ala Leu Asp Lys Pro Ala Gly Tyr Asp
225                 230                 235                 240

Gly Gly Ser Ala Val Ala Ala Pro Asp Gly Thr Trp Leu Val Glu Pro
            245                 250                 255

Val Val Gly Thr Glu Arg Leu Ile Leu Ala Asp Leu Asp Pro Ala Glu
            260                 265                 270

Val Ala Lys Glu Arg Gln Asn Phe Asp Pro Thr Gly His Tyr Ala Arg
            275                 280                 285

Pro Asp Ile Phe Ser Val Thr Val Asn Arg His Arg Arg Thr Pro Ala
290                 295                 300

Thr Phe Leu Asp
305

<210> SEQ ID NO 13
<211> LENGTH: 1059
<212> TYPE: DNA
<213> ORGANISM: Pseudomonas fluorescens

<400> SEQUENCE: 13
atgacggtgc ataaaaaaca gtacaaagta gccgcggtgc aggccgcccc tgcgttcctc      60
gacctggaag ctggcgtggc caaagccatc ggactgattg ctcaggcggc ggctgagggt     120
gcctcactgg tcgctttccc cgaagcgtgg ctgccggggt atccctggtg gatctggctg     180
gactccccgg ccggcggcat gcgcttcgtc cagcgcaact cgacaatgc tctggaggtc     240 ggcagcgaac ccttcgagcg gctctgcagg gctgcggcac agcacaaaat ctacgtcgta     300
ctgggcttca ctgaacgctc tggcggcacc ttgtatttgg ctcaggcgat cattgatgat     360
tgcggtcggg tagtcgccac acggcgtaag ctcaagccga ctcacgtgga gcgctcagtc     420
```

-continued

```
tacggagaag cgacggtag tgaccttgct gtgcatgaca ctaccttggg tcgcttaggt    480
gccttgtgct cgcggagca tatccagccg ctgtccaagt acgccatgta cgctcagcac    540
gaacaggtac atatcgcggc ctggcctagc ttttcggtat accgggggc tgcgtttcaa    600 ctgagcgccc aagccaataa tgccgcctcg caagtctacg cactggaagg tcagtgtttt    660
gtgctggcgc catgcgccac ggtgtccaaa gaaatgctcg acgaactgat tgattctccg    720
gccaaggctg agctgctgct ggaaggtggc ggcttcgcga tgatctacgg cccggatggc    780
gcaccgctgt gtacgccatt ggcggaaaca gaggagggca ttctctatgc ggatatcgac    840
ttgggggtga tcggggtggc caaagctgcc tacgacccgg ttggtcacta ttcacgccct    900
gatgtgctgc ggttgctggt caaccgggag ccaatgacgc gtgtgcatta tgttcagccg    960
cagtcgttac cggagacatc ggtgttggcg ttcggtgcgg gagcggatgc catcagaagt    1020
gaggagaacc cagaagagca aggcgacaag ggatcctga                          1059
```

<210> SEQ ID NO 14
<211> LENGTH: 352
<212> TYPE: PRT
<213> ORGANISM: Pseudomonas fluorescens

<400> SEQUENCE: 14

```
Met Thr Val His Lys Lys Gln Tyr Lys Val Ala Ala Val Gln Ala Ala
1               5                   10                  15

Pro Ala Phe Leu Asp Leu Glu Ala Gly Val Ala Lys Ala Ile Gly Leu
                20                  25                  30

Ile Ala Gln Ala Ala Ala Glu Gly Ala Ser Leu Val Ala Phe Pro Glu
            35                  40                  45

Ala Trp Leu Pro Gly Tyr Pro Trp Trp Ile Trp Leu Asp Ser Pro Ala
        50                  55                  60

Gly Gly Met Arg Phe Val Gln Arg Asn Phe Asp Asn Ala Leu Glu Val
65                  70                  75                  80

Gly Ser Glu Pro Phe Glu Arg Leu Cys Arg Ala Ala Gln His Lys
                85                  90                  95

Ile Tyr Val Val Leu Gly Phe Thr Glu Arg Ser Gly Gly Thr Leu Tyr
                100                 105                 110

Leu Ala Gln Ala Ile Ile Asp Asp Cys Gly Arg Val Val Ala Thr Arg
            115                 120                 125

Arg Lys Leu Lys Pro Thr His Val Glu Arg Ser Val Tyr Gly Glu Gly
        130                 135                 140

Asp Gly Ser Asp Leu Ala Val His Asp Thr Thr Leu Gly Arg Leu Gly
145                 150                 155                 160

Ala Leu Cys Cys Ala Glu His Ile Gln Pro Leu Ser Lys Tyr Ala Met
                165                 170                 175

Tyr Ala Gln His Glu Gln Val His Ile Ala Ala Trp Pro Ser Phe Ser
                180                 185                 190

Val Tyr Arg Gly Ala Ala Phe Gln Leu Ser Ala Gln Ala Asn Asn Ala
            195                 200                 205

Ala Ser Gln Val Tyr Ala Leu Glu Gly Gln Cys Phe Val Leu Ala Pro
        210                 215                 220

Cys Ala Thr Val Ser Lys Glu Met Leu Asp Glu Leu Ile Asp Ser Pro
225                 230                 235                 240

Ala Lys Ala Glu Leu Leu Leu Glu Gly Gly Gly Phe Ala Met Ile Tyr
                245                 250                 255
```

```
Gly Pro Asp Gly Ala Pro Leu Cys Thr Pro Leu Ala Glu Thr Glu Glu
            260                 265                 270

Gly Ile Leu Tyr Ala Asp Ile Asp Leu Gly Val Ile Gly Val Ala Lys
        275                 280                 285

Ala Ala Tyr Asp Pro Val Gly His Tyr Ser Arg Pro Asp Val Leu Arg
    290                 295                 300

Leu Leu Val Asn Arg Glu Pro Met Thr Arg Val His Tyr Val Gln Pro
305                 310                 315                 320

Gln Ser Leu Pro Glu Thr Ser Val Leu Ala Phe Gly Ala Gly Ala Asp
                325                 330                 335

Ala Ile Arg Ser Glu Glu Asn Pro Glu Glu Gln Gly Asp Lys Gly Ser
            340                 345                 350
```

<210> SEQ ID NO 15
<211> LENGTH: 1041
<212> TYPE: DNA
<213> ORGANISM: Agrobacterium rubi

<400> SEQUENCE: 15

| | | |
|---|---|---|
| atggaaaaga gtaagaccgt gcgtgccgcc gccgcccaga ttgctcctga tctgaccagt | 60 |
| cgcgataata ccctggcacg cgttctggat accattcatg aagcagccgg caaaggtgca | 120 |
| gaactgattg tgtttccgga aacctttgtg ccgtggtatc cgtattttag ttttgttctg | 180 |
| ccgccggttc tgagtggccg tgaacatctg cgtctgtatg aagaagcagt taccgttccg | 240 |
| agtgccacca ccgatgcagt ggccaccgca gcacgcgaac atggtattgt ggtggcactg | 300 |
| ggtgtgaatg aacgtgatca tggcaccctg tataatacccc agctggtgtt tgatgcagat | 360 |
| ggcgccctgg tgctgaaacg tcgcaaaatt ccccgacct tcatgaacg tatgatttgg | 420 |
| ggccaggggtg acgcaagtgg cctgaaagtg gtggatagcc aggttggccg cattggtgca | 480 |
| ctggcctgct gggaacatta taatccgctg gcacgttatg ccctgatggc ccagcatgaa | 540 |
| gaaattcatg ttgcccagtt tccgggcagc atggtgggcc cgattttgc agatcagatg | 600 |
| gaagtgacca ttcgtcatca tgcactggaa agtggttgtt ttgtggttaa tgccaccggt | 660 |
| tggctgaccg atgaacagat tcgtagtatt accccgatg aaaatctgca aaaagcactg | 720 |
| cgcggtggct gcatgaccgc cattattagt ccggaaggta acatctggc accgccgatg | 780 |
| accgaaggtg aaggcattct ggtgcagat ttggatatga gcctgattct gaaacgtaaa | 840 |
| cgtatgatgg atagtgtggg tcattatgcc cgcccggaac tgctgcatct ggttattgat | 900 |
| aatcgtccgg ccattaccat ggtgaccgcc catccgtttc tggaaaccgc accgaccggt | 960 |
| agtaataccg atggccatca gaccagcgcc tttgatggca tccggatca gcgcgccgca | 1020 |
| attctgcgcc gtcaggcagg c | 1041 |

<210> SEQ ID NO 16
<211> LENGTH: 347
<212> TYPE: PRT
<213> ORGANISM: Agrobacterium rubi

<400> SEQUENCE: 16

```
Met Glu Lys Ser Lys Thr Val Arg Ala Ala Ala Ala Gln Ile Ala Pro
1               5                   10                  15

Asp Leu Thr Ser Arg Asp Asn Thr Leu Ala Arg Val Leu Asp Thr Ile
            20                  25                  30

His Glu Ala Ala Gly Lys Gly Ala Glu Leu Ile Val Phe Pro Glu Thr
        35                  40                  45
```

Phe Val Pro Trp Tyr Pro Tyr Phe Ser Phe Val Leu Pro Pro Val Leu
50                  55                  60

Ser Gly Arg Glu His Leu Arg Leu Tyr Glu Glu Ala Val Thr Val Pro
65                  70                  75                  80

Ser Ala Thr Thr Asp Ala Val Ala Thr Ala Ala Arg Glu His Gly Ile
                85                  90                  95

Val Val Ala Leu Gly Val Asn Glu Arg Asp His Gly Thr Leu Tyr Asn
                100                 105                 110

Thr Gln Leu Val Phe Asp Ala Asp Gly Ala Leu Val Leu Lys Arg Arg
            115                 120                 125

Lys Ile Thr Pro Thr Phe His Glu Arg Met Ile Trp Gly Gln Gly Asp
130                 135                 140

Ala Ser Gly Leu Lys Val Val Asp Ser Gln Val Gly Arg Ile Gly Ala
145                 150                 155                 160

Leu Ala Cys Trp Glu His Tyr Asn Pro Leu Ala Arg Tyr Ala Leu Met
                165                 170                 175

Ala Gln His Glu Glu Ile His Val Ala Gln Phe Pro Gly Ser Met Val
            180                 185                 190

Gly Pro Ile Phe Ala Asp Gln Met Glu Val Thr Ile Arg His His Ala
        195                 200                 205

Leu Glu Ser Gly Cys Phe Val Val Asn Ala Thr Gly Trp Leu Thr Asp
210                 215                 220

Glu Gln Ile Arg Ser Ile Thr Pro Asp Glu Asn Leu Gln Lys Ala Leu
225                 230                 235                 240

Arg Gly Gly Cys Met Thr Ala Ile Ile Ser Pro Glu Gly Lys His Leu
                245                 250                 255

Ala Pro Pro Met Thr Glu Gly Glu Gly Ile Leu Val Ala Asp Leu Asp
            260                 265                 270

Met Ser Leu Ile Leu Lys Arg Lys Arg Met Met Asp Ser Val Gly His
        275                 280                 285

Tyr Ala Arg Pro Glu Leu Leu His Leu Val Ile Asp Asn Arg Pro Ala
290                 295                 300

Ile Thr Met Val Thr Ala His Pro Phe Leu Glu Thr Ala Pro Thr Gly
305                 310                 315                 320

Ser Asn Thr Asp Gly His Gln Thr Ser Ala Phe Asp Gly Asn Pro Asp
                325                 330                 335

Gln Arg Ala Ala Ile Leu Arg Arg Gln Ala Gly
            340                 345

<210> SEQ ID NO 17
<211> LENGTH: 990
<212> TYPE: DNA
<213> ORGANISM: Unknown
<220> FEATURE:
<223> OTHER INFORMATION: Unknown prokaryotic organism

<400> SEQUENCE: 17
atgaaggtgg ttaaagcagc agcagttcag attagcccgg ttctgtatag tcgcgaagcc    60
accgttgaaa aagttgttaa aaagattcac gagctgggcc agctgggtgt gcagtttgca   120 accttccgg aaaccgttgt tccgtattat ccgtatttta gtgcagttca gaccggtatt   180
gaactgctga gtggcaccga acatctgcgc ctgctggatc aggccgtgac cgttccgagt   240
ccggcaaccg atgcaattgg tgaagccgcc cgcaaagccg gtatggttgt gagtattggt   300
gttaatgaac gtgatggtgg caccctgtat aatacccagc tgctgtttga tgcagatggt   360

```
accctgattc agcgtcgtcg taaaattacc ccgacccatt ttgaacgcat gatttggggt    420
cagggtgacg gtagcggtct gcgtgcagtt gatagtaaag ttggtcgcat tggtcagctg    480
gcatgttttg aacataataa tccgctggcc cgctatgcac tgattgcaga tggtgaacag    540
attcatagcg caatgtatcc gggcagtgcc tttggtgaag ttttgcaca gcgtatggaa     600 attaatattc gtcagcatgc actggaaagt ggcgcatttg tggtgaatgc aaccgcatgg    660
ctggatgcag atcagcaggc acagattatt aaggataccg gttgtggtat tggtccgatt    720
agcggcggtt gttttaccac cattgtggca ccggatggta tgctgatggc cgaaccgctg    780
cgtagtggcg aaggcgaagt gattgttgat ctggattta ccctgattga tcgccgcaaa    840
atgctgatgg atagcgcagg ccattataat cgtccggaac tgctgagcct gatgattgat    900
cgcaccgcaa ccgcccatgt tcatgaacgc gccgcacatc cggtgagtgg tgccgaacag    960
ggcccggaag atttgcgcac cccggccgct                                     990
```

```
<210> SEQ ID NO 18
<211> LENGTH: 330
<212> TYPE: PRT
<213> ORGANISM: Unknown
<220> FEATURE:
<223> OTHER INFORMATION: Unknown prokaryotic organism

<400> SEQUENCE: 18
```

Met Lys Val Val Lys Ala Ala Val Gln Ile Ser Pro Val Leu Tyr
1               5                   10                  15

Ser Arg Glu Ala Thr Val Glu Lys Val Val Lys Ile His Glu Leu
                20                  25                  30

Gly Gln Leu Gly Val Gln Phe Ala Thr Phe Pro Glu Thr Val Val Pro
            35                  40                  45

Tyr Tyr Pro Tyr Phe Ser Ala Val Gln Thr Gly Ile Glu Leu Leu Ser
        50                  55                  60

Gly Thr Glu His Leu Arg Leu Leu Asp Gln Ala Val Thr Val Pro Ser
65                  70                  75                  80

Pro Ala Thr Asp Ala Ile Gly Glu Ala Ala Arg Lys Ala Gly Met Val
                85                  90                  95

Val Ser Ile Gly Val Asn Glu Arg Asp Gly Gly Thr Leu Tyr Asn Thr
            100                 105                 110

Gln Leu Leu Phe Asp Ala Asp Gly Thr Leu Ile Gln Arg Arg Arg Lys
        115                 120                 125

Ile Thr Pro Thr His Phe Glu Arg Met Ile Trp Gly Gln Gly Asp Gly
130                 135                 140

Ser Gly Leu Arg Ala Val Asp Ser Lys Val Gly Arg Ile Gly Gln Leu
145                 150                 155                 160

Ala Cys Phe Glu His Asn Asn Pro Leu Ala Arg Tyr Ala Leu Ile Ala
                165                 170                 175

Asp Gly Glu Gln Ile His Ser Ala Met Tyr Pro Gly Ser Ala Phe Gly
            180                 185                 190

Glu Gly Phe Ala Gln Arg Met Glu Ile Asn Ile Arg Gln His Ala Leu
        195                 200                 205

Glu Ser Gly Ala Phe Val Val Asn Ala Thr Ala Trp Leu Asp Ala Asp
210                 215                 220

Gln Gln Ala Gln Ile Ile Lys Asp Thr Gly Cys Gly Ile Gly Pro Ile
225                 230                 235                 240

Ser Gly Gly Cys Phe Thr Thr Ile Val Ala Pro Asp Gly Met Leu Met
                245                 250                 255

```
Ala Glu Pro Leu Arg Ser Gly Glu Gly Glu Val Ile Val Asp Leu Asp
                260                 265                 270

Phe Thr Leu Ile Asp Arg Arg Lys Met Leu Met Asp Ser Ala Gly His
            275                 280                 285

Tyr Asn Arg Pro Glu Leu Leu Ser Leu Met Ile Asp Arg Thr Ala Thr
        290                 295                 300

Ala His Val His Glu Arg Ala Ala His Pro Val Ser Gly Ala Glu Gln
305                 310                 315                 320

Gly Pro Glu Asp Leu Arg Thr Pro Ala Ala
                325                 330

<210> SEQ ID NO 19
<211> LENGTH: 1158
<212> TYPE: DNA
<213> ORGANISM: Candidatus Dadabacteria
<220> FEATURE:
<223> OTHER INFORMATION: Candidatus Dadabacteria bacterium CSP1-2

<400> SEQUENCE: 19
atgggtcagg tgctgggtgg tcgtgaacag gttcgtgccg ccgtggttca ggcaagtccg      60
gtttttatga ataagaaagg ttgtctggaa aaggcctgcg atctgattca taaagcaggt     120
aaagaaggcg cagaaattgt ggtgtttccg gaaacctgga ttccgaccta tccgtattgg     180
ggtatgggtt gggataccgc agcagcagca tttgccgatg ttcatgccga tctgcaagat     240
aatagcctgg tggttggcag caaagatacc gatattctgg gtaaagcagc ccgcgatgcc     300
ggtgcctatg ttgttatggg ctgcaatgaa ctggatgatc gcattggcag ccgtaccctg     360
tttaatagtc tggtttatat tggcaaagac ggccgtgtta tgggtcgtca tcgtaaactg     420
attccgagtt atattgaacg catttggtgg ggtcgcggtg acgcccgtga tctgaaagtt     480
tttgataccg atatcggccg cattggtggt cagatttgtt gggaaaatca tattgttaac     540
atcaccgcct ggtttattgc ccagggcgtt gatattcatg ttgcagtttg gccgggtctg     600
tggaattgtg gtgccgcaca gggtgaaagt tttatctatg caggccatga tattaataag     660
tgcgatctga tcccggccac ccgcgaacgc gcctttaccg tcagtgctt tgttctgagc     720 gcaaataata ttctgcgcat ggatgaaatt ccggatgatt ttccgtttaa aaataagatg     780
acctacgcag gtccgggtca gggtgaattt gttggctggg catgtggtgg tagtcatatt     840
gttgcaccga ccagcgaata tattgtgccg ccgacctttg atgttgaaac cattctgtat     900
gcagatttga tgccaaaata tattaaggtt gtgaagagcg ttttcgatag tctgggccat     960
tatacccgct gggatctggt gagtctgacc aaacagccgc agccgtatga accgctggca    1020
ggcgaacgcc cgatggcaat gccggaagaa cgtattgaac aggttgccga tgcagtggcc    1080
cgtgagttta tctggatgt tgaaaaagtt gataagatcg tgcgtcaggt taccaccccg    1140
catcgtcagc gcgcagcc                                                  1158

<210> SEQ ID NO 20
<211> LENGTH: 386
<212> TYPE: PRT
<213> ORGANISM: Candidatus Dadabacteria
<220> FEATURE:
<223> OTHER INFORMATION: Candidatus Dadabacteria bacterium CSP1-2

<400> SEQUENCE: 20

Met Gly Gln Val Leu Gly Gly Arg Glu Gln Val Arg Ala Ala Val Val
1               5                   10                  15
```

-continued

Gln Ala Ser Pro Val Phe Met Asn Lys Lys Gly Cys Leu Glu Lys Ala
            20                  25                  30

Cys Asp Leu Ile His Lys Ala Gly Lys Glu Gly Ala Glu Ile Val Val
        35                  40                  45

Phe Pro Glu Thr Trp Ile Pro Thr Tyr Pro Tyr Trp Gly Met Gly Trp
    50                  55                  60

Asp Thr Ala Ala Ala Phe Ala Asp Val His Ala Asp Leu Gln Asp
65                  70                  75                  80

Asn Ser Leu Val Val Gly Ser Lys Asp Thr Asp Ile Leu Gly Lys Ala
                85                  90                  95

Ala Arg Asp Ala Gly Ala Tyr Val Val Met Gly Cys Asn Glu Leu Asp
            100                 105                 110

Asp Arg Ile Gly Ser Arg Thr Leu Phe Asn Ser Leu Val Tyr Ile Gly
        115                 120                 125

Lys Asp Gly Arg Val Met Gly Arg His Arg Lys Leu Ile Pro Ser Tyr
    130                 135                 140

Ile Glu Arg Ile Trp Trp Gly Arg Gly Asp Ala Arg Asp Leu Lys Val
145                 150                 155                 160

Phe Asp Thr Asp Ile Gly Arg Ile Gly Gly Gln Ile Cys Trp Glu Asn
                165                 170                 175

His Ile Val Asn Ile Thr Ala Trp Phe Ile Ala Gln Gly Val Asp Ile
            180                 185                 190

His Val Ala Val Trp Pro Gly Leu Trp Asn Cys Gly Ala Ala Gln Gly
        195                 200                 205

Glu Ser Phe Ile Tyr Ala Gly His Asp Ile Asn Lys Cys Asp Leu Ile
    210                 215                 220

Pro Ala Thr Arg Glu Arg Ala Phe Thr Gly Gln Cys Phe Val Leu Ser
225                 230                 235                 240

Ala Asn Asn Ile Leu Arg Met Asp Glu Ile Pro Asp Asp Phe Pro Phe
                245                 250                 255

Lys Asn Lys Met Thr Tyr Ala Gly Pro Gly Gln Gly Glu Phe Val Gly
            260                 265                 270

Trp Ala Cys Gly Gly Ser His Ile Val Ala Pro Thr Ser Glu Tyr Ile
        275                 280                 285

Val Pro Pro Thr Phe Asp Val Glu Thr Ile Leu Tyr Ala Asp Leu Asn
    290                 295                 300

Ala Lys Tyr Ile Lys Val Val Lys Ser Val Phe Asp Ser Leu Gly His
305                 310                 315                 320

Tyr Thr Arg Trp Asp Leu Val Ser Leu Thr Lys Gln Pro Gln Pro Tyr
                325                 330                 335

Glu Pro Leu Ala Gly Glu Arg Pro Met Ala Met Pro Glu Glu Arg Ile
            340                 345                 350

Glu Gln Val Ala Asp Ala Val Ala Arg Glu Phe Asn Leu Asp Val Glu
        355                 360                 365

Lys Val Asp Lys Ile Val Arg Gln Val Thr Thr Pro His Arg Gln Arg
    370                 375                 380

Ala Ala
385

<210> SEQ ID NO 21
<211> LENGTH: 963
<212> TYPE: DNA
<213> ORGANISM: Unknown
<220> FEATURE:
<223> OTHER INFORMATION: Unknown prokaryotic organism

<400> SEQUENCE: 21

```
atgtcaaacg agaacaacaa cgctacattc aaagttgccg cagtacaggc tacacctgtt    60
tttctcgatc gtgaagcgac tctcgacaag gcttgcgatt tgatcgccgc cgccggaggt   120
gaagggcac gattggttgt ctttccagaa gccttcatac cggcctatcc ggattgggta   180
tgggcaatcc caccgggtga agagggcgta cttaatgagt tgtacgcaga gctgctctcc   240
aactcggtca cgattcccag tgacgcgacg gacagactgt gccgggccgc gaggcttgct   300
aatgcttacg tggtgatggg ataagcgaa cgcaatgtcg aggcgagtgg agcaagcctg   360
tataacacgc tgttgtacat cgatgcgcag ggtgagattc taggcaaaca tcgaaagcta   420
gtgccaacgg cggcgagcg gctggtgtgg gcgcagggcg atggcagcac actgcaggtc   480
tacgatactc cactgggaaa actcggcggt taatttgct gggagaatta tatgccgctg   540
gcccgctata ccatgtatgc ctggggcaca caaatctatg tcgccgctac gtgggatcgc   600
gggcaaccct ggctctccac tttgcggcat atcgccaaag aaggcagggt gtacgtgatt   660
ggttgttgta tcgcgatgcg caaagacgat atccctgatc gttacgcaat gaagcagaag   720
ttttacgcgg aggcagatga gtggatcaat ataggtgaca gcgcgattgt caatcctgaa   780
gggcaattta tcgcagggcc agtacgcaag caggaagaga ttctctacgc agagattgat   840
ccgcgcatgg tacaagggcc gaagtggatg ctcgacgtgg cggggcacta tgccaggccg   900
gatgtgttcc agttgacggt gcatacggat gtgcgacaga tgattcggat ggaacacgat   960
tct                                                                963
```

<210> SEQ ID NO 22
<211> LENGTH: 321
<212> TYPE: PRT
<213> ORGANISM: Unknown
<220> FEATURE:
<223> OTHER INFORMATION: Unknown prokaryotic organism

<400> SEQUENCE: 22

```
Met Ser Asn Glu Asn Asn Asn Ala Thr Phe Lys Val Ala Ala Val Gln
1               5                   10                  15

Ala Thr Pro Val Phe Leu Asp Arg Glu Ala Thr Leu Asp Lys Ala Cys
            20                  25                  30

Asp Leu Ile Ala Ala Ala Gly Gly Glu Gly Ala Arg Leu Val Val Phe
        35                  40                  45

Pro Glu Ala Phe Ile Pro Ala Tyr Pro Asp Trp Val Trp Ala Ile Pro
    50                  55                  60

Pro Gly Glu Glu Gly Val Leu Asn Glu Leu Tyr Ala Glu Leu Leu Ser
65                  70                  75                  80

Asn Ser Val Thr Ile Pro Ser Asp Ala Thr Asp Arg Leu Cys Arg Ala
                85                  90                  95

Ala Arg Leu Ala Asn Ala Tyr Val Val Met Gly Ile Ser Glu Arg Asn
            100                 105                 110

Val Glu Ala Ser Gly Ala Ser Leu Tyr Asn Thr Leu Leu Tyr Ile Asp
        115                 120                 125

Ala Gln Gly Glu Ile Leu Gly Lys His Arg Lys Leu Val Pro Thr Gly
    130                 135                 140

Gly Glu Arg Leu Val Trp Ala Gln Gly Asp Gly Ser Thr Leu Gln Val
145                 150                 155                 160

Tyr Asp Thr Pro Leu Gly Lys Leu Gly Gly Leu Ile Cys Trp Glu Asn
                165                 170                 175
```

Tyr Met Pro Leu Ala Arg Tyr Thr Met Tyr Ala Trp Gly Thr Gln Ile
            180                 185                 190

Tyr Val Ala Ala Thr Trp Asp Arg Gly Gln Pro Trp Leu Ser Thr Leu
        195                 200                 205

Arg His Ile Ala Lys Glu Gly Arg Val Tyr Val Ile Gly Cys Cys Ile
    210                 215                 220

Ala Met Arg Lys Asp Asp Ile Pro Asp Arg Tyr Ala Met Lys Gln Lys
225                 230                 235                 240

Phe Tyr Ala Glu Ala Asp Glu Trp Ile Asn Ile Gly Asp Ser Ala Ile
                245                 250                 255

Val Asn Pro Glu Gly Gln Phe Ile Ala Gly Pro Val Arg Lys Gln Glu
            260                 265                 270

Glu Ile Leu Tyr Ala Glu Ile Asp Pro Arg Met Val Gln Gly Pro Lys
        275                 280                 285

Trp Met Leu Asp Val Ala Gly His Tyr Ala Arg Pro Asp Val Phe Gln
    290                 295                 300

Leu Thr Val His Thr Asp Val Arg Gln Met Ile Arg Met Glu His Asp
305                 310                 315                 320

Ser

<210> SEQ ID NO 23

<400> SEQUENCE: 23

000

<210> SEQ ID NO 24

<400> SEQUENCE: 24

000

<210> SEQ ID NO 25
<211> LENGTH: 972
<212> TYPE: DNA
<213> ORGANISM: Tepidicaulis marinus

<400> SEQUENCE: 25

```
atgacccgtg ttgctgctat ccagatggaa gctaaagttg ctgacctgaa cttcaacatc      60
gaccaggctt ctcgtctgat cgacgaagct ggttctaaag gtgctgaaat catcgctctg     120
ccggaattct tcaccacccg tatcgtttac gacgaacgtc tgttcgaatg ctctctgccg     180
ccggaaaaacc cggctctgga catgctgaaa gctaaagctg ctaaatacgg tgctatgatc     240
ggtggttctt acctggaaat gcgtgacggt gacgtttaca cacctacac cctggttgaa     300
ccggacggta ccgttcaccg tcacgacaaa gaccgtccga ccatggttga aaacgctttc     360
tacaccggtg ttctgacga cggttacttc gaaaccgcta tgggtccggt tggtaccgct     420
gtttgctggg aactgatccg taccgctacc gttcgtcgtc tggctggtaa agttggtctg     480
atgatgaccg ttctcactg gtggtctgct ccgggttgga acttctggaa atctttcgaa     540
cgtcgtttcc acaaagctaa cggtaaagct atggaaatca cccgccgcg tttcgcttct     600
ctggttggtg ctccgctgct gcacgctggt cacaccggta tgctggaagg tggtttcctg     660
gttctgccgg gtaccgtat ctctgttccg accgtaccc agctgatggg tgaaacccag     720
atcatcgacg tgaaggtgc tgttgttgct cgtcgtcact acaccgaagg tgctggtatc     780
gttggtggtg aaatcgaact gggtgctacc tctccgaaaa agctccgcc ggaccgtttc     840
```

```
tggatcccga acctggaagg tttcccgaaa gctctgtggc tgcaccagaa cccggctggt    900
gcttctgttt accgttgggc taaacgtacc ggtcgtctga aaacctacga cttctctcgt    960
aacgctcgtc cg                                                        972
```

<210> SEQ ID NO 26
<211> LENGTH: 324
<212> TYPE: PRT
<213> ORGANISM: Tepidicaulis marinus

<400> SEQUENCE: 26

```
Met Thr Arg Val Ala Ala Ile Gln Met Glu Ala Lys Val Ala Asp Leu
1               5                   10                  15

Asn Phe Asn Ile Asp Gln Ala Ser Arg Leu Ile Asp Glu Ala Gly Ser
            20                  25                  30

Lys Gly Ala Glu Ile Ile Ala Leu Pro Glu Phe Phe Thr Thr Arg Ile
        35                  40                  45

Val Tyr Asp Glu Arg Leu Phe Glu Cys Ser Leu Pro Pro Glu Asn Pro
    50                  55                  60

Ala Leu Asp Met Leu Lys Ala Lys Ala Ala Lys Tyr Gly Ala Met Ile
65                  70                  75                  80

Gly Gly Ser Tyr Leu Glu Met Arg Asp Gly Asp Val Tyr Asn Thr Tyr
                85                  90                  95

Thr Leu Val Glu Pro Asp Gly Thr Val His Arg His Asp Lys Asp Arg
            100                 105                 110

Pro Thr Met Val Glu Asn Ala Phe Tyr Thr Gly Gly Ser Asp Asp Gly
        115                 120                 125

Tyr Phe Glu Thr Ala Met Gly Pro Val Gly Thr Ala Val Cys Trp Glu
    130                 135                 140

Leu Ile Arg Thr Ala Thr Val Arg Arg Leu Ala Gly Lys Val Gly Leu
145                 150                 155                 160

Met Met Thr Gly Ser His Trp Trp Ser Ala Pro Gly Trp Asn Phe Trp
                165                 170                 175

Lys Ser Phe Glu Arg Arg Phe His Lys Ala Asn Gly Lys Ala Met Glu
            180                 185                 190

Ile Thr Pro Pro Arg Phe Ala Ser Leu Val Gly Ala Pro Leu Leu His
        195                 200                 205

Ala Gly His Thr Gly Met Leu Glu Gly Gly Phe Leu Val Leu Pro Gly
    210                 215                 220

Thr Arg Ile Ser Val Pro Thr Arg Thr Gln Leu Met Gly Glu Thr Gln
225                 230                 235                 240

Ile Ile Asp Gly Glu Gly Ala Val Val Ala Arg Arg His Tyr Thr Glu
                245                 250                 255

Gly Ala Gly Ile Val Gly Gly Glu Ile Glu Leu Gly Ala Thr Ser Pro
            260                 265                 270

Lys Lys Ala Pro Pro Asp Arg Phe Trp Ile Pro Asn Leu Glu Gly Phe
        275                 280                 285

Pro Lys Ala Leu Trp Leu His Gln Asn Pro Ala Gly Ala Ser Val Tyr
    290                 295                 300

Arg Trp Ala Lys Arg Thr Gly Arg Leu Lys Thr Tyr Asp Phe Ser Arg
305                 310                 315                 320

Asn Ala Arg Pro
```

<210> SEQ ID NO 27

<211> LENGTH: 1014
<212> TYPE: DNA
<213> ORGANISM: Unknown
<220> FEATURE:
<223> OTHER INFORMATION: Unknown prokaryotic organism

<400> SEQUENCE: 27

```
atgggtatcg aacacccgaa atacaaagtt gctgttgttc aggctgctcc ggcttggctg     60
gacctggacg cttctatcga caaatctatc gctctgatcg aagaagctgc tcagaaaggt    120
gctaaactga tcgctttccc ggaagctttc atcccgggtt acccgtggca catctggatg    180
gactctccgg cttgggctat cggtcgtggt ttcgttcagc gttacttcga caactctctg    240
gcttacgact ctccgcaggc tgaaaaactg cgtgctgctg ttcgtaaagc taaactgacc    300
gctgttctgg gtctgtctga acgtgacggt ggttctctgt acctggctca gtggctgatc    360
ggtccggacg gtgaaaccat cgctaaacgt cgtaaactgc gtccgaccca cgctgaacgt    420
accgtttacg gtgaaggtga cggttctgac ctggctgttc acaaccgtcc ggacatcggt    480
cgtctgggtg ctctgtgctg ctgggaacac ctgcagccgc tgtctaaata cgctatgtac    540
gctcagaacg aacaggttca cgttgctgct tggccgtctt tctctctgta cgacccgttc    600
gctgttgctc tgggtgctga agttaacaac gctgcttctc gtgtttacgc tgttgaaggt    660
tcttgcttcg ttctggctcc gtgcgctacc gtttctcagg ctatgatcga cgaactgtgc    720
gaccgtccgg acaaacacac cctgctgcac gttggtggtg gtttcgctgc tatctacggt    780
ccggacggtt ctcagatcgg tgacaaactg gctccggacc aggaaggtct gctgatcgct    840
gaaatcgacc tgggtgctat cggtgttgct aaaaacgctg ctgacccggc tggtcactac    900
tctcgtccgg acgttacccg tctgctgctg aacaaaaaac cgtacaaacg tgttgaacag    960
ttctctccgc cggctgaagc tgttgaaccg accgacatcg ctgctgctgc ttct         1014
```

<210> SEQ ID NO 28
<211> LENGTH: 338
<212> TYPE: PRT
<213> ORGANISM: Unknown
<220> FEATURE:
<223> OTHER INFORMATION: Unknown prokaryotic organism

<400> SEQUENCE: 28

```
Met Gly Ile Glu His Pro Lys Tyr Lys Val Ala Val Val Gln Ala Ala
1               5                   10                  15

Pro Ala Trp Leu Asp Leu Asp Ala Ser Ile Asp Lys Ser Ile Ala Leu
            20                  25                  30

Ile Glu Glu Ala Ala Gln Lys Gly Ala Lys Leu Ile Ala Phe Pro Glu
        35                  40                  45

Ala Phe Ile Pro Gly Tyr Pro Trp His Ile Trp Met Asp Ser Pro Ala
    50                  55                  60

Trp Ala Ile Gly Arg Gly Phe Val Gln Arg Tyr Phe Asp Asn Ser Leu
65                  70                  75                  80

Ala Tyr Asp Ser Pro Gln Ala Glu Lys Leu Arg Ala Ala Val Arg Lys
                85                  90                  95

Ala Lys Leu Thr Ala Val Leu Gly Leu Ser Glu Arg Asp Gly Gly Ser
            100                 105                 110

Leu Tyr Leu Ala Gln Trp Leu Ile Gly Pro Asp Gly Glu Thr Ile Ala
        115                 120                 125

Lys Arg Arg Lys Leu Arg Pro Thr His Ala Glu Arg Thr Val Tyr Gly
    130                 135                 140
```

Glu Gly Asp Gly Ser Asp Leu Ala Val His Asn Arg Pro Asp Ile Gly
145                 150                 155                 160

Arg Leu Gly Ala Leu Cys Cys Trp Glu His Leu Gln Pro Leu Ser Lys
                165                 170                 175

Tyr Ala Met Tyr Ala Gln Asn Glu Gln Val His Val Ala Ala Trp Pro
            180                 185                 190

Ser Phe Ser Leu Tyr Asp Pro Phe Ala Val Ala Leu Gly Ala Glu Val
        195                 200                 205

Asn Asn Ala Ala Ser Arg Val Tyr Ala Val Glu Gly Ser Cys Phe Val
    210                 215                 220

Leu Ala Pro Cys Ala Thr Val Ser Gln Ala Met Ile Asp Glu Leu Cys
225                 230                 235                 240

Asp Arg Pro Asp Lys His Thr Leu Leu His Val Gly Gly Phe Ala
                245                 250                 255

Ala Ile Tyr Gly Pro Asp Gly Ser Gln Ile Gly Asp Lys Leu Ala Pro
            260                 265                 270

Asp Gln Glu Gly Leu Leu Ile Ala Glu Ile Asp Leu Gly Ala Ile Gly
        275                 280                 285

Val Ala Lys Asn Ala Ala Asp Pro Ala Gly His Tyr Ser Arg Pro Asp
290                 295                 300

Val Thr Arg Leu Leu Leu Asn Lys Lys Pro Tyr Lys Arg Val Glu Gln
305                 310                 315                 320

Phe Ser Pro Pro Ala Glu Ala Val Glu Pro Thr Asp Ile Ala Ala Ala
                325                 330                 335

Ala Ser

<210> SEQ ID NO 29
<211> LENGTH: 1014
<212> TYPE: DNA
<213> ORGANISM: Unknown
<220> FEATURE:
<223> OTHER INFORMATION: Unknown prokaryotic organism

<400> SEQUENCE: 29
atgggtatcg aacacccgaa atacaaagtt gctgttgttc aggctgctcc ggcttggctg      60
gacctggacg ttctgttga caaatctatc gctctgatca agaagctgc tgaaaaaggt      120
gctaaactga tcgctttccc ggaagctttc atcccgggtt accgtggca catctggatg      180
gactctccgg cttgggctat cggtcgtggt ttcgttcagc gttacttcga caactctctg      240
tcttacgact ctccgcaggc tgaacgtctg cgtgacgctg ttaaaaaagc taaactgacc      300
gctgttttcg gtctgtctga acgtgacggt ggttctctgt acctggctca gtggctgatc      360
ggtccggacg tgaaaccat cgctaaacgt cgtaaactgc gtccgaccca cgctgaacgt      420
accgtttacg gtgaaggtga cggttctgac ctggctgttc acgtcgtgc tgacatcggt      480
cgtatcggtg ctctgtgctg ctgggaacac ctgcagccgc tgtctaaata cgctatgtac      540
gctcagaacg aacaggttca cgttgctgct tggccgtctt tctctctgta cgacccgttc      600
gctccggctc tgggtgctga agttaacaac gctgcttctc gtgtttacgc tgttgaaggt      660
tcttgcttcg ttctggctcc gtgcgctacc gtttctcagg ctatgatcga cgaactgtgc      720
gaccgtccgg acaaaaacgc tctgctgcac gttggtggtg gtttcgctgc tatctacggt      780
ccggacggtt ctcagatcgg tgacaaactg gctccggacc aggaaggtct gctgatcgct      840
gaaatcgacc tgggtgctat cggtgttgct aaaaacgctg ctgacccggc tggtcactac      900
tctcgtccgg acgttacccg tctgctgctg aacaaaaaac gttaccagcg tgttgaacag      960

-continued

```
ttcgctctgc cggttgacac cgttgaaccg gctgacatcg gtgctgctgc ttct         1014
```

<210> SEQ ID NO 30
<211> LENGTH: 338
<212> TYPE: PRT
<213> ORGANISM: Unknown
<220> FEATURE:
<223> OTHER INFORMATION: Unknown prokaryotic organism

<400> SEQUENCE: 30

Met Gly Ile Glu His Pro Lys Tyr Lys Val Ala Val Gln Ala Ala
1               5                   10                  15

Pro Ala Trp Leu Asp Leu Asp Gly Ser Val Asp Lys Ser Ile Ala Leu
            20                  25                  30

Ile Lys Glu Ala Ala Glu Lys Gly Ala Lys Leu Ile Ala Phe Pro Glu
        35                  40                  45

Ala Phe Ile Pro Gly Tyr Pro Trp His Ile Trp Met Asp Ser Pro Ala
    50                  55                  60

Trp Ala Ile Gly Arg Gly Phe Val Gln Arg Tyr Phe Asp Asn Ser Leu
65                  70                  75                  80

Ser Tyr Asp Ser Pro Gln Ala Glu Arg Leu Arg Asp Ala Val Lys Lys
                85                  90                  95

Ala Lys Leu Thr Ala Val Phe Gly Leu Ser Glu Arg Asp Gly Gly Ser
            100                 105                 110

Leu Tyr Leu Ala Gln Trp Leu Ile Gly Pro Asp Gly Glu Thr Ile Ala
        115                 120                 125

Lys Arg Arg Lys Leu Arg Pro Thr His Ala Glu Arg Thr Val Tyr Gly
    130                 135                 140

Glu Gly Asp Gly Ser Asp Leu Ala Val His Ala Arg Ala Asp Ile Gly
145                 150                 155                 160

Arg Ile Gly Ala Leu Cys Cys Trp Glu His Leu Gln Pro Leu Ser Lys
                165                 170                 175

Tyr Ala Met Tyr Ala Gln Asn Glu Gln Val His Val Ala Ala Trp Pro
            180                 185                 190

Ser Phe Ser Leu Tyr Asp Pro Phe Ala Pro Ala Leu Gly Ala Glu Val
        195                 200                 205

Asn Asn Ala Ala Ser Arg Val Tyr Ala Val Glu Gly Ser Cys Phe Val
    210                 215                 220

Leu Ala Pro Cys Ala Thr Val Ser Gln Ala Met Ile Asp Glu Leu Cys
225                 230                 235                 240

Asp Arg Pro Asp Lys Asn Ala Leu Leu His Val Gly Gly Gly Phe Ala
                245                 250                 255

Ala Ile Tyr Gly Pro Asp Gly Ser Gln Ile Gly Asp Lys Leu Ala Pro
            260                 265                 270

Asp Gln Glu Gly Leu Leu Ile Ala Glu Ile Asp Leu Gly Ala Ile Gly
        275                 280                 285

Val Ala Lys Asn Ala Ala Asp Pro Ala Gly His Tyr Ser Arg Pro Asp
    290                 295                 300

Val Thr Arg Leu Leu Leu Asn Lys Lys Arg Tyr Gln Arg Val Glu Gln
305                 310                 315                 320

Phe Ala Leu Pro Val Asp Thr Val Glu Pro Ala Asp Ile Gly Ala Ala
                325                 330                 335

Ala Ser

<210> SEQ ID NO 31
<211> LENGTH: 1011
<212> TYPE: DNA
<213> ORGANISM: Unknown
<220> FEATURE:
<223> OTHER INFORMATION: Unknown prokaryotic organism

<400> SEQUENCE: 31

```
atgggtatca cccacccgaa ctacaaagtt gctgttgttc aggctgctcc ggtttggctg      60
aacctggaag ctaccgttga aaaaccatc cgttacatcg aagaagctgc taaagctggt     120
gctaaactga tcgctttccc ggaaacctgg atcccgggtt accgtggca catctggatc     180
ggtaccccgg cttgggctat cggtaaaggt ttcgttcagc gttacttcga caactctctg     240
tcttacgact ctccgctggc tcgtcagatc gctgacgctg ctgctaaatc taaaatcacc     300
gttgttctgg gtctgtctga acgtgacggt ggttctctgt acatcgctca gtggctgatc     360
ggtccggacg gtgaaaccat cgctaaacgt cgtaaactgc gtccgaccca cgttgaacgt     420
accgttttcg gtgacggtga cggttctcac atcgctgttc acgaccgttc tgacctgggt     480
cgtctgggtg ctctgtgctg ctgggaacac gttcagccgc tgaccaaatt cgctatgtac     540
gctcagaacg aacaggttca cgttgctgct tggccgtctt tctctatgta cgaaccgttc     600
gctcacgctc tgggttggga accaacaac gctgttttcta aagtttacgc tgttgaaggt     660
tcttgcttcg ttctggctcc gtgcgctgtt atctctcagg ctatggttga cgaaatgtgc     720
gacaccccgg acaaacgtga actggttcac gctggtggtg gtcacgctgt tatctacggt     780
ccggacggtt ctccgctggc tgaaaaactg ggtgaaaacg aagaaggtct gctgtacgct     840
accgttaacc tggctgctat cggtgttgct aaaaacgctg ctgacccggc tggtcactac     900
tctcgtccgg acgttctgcg tctgctgttc aacaaatctc cggctcgtcg tgttgaacac     960
ttcgctctgc cgcacgaaca gctggaaatc ggtgctggtc cgtctggtga c           1011
```

<210> SEQ ID NO 32
<211> LENGTH: 337
<212> TYPE: PRT
<213> ORGANISM: Unknown
<220> FEATURE:
<223> OTHER INFORMATION: Unknown prokaryotic organism

<400> SEQUENCE: 32

```
Met Gly Ile Thr His Pro Asn Tyr Lys Val Ala Val Val Gln Ala Ala
1               5                   10                  15

Pro Val Trp Leu Asn Leu Glu Ala Thr Val Glu Lys Thr Ile Arg Tyr
            20                  25                  30

Ile Glu Glu Ala Ala Lys Ala Gly Ala Lys Leu Ile Ala Phe Pro Glu
        35                  40                  45

Thr Trp Ile Pro Gly Tyr Pro Trp His Ile Trp Ile Gly Thr Pro Ala
    50                  55                  60

Trp Ala Ile Gly Lys Gly Phe Val Gln Arg Tyr Phe Asp Asn Ser Leu
65                  70                  75                  80

Ser Tyr Asp Ser Pro Leu Ala Arg Gln Ile Ala Asp Ala Ala Ala Lys
                85                  90                  95

Ser Lys Ile Thr Val Val Leu Gly Leu Ser Glu Arg Asp Gly Gly Ser
            100                 105                 110

Leu Tyr Ile Ala Gln Trp Leu Ile Gly Pro Asp Gly Glu Thr Ile Ala
        115                 120                 125

Lys Arg Arg Lys Leu Arg Pro Thr His Val Glu Arg Thr Val Phe Gly
    130                 135                 140
```

Asp Gly Asp Gly Ser His Ile Ala Val His Asp Arg Ser Asp Leu Gly
145                 150                 155                 160

Arg Leu Gly Ala Leu Cys Cys Trp Glu His Val Gln Pro Leu Thr Lys
                165                 170                 175

Phe Ala Met Tyr Ala Gln Asn Glu Gln Val His Val Ala Ala Trp Pro
            180                 185                 190

Ser Phe Ser Met Tyr Glu Pro Phe Ala His Ala Leu Gly Trp Glu Thr
        195                 200                 205

Asn Asn Ala Val Ser Lys Val Tyr Ala Val Glu Gly Ser Cys Phe Val
210                 215                 220

Leu Ala Pro Cys Ala Val Ile Ser Gln Ala Met Val Asp Glu Met Cys
225                 230                 235                 240

Asp Thr Pro Asp Lys Arg Glu Leu Val His Ala Gly Gly His Ala
                245                 250                 255

Val Ile Tyr Gly Pro Asp Gly Ser Pro Leu Ala Glu Lys Leu Gly Glu
            260                 265                 270

Asn Glu Glu Gly Leu Leu Tyr Ala Thr Val Asn Leu Ala Ala Ile Gly
        275                 280                 285

Val Ala Lys Asn Ala Ala Asp Pro Ala Gly His Tyr Ser Arg Pro Asp
            290                 295                 300

Val Leu Arg Leu Leu Phe Asn Lys Ser Pro Ala Arg Arg Val Glu His
305                 310                 315                 320

Phe Ala Leu Pro His Glu Gln Leu Glu Ile Gly Ala Gly Pro Ser Gly
                325                 330                 335

Asp

<210> SEQ ID NO 33
<211> LENGTH: 996
<212> TYPE: DNA
<213> ORGANISM: Synechococcus sp.
<220> FEATURE:
<223> OTHER INFORMATION: Synechococcus sp. CC9605

<400> SEQUENCE: 33
atgaccaccg ttaaagttgc tgctgctcag atccgtccgg ttctgttctc tctggacggt      60
tctctgcaga aagttctgga cgctatggct gaagctgctg ctcagggtgt gaactgatc     120 gttttcccgg aaaccttcct gccgtactac ccgtacttct ctttcgttga ccgccggtt     180 ctgatgggtc gttctcacct ggctctgtac gaacaggctg ttgttgttcc gggtccggtt     240
accgacgctg ttgctgctgc tgcttctcag tacggtatgc aggttctgct gggtgttaac     300
gaacgtgacg gtggtaccct gtacaacacc cagctgctgt tcaactcttg cggtgaactg     360
gttctgaaac gtcgtaaaat caccccgacc taccacgaac gtatggtttg gggtcagggt     420
gacggttctg gtctgaaagt tgttcagacc ccgctggctc gtgttggtgc tctggcttgc     480
tgggaacact acaacccgct ggctcgttac gctctgatgg ctcagggtga agaaatccac     540
tgcgctcagt tcccgggttc tctggttggt ccgatcttca ccgaacagac cgctgttacc     600
atgcgtcacc acgctctgga agctggttgc ttcgttatct gctctaccgg ttggctgcac     660
ccggacgact acgcttctat cacctctgaa tctggtctgc acaaagcttt ccagggtggt     720
tgccacaccg ctgttatctc tccggaaggt cgttacctgg ctggtccgct gccggacggt     780
gaaggtctgg ctatcgctga cctggacctg gctctgatca ccaaacgtaa acgtatgatg     840
gactctgttg gtcactactc tcgtccggaa ctgctgtctc tgcagatcaa ctcttctccg     900

```
gctgttccgg ttcagaacat gtctaccgct tctgttccgc tggaaccggc taccgctacc    960
gacgctctgt cttctatgga agctctgaac cacgtt                              996
```

<210> SEQ ID NO 34
<211> LENGTH: 332
<212> TYPE: PRT
<213> ORGANISM: Synechococcus sp.
<220> FEATURE:
<223> OTHER INFORMATION: Synechococcus sp. CC9605

<400> SEQUENCE: 34

```
Met Thr Thr Val Lys Val Ala Ala Gln Ile Arg Pro Val Leu Phe
1               5                  10                  15

Ser Leu Asp Gly Ser Leu Gln Lys Val Leu Asp Ala Met Ala Glu Ala
                20                  25                  30

Ala Ala Gln Gly Val Glu Leu Ile Val Phe Pro Glu Thr Phe Leu Pro
            35                  40                  45

Tyr Tyr Pro Tyr Phe Ser Phe Val Glu Pro Val Leu Met Gly Arg
50                  55                  60

Ser His Leu Ala Leu Tyr Glu Gln Ala Val Val Pro Gly Pro Val
65                  70                  75                  80

Thr Asp Ala Val Ala Ala Ala Ser Gln Tyr Gly Met Gln Val Leu
                85                  90                  95

Leu Gly Val Asn Glu Arg Asp Gly Gly Thr Leu Tyr Asn Thr Gln Leu
            100                 105                 110

Leu Phe Asn Ser Cys Gly Glu Leu Val Leu Lys Arg Arg Lys Ile Thr
        115                 120                 125

Pro Thr Tyr His Glu Arg Met Val Trp Gly Gln Gly Asp Gly Ser Gly
    130                 135                 140

Leu Lys Val Val Gln Thr Pro Leu Ala Arg Val Gly Ala Leu Ala Cys
145                 150                 155                 160

Trp Glu His Tyr Asn Pro Leu Ala Arg Tyr Ala Leu Met Ala Gln Gly
                165                 170                 175

Glu Glu Ile His Cys Ala Gln Phe Pro Gly Ser Leu Val Gly Pro Ile
            180                 185                 190

Phe Thr Glu Gln Thr Ala Val Thr Met Arg His His Ala Leu Glu Ala
        195                 200                 205

Gly Cys Phe Val Ile Cys Ser Thr Gly Trp Leu His Pro Asp Asp Tyr
    210                 215                 220

Ala Ser Ile Thr Ser Glu Ser Gly Leu His Lys Ala Phe Gln Gly Gly
225                 230                 235                 240

Cys His Thr Ala Val Ile Ser Pro Glu Gly Arg Tyr Leu Ala Gly Pro
                245                 250                 255

Leu Pro Asp Gly Glu Gly Leu Ala Ile Ala Asp Leu Asp Leu Ala Leu
            260                 265                 270

Ile Thr Lys Arg Lys Arg Met Met Asp Ser Val Gly His Tyr Ser Arg
        275                 280                 285

Pro Glu Leu Leu Ser Leu Gln Ile Asn Ser Ser Pro Ala Val Pro Val
    290                 295                 300

Gln Asn Met Ser Thr Ala Ser Val Pro Leu Glu Pro Ala Thr Ala Thr
305                 310                 315                 320

Asp Ala Leu Ser Ser Met Glu Ala Leu Asn His Val
                325                 330
```

<210> SEQ ID NO 35

<400> SEQUENCE: 35

000

<210> SEQ ID NO 36

<400> SEQUENCE: 36

000

<210> SEQ ID NO 37
<211> LENGTH: 951
<212> TYPE: DNA
<213> ORGANISM: Aquimarina atlantica

<400> SEQUENCE: 37

| | | | | | |
|---|---|---|---|---|---|
| atgaaagacc | agctgctgac | cgttgctctg | gctcagatct | ctccggtttg | gctggacaaa | 60 |
| accgctacca | tcaaaaaaat | cgaaaactct | atcgctgaag | ctgcttctaa | aaaagctgaa | 120 |
| ctgatcgttt | tcggtgaatc | tctgctgccg | ggttacccgt | tctgggtttc | tctgaccgac | 180 |
| ggtgctaaat | tcgactctaa | aatccagaaa | gaaatccacg | ctcactacgc | tcagaactct | 240 |
| atcgttatcg | aaaacggtga | cctggacacc | atctgcgaac | tggctgctga | atgcaacatc | 300 |
| gctatctacc | tgggtatcat | cgaacgtccg | atcgaccgtg | tggtcactc | tctgtacgct | 360 |
| tctctggttt | acatcgacca | gaaaggtgaa | atcaaatctg | ttcaccgtaa | actgcagccg | 420 |
| acctacgaag | aacgtctgac | ctgggctccg | ggtgacggta | acggtctgct | ggttcacccg | 480 |
| ctgaaagctt | tcaccgttgg | tggtctgaac | tgctgggaaa | actggatgcc | gctgccgcgt | 540 |
| gctgctctgt | acggtcaggg | tgaaaacctg | cacatcgctg | tttggccggg | ttctgactac | 600 |
| aacaccaaag | acatcacccg | tttcatcgct | cgtgaatctc | gttcttacgt | tatctctgtt | 660 |
| tcttctctga | tgcgtaccga | agacttcccg | aaaaccaccc | cgcacctgga | cgaaatcctg | 720 |
| aaaaagctc | cggacgttct | gggtaacggt | ggttcttgca | tcgctggtcc | ggacggtgaa | 780 |
| tgggttatga | aaccggttct | gcacaaagaa | ggtctgctga | tcgaaaccct | ggacttctct | 840 |
| aaagttctgc | aggaacgtca | gaacttcgac | ccggttggtc | actactctcg | tccggacgtt | 900 |
| acccagctgc | acgttaaccg | taaacgtcag | tctaccgttc | gtttcgacga | a | 951 |

<210> SEQ ID NO 38
<211> LENGTH: 317
<212> TYPE: PRT
<213> ORGANISM: Aquimarina atlantica

<400> SEQUENCE: 38

Met Lys Asp Gln Leu Leu Thr Val Ala Leu Ala Gln Ile Ser Pro Val
1               5                   10                  15

Trp Leu Asp Lys Thr Ala Thr Ile Lys Lys Ile Glu Asn Ser Ile Ala
            20                  25                  30

Glu Ala Ala Ser Lys Lys Ala Glu Leu Ile Val Phe Gly Glu Ser Leu
        35                  40                  45

Leu Pro Gly Tyr Pro Phe Trp Val Ser Leu Thr Asp Gly Ala Lys Phe
    50                  55                  60

Asp Ser Lys Ile Gln Lys Glu Ile His Ala His Tyr Ala Gln Asn Ser
65                  70                  75                  80

Ile Val Ile Glu Asn Gly Asp Leu Asp Thr Ile Cys Glu Leu Ala Ala
                85                  90                  95

Glu Cys Asn Ile Ala Ile Tyr Leu Gly Ile Ile Glu Arg Pro Ile Asp

```
        100                 105                 110
Arg Gly Gly His Ser Leu Tyr Ala Ser Leu Val Tyr Ile Asp Gln Lys
            115                 120                 125

Gly Glu Ile Lys Ser Val His Arg Lys Leu Gln Pro Thr Tyr Glu Glu
        130                 135                 140

Arg Leu Thr Trp Ala Pro Gly Asp Gly Asn Gly Leu Leu Val His Pro
145                 150                 155                 160

Leu Lys Ala Phe Thr Val Gly Gly Leu Asn Cys Trp Glu Asn Trp Met
                165                 170                 175

Pro Leu Pro Arg Ala Ala Leu Tyr Gly Gln Gly Glu Asn Leu His Ile
            180                 185                 190

Ala Val Trp Pro Gly Ser Asp Tyr Asn Thr Lys Asp Ile Thr Arg Phe
        195                 200                 205

Ile Ala Arg Glu Ser Arg Ser Tyr Val Ile Ser Val Ser Ser Leu Met
    210                 215                 220

Arg Thr Glu Asp Phe Pro Lys Thr Thr Pro His Leu Asp Glu Ile Leu
225                 230                 235                 240

Lys Lys Ala Pro Asp Val Leu Gly Asn Gly Gly Ser Cys Ile Ala Gly
                245                 250                 255

Pro Asp Gly Glu Trp Val Met Lys Pro Val Leu His Lys Glu Gly Leu
            260                 265                 270

Leu Ile Glu Thr Leu Asp Phe Ser Lys Val Leu Gln Glu Arg Gln Asn
        275                 280                 285

Phe Asp Pro Val Gly His Tyr Ser Arg Pro Val Thr Gln Leu His
    290                 295                 300

Val Asn Arg Lys Arg Gln Ser Thr Val Arg Phe Asp Glu
305                 310                 315
```

<210> SEQ ID NO 39
<211> LENGTH: 945
<212> TYPE: DNA
<213> ORGANISM: Arthrobacter sp.
<220> FEATURE:
<223> OTHER INFORMATION: Arthrobacter sp. Soil736

<400> SEQUENCE: 39

```
atgcgtatcg ctgctatcca ggctaccccg gttatcctgg acgctgaagc ttctgtttct    60
aaagctctgc gtctgctggg tgaagctgct ggtcagggtg ttaaactggc tgttttcccg   120
gaaaccttca tcccgctgta cccgtctggt gtttgggctt accaggctgc tcgtttcgac   180
ggtttcgacg aaatgtggac ccgtctgtgg acaactctg ttgacgttcc gggtccgcag   240
atcgaccgtt tcatcaaagc ttgcgctgaa cacgacatct actgcgttct gggtgttaac   300
gaacgtgaat ctgctcgtcc gggttctctg tacaacacca tgatcctgct gggtccggaa   360
ggtctgctgt ggaaacaccg taaactgatg ccgaccatgc acgaacgtct gttccacggt   420
gttggttacg tcaggacct gaacgttatc gaaaccccgg ttggtcgtgt tggtggtctg   480
atctgctggg aaaaccgtat gccgctggct cgttacgctg tttaccgtca gggtgttcag   540
atctgggctg ctccgaccgc tgacgactct gacggttgga tctctaccat gtctcacatc   600
gctatcgaat ctggtgcttt cgttgttct gctccgcagt acatcccgcg ttctgctttc   660
ccggacgact tcccggttca gctgccggac gacggtcagg ctctgggtcg tggtggtgct   720
gctatcttcg aaccgctgca gggtcgtgct atcgctggtc cgctgtacga ccaggaaggt   780
atcgttgttg ctgacgttga cctgggtcgt tctctgaccg ctaaacgtat cttcgacgtt   840
```

-continued

```
gttggtcact actctcgtga agacgttctg tacccgccgg ctccgaccaa ccacgctccg    900
gaaggtccgg ctttctggcc gcgtacccgt ccgctgctgg gtaac                    945
```

<210> SEQ ID NO 40
<211> LENGTH: 315
<212> TYPE: PRT
<213> ORGANISM: Arthrobacter sp.
<220> FEATURE:
<223> OTHER INFORMATION: Arthrobacter sp. Soil736

<400> SEQUENCE: 40

| Met | Arg | Ile | Ala | Ala | Ile | Gln | Ala | Thr | Pro | Val | Ile | Leu | Asp | Ala | Glu |
|---|---|---|---|---|---|---|---|---|---|---|---|---|---|---|---|
| 1 | | | | 5 | | | | | 10 | | | | | 15 | |

Ala Ser Val Ser Lys Ala Leu Arg Leu Leu Gly Glu Ala Ala Gly Gln
            20                  25                  30

Gly Val Lys Leu Ala Val Phe Pro Glu Thr Phe Ile Pro Leu Tyr Pro
        35                  40                  45

Ser Gly Val Trp Ala Tyr Gln Ala Ala Arg Phe Asp Gly Phe Asp Glu
    50                  55                  60

Met Trp Thr Arg Leu Trp Asp Asn Ser Val Asp Val Pro Gly Pro Gln
65                  70                  75                  80

Ile Asp Arg Phe Ile Lys Ala Cys Ala Glu His Asp Ile Tyr Cys Val
                85                  90                  95

Leu Gly Val Asn Glu Arg Glu Ser Ala Arg Pro Gly Ser Leu Tyr Asn
            100                 105                 110

Thr Met Ile Leu Leu Gly Pro Glu Gly Leu Leu Trp Lys His Arg Lys
        115                 120                 125

Leu Met Pro Thr Met His Glu Arg Leu Phe His Gly Val Gly Tyr Gly
    130                 135                 140

Gln Asp Leu Asn Val Ile Glu Thr Pro Val Gly Arg Val Gly Gly Leu
145                 150                 155                 160

Ile Cys Trp Glu Asn Arg Met Pro Leu Ala Arg Tyr Ala Val Tyr Arg
                165                 170                 175

Gln Gly Val Gln Ile Trp Ala Ala Pro Thr Ala Asp Asp Ser Asp Gly
            180                 185                 190

Trp Ile Ser Thr Met Ser His Ile Ala Ile Glu Ser Gly Ala Phe Val
        195                 200                 205

Val Ser Ala Pro Gln Tyr Ile Pro Arg Ser Ala Phe Pro Asp Asp Phe
    210                 215                 220

Pro Val Gln Leu Pro Asp Asp Gly Gln Ala Leu Gly Arg Gly Gly Ala
225                 230                 235                 240

Ala Ile Phe Glu Pro Leu Gln Gly Arg Ala Ile Ala Gly Pro Leu Tyr
                245                 250                 255

Asp Gln Glu Gly Ile Val Val Ala Val Asp Leu Gly Arg Ser Leu
            260                 265                 270

Thr Ala Lys Arg Ile Phe Asp Val Val Gly His Tyr Ser Arg Glu Asp
        275                 280                 285

Val Leu Tyr Pro Pro Ala Pro Thr Asn His Ala Pro Glu Gly Pro Ala
    290                 295                 300

Phe Trp Pro Arg Thr Arg Pro Leu Leu Gly Asn
305                 310                 315

<210> SEQ ID NO 41
<211> LENGTH: 1020
<212> TYPE: DNA
<213> ORGANISM: Cupriavidus basilensis

<400> SEQUENCE: 41

```
atgtctcaga aacgtatcgt tcgtgctgct gctgttcaga tctctccgga cctggaacac    60
ggtgaaggta ccctgggtaa agtttgcgaa gctatcgacc gtgctgctcg tgaaggtgtt   120
cagctgatcg ttttcccgga aaccttcctg ccgtactacc cgtacttctc tttcgttcgt   180
ccgccggttc agtctggttc tgaccacatg cgtctgtacg aacaggctgt tgttgttccg   240
ggtccggtta cccacgctgt ttctgaacgt gctcgtcgtc acgctatggt tgttgttctg   300
ggtgttaacg aacgtgacca cggttctctg tacaacaccc agctgatctt cgacaccgac   360
ggtcgtctgt tctgaaacg tcgtaaaatc accccgacct tccacgaacg tatgatctgg   420
ggtcagggtg acgctgctgg tctgaaagtt gctgacaccg ctatcggtcg tgttggtgct   480
ctggcttgct gggaacacta caacccgctg gctcgttacg ctctgatgac ccagcacgaa   540
gaaatccact gctctcagtt cccgggttct ctggttggtc cggttttcgc tgaacagatc   600
gaagttacca tccgtcacca cgctctggaa tctggttgct cgttgttaa cgctaccggt   660
tggctgaccg acgaacagat cgcttctgtt accaccgacc cggctctgca gaaagctctg   720
cgtggtggtt gcaacaccgc tatcgtttct ccggaaggtc agcacctggc tccgccgctg   780
cgtgaaggtg aaggtatggt tatcgctgac ctggacatgt ctctgatcac caaacgtaaa   840
cgtatgatgg actctgttgg tcactacgct cgtccggaac tgctgtctct ggctatcaac   900
gaccgtccgg ctgctaccgc ttctccgatg gctaccgctc tgtctaacta ccacggttct   960
acccaccacg aaccgcagcg tgacgacgct ggtctggacc tggaaccggt tgttggtaac  1020
```

<210> SEQ ID NO 42
<211> LENGTH: 340
<212> TYPE: PRT
<213> ORGANISM: Cupriavidus basilensis

<400> SEQUENCE: 42

```
Met Ser Gln Lys Arg Ile Val Arg Ala Ala Ala Val Gln Ile Ser Pro
1               5                   10                  15

Asp Leu Glu His Gly Glu Gly Thr Leu Gly Lys Val Cys Glu Ala Ile
                20                  25                  30

Asp Arg Ala Ala Arg Glu Gly Val Gln Leu Ile Val Phe Pro Glu Thr
            35                  40                  45

Phe Leu Pro Tyr Tyr Pro Tyr Phe Ser Phe Val Arg Pro Val Gln
        50                  55                  60

Ser Gly Ser Asp His Met Arg Leu Tyr Glu Gln Ala Val Val Val Pro
65                  70                  75                  80

Gly Pro Val Thr His Ala Val Ser Glu Arg Ala Arg Arg His Ala Met
                85                  90                  95

Val Val Val Leu Gly Val Asn Glu Arg Asp His Gly Ser Leu Tyr Asn
                100                 105                 110

Thr Gln Leu Ile Phe Asp Thr Asp Gly Arg Leu Val Leu Lys Arg Arg
            115                 120                 125

Lys Ile Thr Pro Thr Phe His Glu Arg Met Ile Trp Gly Gln Gly Asp
        130                 135                 140

Ala Ala Gly Leu Lys Val Ala Asp Thr Ala Ile Gly Arg Val Gly Ala
145                 150                 155                 160

Leu Ala Cys Trp Glu His Tyr Asn Pro Leu Ala Arg Tyr Ala Leu Met
                165                 170                 175

Thr Gln His Glu Glu Ile His Cys Ser Gln Phe Pro Gly Ser Leu Val
```

180                 185                 190
Gly Pro Val Phe Ala Glu Gln Ile Glu Val Thr Ile Arg His His Ala
            195                 200                 205
Leu Glu Ser Gly Cys Phe Val Val Asn Ala Thr Gly Trp Leu Thr Asp
        210                 215                 220
Glu Gln Ile Ala Ser Val Thr Thr Asp Pro Ala Leu Gln Lys Ala Leu
225                 230                 235                 240
Arg Gly Gly Cys Asn Thr Ala Ile Val Ser Pro Glu Gly Gln His Leu
                245                 250                 255
Ala Pro Pro Leu Arg Glu Gly Glu Met Val Ile Ala Asp Leu Asp
            260                 265                 270
Met Ser Leu Ile Thr Lys Arg Lys Arg Met Met Asp Ser Val Gly His
        275                 280                 285
Tyr Ala Arg Pro Glu Leu Leu Ser Leu Ala Ile Asn Asp Arg Pro Ala
            290                 295                 300
Ala Thr Ala Ser Pro Met Ala Thr Ala Leu Ser Asn Tyr His Gly Ser
305                 310                 315                 320
Thr His His Glu Pro Gln Arg Asp Asp Ala Gly Leu Asp Leu Glu Pro
                325                 330                 335
Val Val Gly Asn
            340

<210> SEQ ID NO 43

<400> SEQUENCE: 43

000

<210> SEQ ID NO 44

<400> SEQUENCE: 44

000

<210> SEQ ID NO 45
<211> LENGTH: 1059
<212> TYPE: DNA
<213> ORGANISM: Sphingomonas wittichii
<220> FEATURE:
<223> OTHER INFORMATION: Sphingomonas wittichii RW1

<400> SEQUENCE: 45
atgaacgaag gtttccagaa agttcgtgtt gctgctgctc agatctctcc ggctttcctg      60
gaccgtgaag ttctaccga atcgcttgc cactggatcg ctgaagctgc tcgtggtggt      120
gctgaactgc tgtcttcgg tgaagcttgg ctgccggctt accgttctg gatcttcatg      180 ggttctccga tctactctgc tcagttctct cgtcgtctgt acgaaaacgc tgttgaaatc      240
ccgtctgcta ccaccgaccg tctgtgcgaa gctgctcgta agctggtat ccacgttgtt      300 atgggtctga ccgaactgtg gggtggttct ctgtacctgg ctcagctgtt catcaacgac      360
cgtggtgaaa tcgttggtca ccgtcgtaaa ctgaaaccga cccactggga acgtgctatc      420
tggggtgaag tgacggttc tgacttcttc gttgttccga cctctatcgg tcgtctgggt      480
gctctgaact gctgggaaca cctgcagccg ctgaacctgt tcgctatgaa cgctttcggt      540
gaacagatcc acgttgctgc ttggccggct tcgctatct acaaccgtgt tgacccgtct      600
ttcaccaacg aagctaacct ggctgctct cgtgcttacg ctatggctac ccagaccttc      660
gttatccaca cctctgctgt tgttgacgac gctaccgttg aactgctgtg cgacgacgac      720

```
gacaaacgtc tgctgctgga atctggtggt ggtcagtgcg ctgttatcaa cccgctgggt      780
gctatcatct ctaccccgct gtcttctacc gctcagggtc tggttttcgc tgactgcgac      840
ttcggtgtta tcgcttctgc taaaatgtct aacgacccgg ctggtcacta ccagcgtggt      900
gacgttttcc aggttcactt caacccggct ccgcgtcgtc cgctggttcc gcgtgctgct      960
atcgctgctg acccgaccac cgctgcttct gaagacctgc gaacatcaa acacccgccg     1020 ttctctccgg ctgttaaact gccgatcgtt gttgacgac                            1059
```

<210> SEQ ID NO 46
<211> LENGTH: 353
<212> TYPE: PRT
<213> ORGANISM: Sphingomonas wittichii
<220> FEATURE:
<223> OTHER INFORMATION: Sphingomonas wittichii RW1

<400> SEQUENCE: 46

```
Met Asn Glu Gly Phe Gln Lys Val Arg Val Ala Ala Gln Ile Ser
1               5                   10                  15

Pro Ala Phe Leu Asp Arg Glu Gly Ser Thr Glu Ile Ala Cys His Trp
                20                  25                  30

Ile Ala Glu Ala Ala Arg Gly Gly Ala Glu Leu Leu Ser Phe Gly Glu
            35                  40                  45

Ala Trp Leu Pro Ala Tyr Pro Phe Trp Ile Phe Met Gly Ser Pro Ile
        50                  55                  60

Tyr Ser Ala Gln Phe Ser Arg Arg Leu Tyr Glu Asn Ala Val Glu Ile
65                  70                  75                  80

Pro Ser Ala Thr Thr Asp Arg Leu Cys Glu Ala Ala Arg Lys Ala Gly
                85                  90                  95

Ile His Val Val Met Gly Leu Thr Glu Leu Trp Gly Gly Ser Leu Tyr
            100                 105                 110

Leu Ala Gln Leu Phe Ile Asn Asp Arg Gly Glu Ile Val Gly His Arg
        115                 120                 125

Arg Lys Leu Lys Pro Thr His Trp Glu Arg Ala Ile Trp Gly Glu Gly
130                 135                 140

Asp Gly Ser Asp Phe Phe Val Val Pro Thr Ser Ile Gly Arg Leu Gly
145                 150                 155                 160

Ala Leu Asn Cys Trp Glu His Leu Gln Pro Leu Asn Leu Phe Ala Met
                165                 170                 175

Asn Ala Phe Gly Glu Gln Ile His Val Ala Ala Trp Pro Ala Phe Ala
            180                 185                 190

Ile Tyr Asn Arg Val Asp Pro Ser Phe Thr Asn Glu Ala Asn Leu Ala
        195                 200                 205

Ala Ser Arg Ala Tyr Ala Met Ala Thr Gln Thr Phe Val Ile His Thr
    210                 215                 220

Ser Ala Val Val Asp Asp Ala Thr Val Glu Leu Leu Cys Asp Asp
225                 230                 235                 240

Asp Lys Arg Leu Leu Leu Glu Ser Gly Gly Gly Gln Cys Ala Val Ile
                245                 250                 255

Asn Pro Leu Gly Ala Ile Ile Ser Thr Pro Leu Ser Ser Thr Ala Gln
            260                 265                 270

Gly Leu Val Phe Ala Asp Cys Asp Phe Gly Val Ile Ala Ser Ala Lys
        275                 280                 285

Met Ser Asn Asp Pro Ala Gly His Tyr Gln Arg Gly Asp Val Phe Gln
    290                 295                 300
```

Val His Phe Asn Pro Ala Pro Arg Arg Pro Leu Val Pro Arg Ala Ala
305                 310                 315                 320

Ile Ala Ala Asp Pro Thr Thr Ala Ala Ser Glu Asp Leu Pro Asn Ile
                325                 330                 335

Lys His Pro Pro Phe Ser Pro Ala Val Lys Leu Pro Ile Val Val Asp
                340                 345                 350

Asp

<210> SEQ ID NO 47
<211> LENGTH: 951
<212> TYPE: DNA
<213> ORGANISM: Pseudomonas mandelii
<220> FEATURE:
<223> OTHER INFORMATION: Pseudomonas mandelii JR-1

<400> SEQUENCE: 47
atggaaaacg ctatgaccaa agttgctatc atccagcgtc cgccggttct gctggaccgt         60
tctgctacca tcgctcgtgc tgttcagtct gttgctgaag ctgctgctgc tggtgcttct        120
ctgatcgttc tgccggaatc tttcatcccg ggttacccgt cttggatctg gcgtctggct        180
gctggtaaag acggtgctgt tatgggtcag ctgcacaccc gtctgctggc taacgctgtt        240
gacatcgcta acggtgacct gggtgaactg tgcgaagctg ctcgtgttca cgctgttacc        300
atcgtttgcg gtatcaacga atgcgaccgt tctaccggtg tggtaccct gtacaactct         360 gttgttgtta tcggtgctga cggtgctgtt ctgaaccgtc accgtaaact gatgccgacc        420
aacccggaac gtatggttca cggtttcggt gacgcttctg gtctgcgtgc tgttgacacc        480
ccggttggtc gtgttggtgc tctgatctgc tgggaaaaact acatgccgct ggctcgttac        540
tctctgtacg ctcagggtgt tgaaatctac atcgctccga cctacgacac cggtgaaggt        600
tggatctcta ccatgcgtca catcgctctg gaaggtcgtt gctgggttct gggttctggt        660
accgctctgc gtggttctga catcccggaa gacttcccgg ctcgtatgca gctgttcgct        720
gacccggacg aatggatcaa cgacggtgac tctgttgttg tttctccgca gggtcgtgtt        780
gttgctggtc cgctgcaccg tgaagctggt atcctgtacg ctgacatcga cgttgctctg        840
gttgctccgg ctcgtcgtgc tctggacgtt accggtcact acgctcgtcc ggacatcttc        900
gaactgcacg ttcgtcgttc tccggctatc ccggttcact acatcgacga a                951

<210> SEQ ID NO 48
<211> LENGTH: 317
<212> TYPE: PRT
<213> ORGANISM: Pseudomonas mandelii
<220> FEATURE:
<223> OTHER INFORMATION: Pseudomonas mandelii JR-1

<400> SEQUENCE: 48

Met Glu Asn Ala Met Thr Lys Val Ala Ile Ile Gln Arg Pro Pro Val
1               5                   10                  15

Leu Leu Asp Arg Ser Ala Thr Ile Ala Arg Ala Val Gln Ser Val Ala
                20                  25                  30

Glu Ala Ala Ala Ala Gly Ala Ser Leu Ile Val Leu Pro Glu Ser Phe
            35                  40                  45

Ile Pro Gly Tyr Pro Ser Trp Ile Trp Arg Leu Ala Ala Gly Lys Asp
        50                  55                  60

Gly Ala Val Met Gly Gln Leu His Thr Arg Leu Leu Ala Asn Ala Val
65                  70                  75                  80

Asp Ile Ala Asn Gly Asp Leu Gly Glu Leu Cys Glu Ala Ala Arg Val
                85                  90                  95

His Ala Val Thr Ile Val Cys Gly Ile Asn Glu Cys Asp Arg Ser Thr
            100                 105                 110

Gly Gly Gly Thr Leu Tyr Asn Ser Val Val Ile Gly Ala Asp Gly
        115                 120                 125

Ala Val Leu Asn Arg His Arg Lys Leu Met Pro Thr Asn Pro Glu Arg
    130                 135                 140

Met Val His Gly Phe Gly Asp Ala Ser Gly Leu Arg Ala Val Asp Thr
145                 150                 155                 160

Pro Val Gly Arg Val Gly Ala Leu Ile Cys Trp Glu Asn Tyr Met Pro
                165                 170                 175

Leu Ala Arg Tyr Ser Leu Tyr Ala Gln Gly Val Glu Ile Tyr Ile Ala
            180                 185                 190

Pro Thr Tyr Asp Thr Gly Glu Gly Trp Ile Ser Thr Met Arg His Ile
        195                 200                 205

Ala Leu Glu Gly Arg Cys Trp Val Leu Gly Ser Gly Thr Ala Leu Arg
    210                 215                 220

Gly Ser Asp Ile Pro Glu Asp Phe Pro Ala Arg Met Gln Leu Phe Ala
225                 230                 235                 240

Asp Pro Asp Glu Trp Ile Asn Asp Gly Asp Ser Val Val Ser Pro
                245                 250                 255

Gln Gly Arg Val Val Ala Gly Pro Leu His Arg Glu Ala Gly Ile Leu
            260                 265                 270

Tyr Ala Asp Ile Asp Val Ala Leu Val Ala Pro Ala Arg Arg Ala Leu
        275                 280                 285

Asp Val Thr Gly His Tyr Ala Arg Pro Asp Ile Phe Glu Leu His Val
    290                 295                 300

Arg Arg Ser Pro Ala Ile Pro Val His Tyr Ile Asp Glu
305                 310                 315

<210> SEQ ID NO 49

<400> SEQUENCE: 49

000

<210> SEQ ID NO 50

<400> SEQUENCE: 50

000

<210> SEQ ID NO 51
<211> LENGTH: 1017
<212> TYPE: DNA
<213> ORGANISM: Arabidopsis thaliana

<400> SEQUENCE: 51
atgtctacct ctgaaaacac cccgttcaac ggtgttgctt cttctaccat cgttcgtgct    60
accatcgttc aggcttctac cgtttacaac gacaccccgg ctaccctgga aaaagctaac    120
aaattcatcg ttgaagctgc ttctaaaggt tctgaactgg ttgttttccc ggaagctttc    180
atcggtggtt acccgcgtgg tttccgtttc ggtctgggtg ttggtgttca acgaagaa    240 ggtcgtgacg aattccgtaa ataccacgct tctgctatca agttccgggt tccggaagtt    300
gaaaaactgg ctgaactggc tggtaaaaac aacgtttacc tggttatggg tgctatcgaa    360

```
aaagacggtt acaccctgta ctgcaccgct ctgttcttct ctccgcaggg tcagttcctg    420
ggtaaacacc gtaaactgat gccgacctct ctggaacgtt gcatctgggg tcagggtgac    480
ggttctacca tcccggttta cgacaccccg atcggtaaac tgggtgctgc tatctgctgg    540
gaaaaccgta tgccgctgta ccgtaccgct ctgtacgcta aggtatcga actgtactgc    600 gctccgaccg ctgacggttc taagaatgg cagtcttcta tgctgcacat cgctatcgaa    660
ggtggttgct cgttctgtc tgcttgccag ttctgcctgc gtaaagactt cccggaccac    720
ccggactacc tgttcaccga ctggtacgac gacaaagaac cggactctat cgtttctcag    780
ggtggttctg ttatcatctc tccgctgggt caggttctgg ctggtccgaa cttcgaatct    840
gaaggtctga tcaccgctga cctggacctg ggtgacgttg ctcgtgctaa actgtacttc    900
gactctgttg gtcactactc tcgtccggac gttctgcacc tgaccgttaa cgaacacccg    960
aaaaaaccgg ttaccttcat ctctaaagtt gaaaagctg aagacgactc taacaaa       1017
```

<210> SEQ ID NO 52
<211> LENGTH: 339
<212> TYPE: PRT
<213> ORGANISM: Arabidopsis thaliana

<400> SEQUENCE: 52

```
Met Ser Thr Ser Glu Asn Thr Pro Phe Asn Gly Val Ala Ser Ser Thr
1               5                   10                  15

Ile Val Arg Ala Thr Ile Val Gln Ala Ser Thr Val Tyr Asn Asp Thr
            20                  25                  30

Pro Ala Thr Leu Glu Lys Ala Asn Lys Phe Ile Val Glu Ala Ala Ser
        35                  40                  45

Lys Gly Ser Glu Leu Val Val Phe Pro Glu Ala Phe Ile Gly Gly Tyr
    50                  55                  60

Pro Arg Gly Phe Arg Phe Gly Leu Gly Val Gly Val His Asn Glu Glu
65                  70                  75                  80

Gly Arg Asp Glu Phe Arg Lys Tyr His Ala Ser Ala Ile Lys Val Pro
                85                  90                  95

Gly Pro Glu Val Glu Lys Leu Ala Glu Leu Ala Gly Lys Asn Asn Val
            100                 105                 110

Tyr Leu Val Met Gly Ala Ile Glu Lys Asp Gly Tyr Thr Leu Tyr Cys
        115                 120                 125

Thr Ala Leu Phe Phe Ser Pro Gln Gly Gln Phe Leu Gly Lys His Arg
    130                 135                 140

Lys Leu Met Pro Thr Ser Leu Glu Arg Cys Ile Trp Gly Gln Gly Asp
145                 150                 155                 160

Gly Ser Thr Ile Pro Val Tyr Asp Thr Pro Ile Gly Lys Leu Gly Ala
                165                 170                 175

Ala Ile Cys Trp Glu Asn Arg Met Pro Leu Tyr Arg Thr Ala Leu Tyr
            180                 185                 190

Ala Lys Gly Ile Glu Leu Tyr Cys Ala Pro Thr Ala Asp Gly Ser Lys
        195                 200                 205

Glu Trp Gln Ser Ser Met Leu His Ile Ala Ile Glu Gly Gly Cys Phe
    210                 215                 220

Val Leu Ser Ala Cys Gln Phe Cys Leu Arg Lys Asp Phe Pro Asp His
225                 230                 235                 240

Pro Asp Tyr Leu Phe Thr Asp Trp Tyr Asp Asp Lys Glu Pro Asp Ser
                245                 250                 255

Ile Val Ser Gln Gly Gly Ser Val Ile Ile Ser Pro Leu Gly Gln Val
```

```
                260                265                270
Leu Ala Gly Pro Asn Phe Glu Ser Glu Gly Leu Ile Thr Ala Asp Leu
            275                280                285

Asp Leu Gly Asp Val Ala Arg Ala Lys Leu Tyr Phe Asp Ser Val Gly
        290                295                300

His Tyr Ser Arg Pro Asp Val Leu His Leu Thr Val Asn Glu His Pro
305                310                315                320

Lys Lys Pro Val Thr Phe Ile Ser Lys Val Glu Lys Ala Glu Asp Asp
                325                330                335

Ser Asn Lys

<210> SEQ ID NO 53
<211> LENGTH: 1029
<212> TYPE: DNA
<213> ORGANISM: Brassica oleracea

<400> SEQUENCE: 53
atgtctaccc cgaaaaacac cacccaggct aacggtgact cttcttcttc tatcgttcgt      60
gctaccatcg ttcaggcttc taccgtttac aacgacaccc cgaaaaccat cgaaaaagct     120
gaaaaactga tcgctgaagc tgcttctaac ggttctgaac tggttgtttt cccggaaggt     180
ttcatcggtg gttacccgcg tggtttccgt ttcggtatcg ctgttggtat ccacaacgaa     240
gacggtcgtg acgacttccg taaataccac gactctgcta ccacgttcc gggtccggaa      300 gttgacaaac tggctgaact ggctcgtaaa aacaacgttt acctggttat gggtgctatc     360
gaaaaagacg ttacaccct gtactgcacc gctctgttct tcaactctga aggtcgttac      420
ctgggtaaac accgtaaagt tatgccgacc tctctggaac gttgcatctg gggtttcggt     480
gacggttcta ccatcccggt ttacgacacc ccgatcggta aactgggtgc tgctatctgc     540
tgggaaaaac cgtatgccgct gtaccgtacc gctctgtacg gtaaaggtgt tgaactgtac     600
tgcgctccga ccgctgacgg ttctaaagaa tggcagtctt ctatgatgca catcgctatg     660
gaaggtggtt gcttcgttct gtctgcttgc cagttctgcc agcgtaaaga cttcccggct     720
cacgttgacc acctgttcac cgactggtac gacgaccagc acgacgaagc tatcgttct      780 cagggtggtt ctgttatcat ctctccgctg gtaaagttc tggctggtcc gaacttcgaa      840
tctgaaggtc tgatcaccgc tgacctggac ctgggtgaca tcgctcgtgc taaactgtac     900
ttcgacgttg ttggtcacta ctctaaaccg gacgttttca acctgaccgt taacgaacac     960
ccgaaaaaac cggttacctt cgtttctaaa accgttaaag ctgaagacgg ttctgaatct    1020
aaagaaaaa                                                            1029

<210> SEQ ID NO 54
<211> LENGTH: 343
<212> TYPE: PRT
<213> ORGANISM: Brassica oleracea

<400> SEQUENCE: 54

Met Ser Thr Pro Lys Asn Thr Thr Gln Ala Asn Gly Asp Ser Ser Ser
1               5                  10                  15

Ser Ile Val Arg Ala Thr Ile Val Gln Ala Ser Thr Val Tyr Asn Asp
            20                  25                  30

Thr Pro Lys Thr Ile Glu Lys Ala Glu Lys Leu Ile Ala Glu Ala Ala
        35                  40                  45

Ser Asn Gly Ser Glu Leu Val Val Phe Pro Glu Gly Phe Ile Gly Gly
    50                  55                  60
```

Tyr Pro Arg Gly Phe Arg Phe Gly Ile Ala Val Gly Ile His Asn Glu
65                  70                  75                  80

Asp Gly Arg Asp Asp Phe Arg Lys Tyr His Asp Ser Ala Ile His Val
                85                  90                  95

Pro Gly Pro Glu Val Asp Lys Leu Ala Glu Leu Ala Arg Lys Asn Asn
            100                 105                 110

Val Tyr Leu Val Met Gly Ala Ile Glu Lys Asp Gly Tyr Thr Leu Tyr
            115                 120                 125

Cys Thr Ala Leu Phe Phe Asn Ser Glu Gly Arg Tyr Leu Gly Lys His
130                 135                 140

Arg Lys Val Met Pro Thr Ser Leu Glu Arg Cys Ile Trp Gly Phe Gly
145                 150                 155                 160

Asp Gly Ser Thr Ile Pro Val Tyr Asp Thr Pro Ile Gly Lys Leu Gly
                165                 170                 175

Ala Ala Ile Cys Trp Glu Asn Arg Met Pro Leu Tyr Arg Thr Ala Leu
            180                 185                 190

Tyr Gly Lys Gly Val Glu Leu Tyr Cys Ala Pro Thr Ala Asp Gly Ser
            195                 200                 205

Lys Glu Trp Gln Ser Ser Met Met His Ile Ala Met Glu Gly Gly Cys
210                 215                 220

Phe Val Leu Ser Ala Cys Gln Phe Cys Gln Arg Lys Asp Phe Pro Ala
225                 230                 235                 240

His Val Asp His Leu Phe Thr Asp Trp Tyr Asp Gln His Asp Glu
                245                 250                 255

Ala Ile Val Ser Gln Gly Gly Ser Val Ile Ser Pro Leu Gly Lys
            260                 265                 270

Val Leu Ala Gly Pro Asn Phe Glu Ser Glu Gly Leu Ile Thr Ala Asp
            275                 280                 285

Leu Asp Leu Gly Asp Ile Ala Arg Ala Lys Leu Tyr Phe Asp Val Val
290                 295                 300

Gly His Tyr Ser Lys Pro Asp Val Phe Asn Leu Thr Val Asn Glu His
305                 310                 315                 320

Pro Lys Lys Pro Val Thr Phe Val Ser Lys Thr Val Lys Ala Glu Asp
                325                 330                 335

Gly Ser Glu Ser Lys Glu Lys
            340

<210> SEQ ID NO 55
<211> LENGTH: 1035
<212> TYPE: DNA
<213> ORGANISM: Salinisphaera shabanensis
<220> FEATURE:
<223> OTHER INFORMATION: Salinisphaera shabanensis E1L3A

<400> SEQUENCE: 55
atgacccagt ctcagatcgt taaagttgct gctgttcagc tgcagccggt tctggactct      60
gctgacggta ccgttgaacg tgttctggac gaaatcgctg ctgctgctgc tgacggtgct     120
cagctggttg ttttcccgga aaccgctgtt ccgtactacc gtactggtc tttcgttatg      180 gctccgatgg acatgggtgc tcgtcaccgt gctctgtacg accactctcc gaccgttccg     240
ggtccggtta ccgacgctgt tgctgctgct gctcgtaccc acgaaatcgt tgttgttctg     300
ggtgttaacg aacgtgacca cggtaccctg tacaactgcc agctggtttt cgacggtaac     360
ggtgaaatcg ctctgaaacg tcgtaaaatc accccgacct accacgaacg tatggtttgg     420

```
ggtcagggtg acggttctgg tctgcacgct gttgacaccg ctgttggtcg tgttggtgct    480
ctggcttgct gggaacacta caacccgctg gctcgttacg ctctgatggc tgaccacgaa    540
cagatccact gctctcagtt cccgggttct ctggttggtc cgatcttcgc tgaacagcag    600
gaagttaccc tgcgtcacca cgctctggaa tctggttgct cgttgttaa cgctaccgct     660 tggctggacg ctgaccaggt tgcttctgtt accgaagacc cggctctgca gaaaggtctg    720
ttcggtggtt gctacaccgc tatcatcgct ccggacggtt ctcacgttgt tgctccgctg    780
ctggacggtc cgggtcgtct ggttgctgac atcgacctgt ctctgatcac caaacgtaaa    840
cgtatgatgg actctgttgg tcactacgct cgtccggaac tgctgtctct gcgtatcgac    900
cgtcgttctc acgctgctca gcacgctgac gctgctccgg gtgttggtgc tgtttctgaa    960
ttcgaagaac cggaccacgg tgaaccggaa ccgtacgctg cttaccgtga cgctatcgct   1020
cgttcttcta ccggt                                                    1035
```

<210> SEQ ID NO 56
<211> LENGTH: 345
<212> TYPE: PRT
<213> ORGANISM: Salinisphaera shabanensis
<220> FEATURE:
<223> OTHER INFORMATION: Salinisphaera shabanensis E1L3A

<400> SEQUENCE: 56

```
Met Thr Gln Ser Gln Ile Val Lys Val Ala Ala Val Gln Leu Gln Pro
1               5                   10                  15

Val Leu Asp Ser Ala Asp Gly Thr Val Glu Arg Val Leu Asp Glu Ile
            20                  25                  30

Ala Ala Ala Ala Asp Gly Ala Gln Leu Val Val Phe Pro Glu Thr
        35                  40                  45

Ala Val Pro Tyr Tyr Pro Tyr Trp Ser Phe Val Met Ala Pro Met Asp
    50                  55                  60

Met Gly Ala Arg His Arg Ala Leu Tyr Asp His Ser Pro Thr Val Pro
65                  70                  75                  80

Gly Pro Val Thr Asp Ala Val Ala Ala Ala Arg Thr His Glu Ile
                85                  90                  95

Val Val Val Leu Gly Val Asn Glu Arg Asp His Gly Thr Leu Tyr Asn
                100                 105                 110

Cys Gln Leu Val Phe Asp Gly Asn Gly Glu Ile Ala Leu Lys Arg Arg
            115                 120                 125

Lys Ile Thr Pro Thr Tyr His Glu Arg Met Val Trp Gly Gln Gly Asp
    130                 135                 140

Gly Ser Gly Leu His Ala Val Asp Thr Ala Val Gly Arg Val Gly Ala
145                 150                 155                 160

Leu Ala Cys Trp Glu His Tyr Asn Pro Leu Ala Arg Tyr Ala Leu Met
                165                 170                 175

Ala Asp His Glu Gln Ile His Cys Ser Gln Phe Pro Gly Ser Leu Val
                180                 185                 190

Gly Pro Ile Phe Ala Glu Gln Gln Glu Val Thr Leu Arg His His Ala
            195                 200                 205

Leu Glu Ser Gly Cys Phe Val Val Asn Ala Thr Ala Trp Leu Asp Ala
    210                 215                 220

Asp Gln Val Ala Ser Val Thr Glu Asp Pro Ala Leu Gln Lys Gly Leu
225                 230                 235                 240

Phe Gly Gly Cys Tyr Thr Ala Ile Ile Ala Pro Asp Gly Ser His Val
                245                 250                 255
```

Val Ala Pro Leu Leu Asp Gly Pro Gly Arg Leu Val Ala Asp Ile Asp
            260                 265                 270

Leu Ser Leu Ile Thr Lys Arg Lys Arg Met Met Asp Ser Val Gly His
        275                 280                 285

Tyr Ala Arg Pro Glu Leu Leu Ser Leu Arg Ile Asp Arg Arg Ser His
        290                 295                 300

Ala Ala Gln His Ala Asp Ala Ala Pro Gly Val Gly Ala Val Ser Glu
305                 310                 315                 320

Phe Glu Glu Pro Asp His Gly Glu Pro Glu Pro Tyr Ala Ala Tyr Arg
                325                 330                 335

Asp Ala Ile Ala Arg Ser Ser Thr Gly
            340                 345

<210> SEQ ID NO 57

<400> SEQUENCE: 57

000

<210> SEQ ID NO 58

<400> SEQUENCE: 58

000

<210> SEQ ID NO 59
<211> LENGTH: 954
<212> TYPE: DNA
<213> ORGANISM: Smithella sp.
<220> FEATURE:
<223> OTHER INFORMATION: Smithella sp. SDB

<400> SEQUENCE: 59

```
atgaaaaacc agaccaaagt tgctgctatc cagctggcta ccaaaatcgg tgactctaac      60
accaacatcg ctggttgcga acgtctggct ctgatggcta tcaaaaacgg tgctcgttgg     120
atcgctctgc cggaattctt caccaccggt gtttcttgga accggaaat cgcttcttct     180
atccagaccg ttgacggtgc tgctgcttct ttcatgtgcg acttctctgc taaacaccag     240
gttgttctgg gtggttcttt cctgtgccgt ctgtctgacg ttctgttcg taaccgttac     300
cagtgctacg ctaacggttc tctgatcggt cagcacgaca agacctgcc gaccatgtgg     360
gaaaactact tctacgaagg tggtgacccg atggactctg tgttctggg tacctacaac     420
aacatccgta tcggtgctgc tgtttgctgg gaattcatgc gtaccatgac cgctcgtcgt     480
ctgcgtaaca agttgacgt tatcatcggt ggttcttgct ggtggtctat cccgaccaac     540
ttcccggttt tcctgcagaa actgtgggaa ccggctaacc actactgctc tctggctgct     600
atccaggact ctgctcgtct gatcggtgct ccggttatcc acgctgctca ctgcggtgaa     660
atcgaatgcc cgatgccggg tctgccgatc aaataccgtg ttacttcga aggtaacgct     720
tctatcgttg acgcttctgg taaagttctg gctcagcgtt ctgctgaaca gggtgaaggt     780
atcgtttgcg ctgacatcct gctggaagct cagccgacca tcgaagctat cccggaccgt     840
ttctggctgc gttctcgtgg tttcctgccg accttcgctt ggcaccacca gcgttggctg     900
ggtcgtcgtt ggtacaaacg taacgttcgt cagaaaaaaa acgaactgca ccac           954
```

<210> SEQ ID NO 60
<211> LENGTH: 318
<212> TYPE: PRT

<213> ORGANISM: Smithella sp.
<220> FEATURE:
<223> OTHER INFORMATION: Smithella sp. SDB

<400> SEQUENCE: 60

```
Met Lys Asn Gln Thr Lys Val Ala Ala Ile Gln Leu Ala Thr Lys Ile
1               5                   10                  15
Gly Asp Ser Asn Thr Asn Ile Ala Gly Cys Glu Arg Leu Ala Leu Met
            20                  25                  30
Ala Ile Lys Asn Gly Ala Arg Trp Ile Ala Leu Pro Glu Phe Phe Thr
        35                  40                  45
Thr Gly Val Ser Trp Lys Pro Glu Ile Ala Ser Ser Ile Gln Thr Val
    50                  55                  60
Asp Gly Ala Ala Ala Ser Phe Met Cys Asp Phe Ser Ala Lys His Gln
65                  70                  75                  80
Val Val Leu Gly Gly Ser Phe Leu Cys Arg Leu Ser Asp Gly Ser Val
                85                  90                  95
Arg Asn Arg Tyr Gln Cys Tyr Ala Asn Gly Ser Leu Ile Gly Gln His
            100                 105                 110
Asp Lys Asp Leu Pro Thr Met Trp Glu Asn Tyr Phe Tyr Glu Gly Gly
        115                 120                 125
Asp Pro Met Asp Ser Gly Val Leu Gly Thr Tyr Asn Asn Ile Arg Ile
    130                 135                 140
Gly Ala Ala Val Cys Trp Glu Phe Met Arg Thr Met Thr Ala Arg Arg
145                 150                 155                 160
Leu Arg Asn Lys Val Asp Val Ile Ile Gly Gly Ser Cys Trp Trp Ser
                165                 170                 175
Ile Pro Thr Asn Phe Pro Val Phe Leu Gln Lys Leu Trp Glu Pro Ala
            180                 185                 190
Asn His Tyr Cys Ser Leu Ala Ala Ile Gln Asp Ser Ala Arg Leu Ile
        195                 200                 205
Gly Ala Pro Val Ile His Ala His Cys Gly Glu Ile Glu Cys Pro
    210                 215                 220
Met Pro Gly Leu Pro Ile Lys Tyr Arg Gly Tyr Phe Glu Gly Asn Ala
225                 230                 235                 240
Ser Ile Val Asp Ala Ser Gly Lys Val Leu Ala Gln Arg Ser Ala Glu
                245                 250                 255
Gln Gly Glu Gly Ile Val Cys Ala Asp Ile Leu Leu Glu Ala Gln Pro
            260                 265                 270
Thr Ile Glu Ala Ile Pro Asp Arg Phe Trp Leu Arg Ser Arg Gly Phe
        275                 280                 285
Leu Pro Thr Phe Ala Trp His His Gln Arg Trp Leu Gly Arg Arg Trp
    290                 295                 300
Tyr Lys Arg Asn Val Arg Gln Lys Lys Asn Glu Leu His His
305                 310                 315
```

<210> SEQ ID NO 61
<211> LENGTH: 963
<212> TYPE: DNA
<213> ORGANISM: Bradyrhizobium diazoefficiens

<400> SEQUENCE: 61

```
atgatggata gtaaccgccc gaatacctat aaagcagccg tggtgcaggc agccagcgat      60
ccgaccagca gcctggttag tgcacagaaa gccgcagccc tgattgaaaa agccgccggt     120
gcaggtgcac gtctggttgt gtttccggaa gcctttattg gtggttatcc gaaaggtaat     180
```

```
agctttggtg ccccggtggg catgcgtaaa ccggaaggtc gtgaagcatt tcgtctgtat      240
tgggaagcag caattgatct ggatggcgtt gaagtggaaa ccattgccgc agcagcagca      300
gcgaccggtg cctttaccgt tattggctgt attgaacgtg aacagggcac cctgtattgc      360
accgcactgt ttttcgatgg cgcccgtggt ctggttggta acatcgtaa actgatgccg       420 accgccggcg aacgcctgat ttggggcttt ggtgacggta gcaccatgcc ggtgtttgaa      480
accagtctgg gtaatattgg cgcagttatt tgctgggaaa attatatgcc gatgctgcgc      540
atgcacatgt atagtcaggg cattagtatc tattgtgccc cgaccgcaga tgatcgtgat      600
acctggctgc cgaccatgca gcatattgca ctggaaggcc gctgctttgt tctgaccgcc      660
tgccagcatc tgaaacgtgg cgcatttccg ccgattatg aatgcgcact gggcgcagat       720
ccggaaaccg tgctgatgcg cggtggtagt gcaattgtga atccgctggg taaagttctg      780
gccggcccgt gctttgaagg cgaaaccatt ctgtatgcag atattgcact ggatgaagtt      840
acccgtggta aatttgattt tgatgcagca ggccattata gtcgtccgga tgtgtttcag      900
ctggttgtgg atgatcgtcc gaaacgcgcc gttagcaccg tgagcgccgt gcgtgcccgc      960
aat                                                                    963

<210> SEQ ID NO 62
<211> LENGTH: 321
<212> TYPE: PRT
<213> ORGANISM: Bradyrhizobium diazoefficiens

<400> SEQUENCE: 62

Met Met Asp Ser Asn Arg Pro Asn Thr Tyr Lys Ala Ala Val Val Gln
1               5                   10                  15

Ala Ala Ser Asp Pro Thr Ser Ser Leu Val Ser Ala Gln Lys Ala Ala
            20                  25                  30

Ala Leu Ile Glu Lys Ala Ala Gly Ala Gly Ala Arg Leu Val Val Phe
        35                  40                  45

Pro Glu Ala Phe Ile Gly Gly Tyr Pro Lys Gly Asn Ser Phe Gly Ala
    50                  55                  60

Pro Val Gly Met Arg Lys Pro Glu Gly Arg Glu Ala Phe Arg Leu Tyr
65                  70                  75                  80

Trp Glu Ala Ala Ile Asp Leu Asp Gly Val Glu Val Glu Thr Ile Ala
                85                  90                  95

Ala Ala Ala Ala Ala Thr Gly Ala Phe Thr Val Ile Gly Cys Ile Glu
            100                 105                 110

Arg Glu Gln Gly Thr Leu Tyr Cys Thr Ala Leu Phe Phe Asp Gly Ala
        115                 120                 125

Arg Gly Leu Val Gly Lys His Arg Lys Leu Met Pro Thr Ala Gly Glu
    130                 135                 140

Arg Leu Ile Trp Gly Phe Gly Asp Gly Ser Thr Met Pro Val Phe Glu
145                 150                 155                 160

Thr Ser Leu Gly Asn Ile Gly Ala Val Ile Cys Trp Glu Asn Tyr Met
                165                 170                 175

Pro Met Leu Arg Met His Met Tyr Ser Gln Gly Ile Ser Ile Tyr Cys
            180                 185                 190

Ala Pro Thr Ala Asp Asp Arg Asp Thr Trp Leu Pro Thr Met Gln His
        195                 200                 205

Ile Ala Leu Glu Gly Arg Cys Phe Val Leu Thr Ala Cys Gln His Leu
    210                 215                 220
```

```
Lys Arg Gly Ala Phe Pro Ala Asp Tyr Glu Cys Ala Leu Gly Ala Asp
225                 230                 235                 240

Pro Glu Thr Val Leu Met Arg Gly Gly Ser Ala Ile Val Asn Pro Leu
                245                 250                 255

Gly Lys Val Leu Ala Gly Pro Cys Phe Glu Gly Glu Thr Ile Leu Tyr
            260                 265                 270

Ala Asp Ile Ala Leu Asp Glu Val Thr Arg Gly Lys Phe Asp Phe Asp
        275                 280                 285

Ala Ala Gly His Tyr Ser Arg Pro Asp Val Phe Gln Leu Val Val Asp
    290                 295                 300

Asp Arg Pro Lys Arg Ala Val Ser Thr Val Ser Ala Val Arg Ala Arg
305                 310                 315                 320

Asn

<210> SEQ ID NO 63
<211> LENGTH: 933
<212> TYPE: DNA
<213> ORGANISM: Actinobacteria bacterium
<220> FEATURE:
<223> OTHER INFORMATION: Actinobacteria bacterium RBG_13_55_18

<400> SEQUENCE: 63
atgaaagttg ctgctgttca gatcaaagct aaactggctt gcgttgaaga aaacctggaa      60
cgtgctgaaa aactgctgga caaagctttc ggtcagggtt gcgaaatggt tatcctgccg     120
gaattcttca cctctgctgt tgctttccac ccggacatgc tgaccgctgc tctgccgttc     180
gaaggtccgg ctctgggtct gctgcgtgac gctgctaaac gttacggtgg ttacgctggt     240
ggttctttca tcgcttctcg tgaaggtaac aactacaaca ccttcgttct ggctttcccg     300
gacggtggtt acgttaccca caacaaagac cagccgacca tgtgggaaaa ctgctactac     360
atcggtggta acgacgaagg tatcatggaa accccgctgg gtccggttgg ttctgctctg     420
tgctgggaaa tggttcgtac ccgtaccgtt cgtcgtctgc gtggtcgtat cggtctggct     480
gttggtggtt cttgctggtg ggacgttccg gaccgtctgc tgccgctgcc gggtaaaaaa     540
tctgctaaac gtcgtaacct ggctatcatg aacgaaaccc cggttcgtct ggctaaaatg     600
ctgggtgttc cggttgttca cgctgctcac gctgaagctt cgaatgccg tatgccgctg     660
gttccgggta tcccgtaccg ttctcacttc ctgggtgaca ccatgatcgt tgacgctgac     720
ggttctgttc tggctcaccg ttctcgtgaa gaaggtgaag gtctggctat cgctgacgtt     780
cgtgttggtg gtatcgaacc gtctgaagac ccgccggacc gtttctggat cccggaactg     840
ccgctgctga tccgtttcgc ttgggcttac cagaacctgc acggtcgtct gtactaccgt     900
cgtgctctgc gtaccggtcg tatccagatc aaa                                   933

<210> SEQ ID NO 64
<211> LENGTH: 311
<212> TYPE: PRT
<213> ORGANISM: Actinobacteria bacterium
<220> FEATURE:
<223> OTHER INFORMATION: Actinobacteria bacterium RBG_13_55_18

<400> SEQUENCE: 64

Met Lys Val Ala Ala Val Gln Ile Lys Ala Lys Leu Ala Cys Val Glu
1               5                   10                  15

Glu Asn Leu Glu Arg Ala Glu Lys Leu Leu Asp Lys Ala Phe Gly Gln
                20                  25                  30

Gly Cys Glu Met Val Ile Leu Pro Glu Phe Phe Thr Ser Ala Val Ala
```

|  |  |  |  |  | 35 |  |  |  |  | 40 |  |  |  |  | 45 |  |  |
|--|--|--|--|--|----|--|--|--|--|----|--|--|--|--|----|--|--|

Phe His Pro Asp Met Leu Thr Ala Ala Leu Pro Phe Glu Gly Pro Ala
50                    55                      60

Leu Gly Leu Leu Arg Asp Ala Ala Lys Arg Tyr Gly Gly Tyr Ala Gly
65                  70                  75                  80

Gly Ser Phe Ile Ala Ser Arg Glu Gly Asn Tyr Asn Thr Phe Val
                    85                  90                  95

Leu Ala Phe Pro Asp Gly Gly Tyr Val Thr His Asn Lys Asp Gln Pro
                100                 105                 110

Thr Met Trp Glu Asn Cys Tyr Tyr Ile Gly Gly Asn Asp Glu Gly Ile
            115                 120                 125

Met Glu Thr Pro Leu Gly Pro Val Gly Ser Ala Leu Cys Trp Glu Met
130                 135                 140

Val Arg Thr Arg Thr Val Arg Arg Leu Arg Gly Arg Ile Gly Leu Ala
145                 150                 155                 160

Val Gly Gly Ser Cys Trp Trp Asp Val Pro Asp Arg Leu Leu Pro Leu
                165                 170                 175

Pro Gly Lys Lys Ser Ala Lys Arg Arg Asn Leu Ala Ile Met Asn Glu
                180                 185                 190

Thr Pro Val Arg Leu Ala Lys Met Leu Gly Val Pro Val Val His Ala
            195                 200                 205

Ala His Ala Glu Ala Phe Glu Cys Arg Met Pro Leu Val Pro Gly Ile
210                 215                 220

Pro Tyr Arg Ser His Phe Leu Gly Asp Thr Met Ile Val Asp Ala Asp
225                 230                 235                 240

Gly Ser Val Leu Ala His Arg Ser Arg Glu Glu Gly Glu Gly Leu Ala
                245                 250                 255

Ile Ala Asp Val Arg Val Gly Gly Ile Glu Pro Ser Glu Asp Pro Pro
                260                 265                 270

Asp Arg Phe Trp Ile Pro Glu Leu Pro Leu Leu Ile Arg Phe Ala Trp
            275                 280                 285

Ala Tyr Gln Asn Leu His Gly Arg Leu Tyr Tyr Arg Arg Ala Leu Arg
290                 295                 300

Thr Gly Arg Ile Gln Ile Lys
305                 310

<210> SEQ ID NO 65
<211> LENGTH: 1062
<212> TYPE: DNA
<213> ORGANISM: Rhizobium sp.
<220> FEATURE:
<223> OTHER INFORMATION: Rhizobium sp. YK2

<400> SEQUENCE: 65
atggaaaaca aatctatcgt tcgtgctgct gctgttcaga tcgctccgga cctgacctct      60
cgtgaaaaaa ccctggctcg tgttctggaa gctatccacg aagctgctgg taaaggtgct     120
gaactggctg ttttcccgga aaccttcgtt ccgtggtacc cgtacttctc tttcgttctg     180
ccgccggttc tgtctggtaa agaacacgtt cgtctgtacg acgaagctgt taccgttccg     240
tctgctgcta ccgaagctat cgctaccgct gctcgtaacc acggtatcgt tgttgttctg     300
ggtgttaacg aacgtgacca cggttctctg tacaacaccc agctggtttt caacgctgac     360
ggtaccctga tcctgaaacg tcgtaaaatc accccgacct tccacgaacg tatgatctgg     420
ggtcagggtg acgcttctgg tctgaccgtt gttgaatctc acgttggtcg tatcggtgct     480

-continued

```
ctggcttgct gggaacacta caacccgctg gctcgttacg ctctgatggc tcagcacgaa    540
gaaatccacg ttgctcagtt cccgggttct atggttggtc cgatcttcgc tgaacagatc    600
gaagttacca tccgtcacca cgctctggaa tctggttgct cgttgttaa cgctaccggt     660 tggctgaccg acgaacagat cgcttctatc accccggacc agaacctgca gaaagctctg    720
cgtggtggtt gcatgaccgc tatcatctct ccggaaggta acacctggc tccgccgctg     780 accgaaggtg aagtatcct gatcgctgac ctggacatgt ctctgatcac caaacgtaaa    840
cgtatgatgg actctgttgg tcactacgct cgtccggaac tgctgcacct ggttatcgac    900
ggtcgtgcta ccgctccgat ggttgcttct gaatcttctt cgaaaaccg taacccgtct    960 cagaccgctt ctccgcgttc taactctgac ggtcaccacg acaacgcttc ttctgaccgt   1020
gacccggacc agcgtgttgc tgttctgcgt tctcaggctt ct                      1062
```

<210> SEQ ID NO 66
<211> LENGTH: 354
<212> TYPE: PRT
<213> ORGANISM: Rhizobium sp.
<220> FEATURE:
<223> OTHER INFORMATION: Rhizobium sp. YK2

<400> SEQUENCE: 66

```
Met Glu Asn Lys Ser Ile Val Arg Ala Ala Val Gln Ile Ala Pro
1               5                   10                  15

Asp Leu Thr Ser Arg Glu Lys Thr Leu Ala Arg Val Leu Glu Ala Ile
            20                  25                  30

His Glu Ala Ala Gly Lys Gly Ala Glu Leu Ala Val Phe Pro Glu Thr
        35                  40                  45

Phe Val Pro Trp Tyr Pro Tyr Phe Ser Phe Val Leu Pro Pro Val Leu
    50                  55                  60

Ser Gly Lys Glu His Val Arg Leu Tyr Asp Glu Ala Val Thr Val Pro
65                  70                  75                  80

Ser Ala Ala Thr Glu Ala Ile Ala Thr Ala Ala Arg Asn His Gly Ile
                85                  90                  95

Val Val Val Leu Gly Val Asn Glu Arg Asp His Gly Ser Leu Tyr Asn
            100                 105                 110

Thr Gln Leu Val Phe Asn Ala Asp Gly Thr Leu Ile Leu Lys Arg Arg
        115                 120                 125

Lys Ile Thr Pro Thr Phe His Glu Arg Met Ile Trp Gly Gln Gly Asp
    130                 135                 140

Ala Ser Gly Leu Thr Val Val Glu Ser His Val Gly Arg Ile Gly Ala
145                 150                 155                 160

Leu Ala Cys Trp Glu His Tyr Asn Pro Leu Ala Arg Tyr Ala Leu Met
                165                 170                 175

Ala Gln His Glu Glu Ile His Val Ala Gln Phe Pro Gly Ser Met Val
            180                 185                 190

Gly Pro Ile Phe Ala Glu Gln Ile Glu Val Thr Ile Arg His His Ala
        195                 200                 205

Leu Glu Ser Gly Cys Phe Val Val Asn Ala Thr Gly Trp Leu Thr Asp
    210                 215                 220

Glu Gln Ile Ala Ser Ile Thr Pro Asp Gln Asn Leu Gln Lys Ala Leu
225                 230                 235                 240

Arg Gly Gly Cys Met Thr Ala Ile Ile Ser Pro Glu Gly Lys His Leu
                245                 250                 255

Ala Pro Pro Leu Thr Glu Gly Glu Gly Ile Leu Ile Ala Asp Leu Asp
```

```
                    260                 265                 270
Met Ser Leu Ile Thr Lys Arg Lys Arg Met Met Asp Ser Val Gly His
                275                 280                 285

Tyr Ala Arg Pro Glu Leu Leu His Leu Val Ile Asp Gly Arg Ala Thr
            290                 295                 300

Ala Pro Met Val Ala Ser Glu Ser Ser Phe Glu Asn Arg Asn Pro Ser
305                 310                 315                 320

Gln Thr Ala Ser Pro Arg Ser Asn Ser Asp Gly His His Asp Asn Ala
                325                 330                 335

Ser Ser Asp Arg Asp Pro Asp Gln Arg Val Ala Val Leu Arg Ser Gln
                340                 345                 350

Ala Ser

<210> SEQ ID NO 67
<211> LENGTH: 951
<212> TYPE: DNA
<213> ORGANISM: bacterium YEK0313

<400> SEQUENCE: 67
atgtctgttg ttcgttacaa agctgctgtt gctcaggctg cttcttgccc ggacgacgct      60
atggcttctg ctaccaaagc tgctcgtctg atcgaagaag ctgctggtgc tggtgctcgt     120
ctgatcgttt tcccggaagc tttcctgggt ggttacccga aggtgcttc tttcggtgct     180 ccgatcggta tgcgtaaacc ggaaggtcgt gacgctttcc gtcactactt cgaacaggct     240
atcgacctgg acggtccgga agttgctgct atcgctgctg ctaccgctac caccggtctg     300
ttcgctgtta tcggttgcat cgaacgtgac ggtggtaccc tgcactgcac cgttctgttc     360
ttcgacggtg ctgctggtct ggttggtaaa caccgtaaac tgatgccgac cgctggtgaa     420
cgtctgatct ggggtttcgg tgacggttct accatgccgg ttttcaaaac ctctctgggt     480
cgtatcggtg ctgttatctg ctgggaaaac tacatgccga tgctgcgtat gcacatgttc     540
tctcagggta tctctatcta ctgcgctccg accgctgacg accgtgacac ctggctgccg     600
tctatgcgtc acatcgctct ggaaggtcgt tgcttcgttc tgaccgcttg ccagcacatc     660
cgtcgtggtg ctttcccggc tggtcacgaa tgcgctctgg gtgacgaccc ggacaccgtt     720
ctgatgcgtg tggttctgc tatcgttgac ccgctgggtg tgttctggc tggtccggac     780 ttcaccggtg aaaccatcct gtacgctgac atcgacctgg gtgaagttgc tcgtggtaaa     840
ttcgacttcg acgttgttgg tcactacgct cgtccggaca tcttctctct gaccgttgac     900
gaccgtccgc gtccggctgt ttctacccta ggtgacccgc aggctggttc t              951

<210> SEQ ID NO 68
<211> LENGTH: 317
<212> TYPE: PRT
<213> ORGANISM: bacterium YEK0313

<400> SEQUENCE: 68

Met Ser Val Val Arg Tyr Lys Ala Ala Val Ala Gln Ala Ala Ser Cys
1               5                   10                  15

Pro Asp Asp Ala Met Ala Ser Ala Thr Lys Ala Ala Arg Leu Ile Glu
            20                  25                  30

Glu Ala Ala Gly Ala Gly Ala Arg Leu Ile Val Phe Pro Glu Ala Phe
        35                  40                  45

Leu Gly Gly Tyr Pro Lys Gly Ala Ser Phe Gly Ala Pro Ile Gly Met
    50                  55                  60
```

Arg Lys Pro Glu Gly Arg Asp Ala Phe Arg His Tyr Phe Glu Gln Ala
65                  70                  75                  80

Ile Asp Leu Asp Gly Pro Glu Val Ala Ala Ile Ala Ala Ala Thr Ala
                85                  90                  95

Thr Thr Gly Leu Phe Ala Val Ile Gly Cys Ile Glu Arg Asp Gly Gly
            100                 105                 110

Thr Leu His Cys Thr Val Leu Phe Phe Asp Gly Ala Ala Gly Leu Val
        115                 120                 125

Gly Lys His Arg Lys Leu Met Pro Thr Ala Gly Glu Arg Leu Ile Trp
130                 135                 140

Gly Phe Gly Asp Gly Ser Thr Met Pro Val Phe Lys Thr Ser Leu Gly
145                 150                 155                 160

Arg Ile Gly Ala Val Ile Cys Trp Glu Asn Tyr Met Pro Met Leu Arg
                165                 170                 175

Met His Met Phe Ser Gln Gly Ile Ser Ile Tyr Cys Ala Pro Thr Ala
            180                 185                 190

Asp Asp Arg Asp Thr Trp Leu Pro Ser Met Arg His Ile Ala Leu Glu
        195                 200                 205

Gly Arg Cys Phe Val Leu Thr Ala Cys Gln His Ile Arg Arg Gly Ala
210                 215                 220

Phe Pro Ala Gly His Glu Cys Ala Leu Gly Asp Asp Pro Asp Thr Val
225                 230                 235                 240

Leu Met Arg Gly Gly Ser Ala Ile Val Asp Pro Leu Gly Gly Val Leu
                245                 250                 255

Ala Gly Pro Asp Phe Thr Gly Glu Thr Ile Leu Tyr Ala Asp Ile Asp
            260                 265                 270

Leu Gly Glu Val Ala Arg Gly Lys Phe Asp Phe Asp Val Val Gly His
        275                 280                 285

Tyr Ala Arg Pro Asp Ile Phe Ser Leu Thr Val Asp Asp Arg Pro Arg
290                 295                 300

Pro Ala Val Ser Thr Leu Gly Asp Pro Gln Ala Gly Ser
305                 310                 315

<210> SEQ ID NO 69
<211> LENGTH: 819
<212> TYPE: DNA
<213> ORGANISM: Paenibacillus darwinianus

<400> SEQUENCE: 69

```
atgatccgtg aaggtaaccg tctgaccgtt gctgctgttc agatgaactg cgttctgggt      60
gacgttgaag ctaacctgcg taaagctgaa cgtctgctgg aaatcgctgc tggtcgtggt     120
gctcgtctgg ctgttctgcc ggaactgttc aacaccggtt accgtgttga agaacgtgac     180
gttgaactgg ctgaaccgat cccgggtccg accaccgaat ggatgcgtcg tcaggcttct     240
aaacacggta tgaaactggt tgctgctatc ctggaaaaag gtgctccggc tggtctggtt     300
tacgacaccg ctgttctggt tgaaccggct ggtgttatcg ttcttaccg  taaaccccac     360 ctgtggaacc aggaaaacac ccgtttcacc cgtggtgaac agttcccggt ttacgaaacc     420
gacggtatcc aggttggtct gcagatctgc tacgaaatcg gtttcccgga aggtgctcgt     480
atcctgacct ccacggtgc  tgacatcatc gtttacccgt ctgctttcgg taaagctcgt     540
ctgtacgctt gggacatcgc tacccgttct cgtgctctgg aaaacggtac cttcgttatc     600
gcttctaacc gtaccggtct ggaaaaaggt gaaaccgaat cggtggtac  ctctcgtatc     660 gttgacccgg ctggtaccat cctggctgaa gctgaacagg aagacgacgt tatcaccgct     720
```

```
gaactggacc tgggtctgat cgctgaacag cgtcgtgcta tcccgtacct gcgtgacttc      780
aaccgttctc tgatctctaa agaatacaac tctgaacgt                            819

<210> SEQ ID NO 70
<211> LENGTH: 273
<212> TYPE: PRT
<213> ORGANISM: Paenibacillus darwinianus

<400> SEQUENCE: 70
```

Met Ile Arg Glu Gly Asn Arg Leu Thr Val Ala Ala Val Gln Met Asn
1               5                   10                  15

Cys Val Leu Gly Asp Val Glu Ala Asn Leu Arg Lys Ala Glu Arg Leu
            20                  25                  30

Leu Glu Ile Ala Ala Gly Arg Gly Ala Arg Leu Ala Val Leu Pro Glu
        35                  40                  45

Leu Phe Asn Thr Gly Tyr Arg Val Glu Glu Arg Asp Val Glu Leu Ala
    50                  55                  60

Glu Pro Ile Pro Gly Pro Thr Thr Glu Trp Met Arg Arg Gln Ala Ser
65                  70                  75                  80

Lys His Gly Met Lys Leu Val Ala Ala Ile Leu Glu Lys Gly Ala Pro
                85                  90                  95

Ala Gly Leu Val Tyr Asp Thr Ala Val Leu Val Glu Pro Ala Gly Val
            100                 105                 110

Ile Gly Ser Tyr Arg Lys Thr His Leu Trp Asn Gln Glu Asn Thr Arg
        115                 120                 125

Phe Thr Arg Gly Glu Gln Phe Pro Val Tyr Glu Thr Asp Gly Ile Gln
    130                 135                 140

Val Gly Leu Gln Ile Cys Tyr Glu Ile Gly Phe Pro Glu Gly Ala Arg
145                 150                 155                 160

Ile Leu Thr Phe His Gly Ala Asp Ile Ile Val Tyr Pro Ser Ala Phe
                165                 170                 175

Gly Lys Ala Arg Leu Tyr Ala Trp Asp Ile Ala Thr Arg Ser Arg Ala
            180                 185                 190

Leu Glu Asn Gly Thr Phe Val Ile Ala Ser Asn Arg Thr Gly Leu Glu
        195                 200                 205

Lys Gly Glu Thr Glu Phe Gly Gly Thr Ser Arg Ile Val Asp Pro Ala
    210                 215                 220

Gly Thr Ile Leu Ala Glu Ala Glu Gln Glu Asp Asp Val Ile Thr Ala
225                 230                 235                 240

Glu Leu Asp Leu Gly Leu Ile Ala Glu Gln Arg Arg Ala Ile Pro Tyr
                245                 250                 255

Leu Arg Asp Phe Asn Arg Ser Leu Ile Ser Lys Glu Tyr Asn Ser Glu
            260                 265                 270

Arg

```
<210> SEQ ID NO 71
<211> LENGTH: 1098
<212> TYPE: DNA
<213> ORGANISM: Haloarcula sp.
<220> FEATURE:
<223> OTHER INFORMATION: Haloarcula sp. CBA1115

<400> SEQUENCE: 71
atgccggctg aatctttcac cctggctgct gctcaggttg aaccggttta ccacgacaaa      60
gaaggtaccc tggacaaaac ctgccgttac atcgaacagg ctggtcgtga cggtgctgac     120
```

```
atcgttgttt tcccggaaac ctacttcccg ggttacccgt actggcgtgg ttctgtttct      180
atctctcgtt ggaccgacct gatggttgac ctgcagaaaa actctctgca cgttgacgac      240
gaagctatcg aagttctggg tgaagctgtt gctgaagctg acctgaccct ggttctgggt      300
accaacgaag tttctgaccg tcagggttct gaaaccctgt acaactctct gttctacttc      360
gactctaccg gtgaactgat gggtcgtcac cgtaaactga tgccgaccca cgaagaacgt      420
gctatctggg gtcgtggtga cccgtcttct ctggctacct acgaaaccga catcggttgg      480
ctgggtggtc tgatctgcta cgaaaaccac atgaccctgt ctaaagctgc tctgaccgct      540
atgggtgaag aaatccacgc tgctgtttgg ccgggtttct ggaaacagca cggtcacccg      600
ggtgacaaaa cccgtgctga aacctctgaa gctgttgaca cctgcgacat ctacccggct      660
atgcgtgaat acgctttcga aacccagtct ttcgttgctg cttgctctgc ttacatgtct      720
gacgctgttc cggacggttt ctctgaagac gaactgggtt caacgttgc tgctggtggt       780 tctatgctga tcaaccggc tggtatcgtt aaagctggtc cgctggttgg tgaagaaggt       840
ctgctgaccg ctgaattcca ggacgacgaa cgtcgtgcta ccaaagctta cttcgacgct      900
atgggtcact acaccgttg ggacgctgtt tctctgtcta tcaacgacga aaccctggct       960
ccgtctcagc cgcgtgaacc gtctaaaaac ccggttgctg gtacctcttc tctgtctgct     1020
gctcaggctc aggctgttgc tgacgaatac gacgttccgg ttgaagctgt tgaagctgtt     1080
gctgacaaac tgaccgac                                                    1098

<210> SEQ ID NO 72
<211> LENGTH: 366
<212> TYPE: PRT
<213> ORGANISM: Haloarcula sp.
<220> FEATURE:
<223> OTHER INFORMATION: Haloarcula sp. CBA1115

<400> SEQUENCE: 72

Met Pro Ala Glu Ser Phe Thr Leu Ala Ala Ala Gln Val Glu Pro Val
1               5                   10                  15

Tyr His Asp Lys Glu Gly Thr Leu Asp Lys Thr Cys Arg Tyr Ile Glu
            20                  25                  30

Gln Ala Gly Arg Asp Gly Ala Asp Ile Val Val Phe Pro Glu Thr Tyr
        35                  40                  45

Phe Pro Gly Tyr Pro Tyr Trp Arg Gly Ser Val Ser Ile Ser Arg Trp
    50                  55                  60

Thr Asp Leu Met Val Asp Leu Gln Lys Asn Ser Leu His Val Asp Asp
65                  70                  75                  80

Glu Ala Ile Glu Val Leu Gly Glu Ala Val Ala Glu Ala Asp Leu Thr
                85                  90                  95

Leu Val Leu Gly Thr Asn Glu Val Ser Asp Arg Gln Gly Ser Glu Thr
            100                 105                 110

Leu Tyr Asn Ser Leu Phe Tyr Phe Asp Ser Thr Gly Glu Leu Met Gly
        115                 120                 125

Arg His Arg Lys Leu Met Pro Thr His Glu Glu Arg Ala Ile Trp Gly
    130                 135                 140

Arg Gly Asp Pro Ser Ser Leu Ala Thr Tyr Glu Thr Asp Ile Gly Trp
145                 150                 155                 160

Leu Gly Gly Leu Ile Cys Tyr Glu Asn His Met Thr Leu Ser Lys Ala
                165                 170                 175

Ala Leu Thr Ala Met Gly Glu Glu Ile His Ala Ala Val Trp Pro Gly
```

```
                180              185                190
Phe Trp Lys Gln His Gly His Pro Gly Asp Lys Thr Arg Ala Glu Thr
            195                 200                 205
Ser Glu Ala Val Asp Thr Cys Asp Ile Tyr Pro Ala Met Arg Glu Tyr
            210                 215                 220
Ala Phe Glu Thr Gln Ser Phe Val Ala Ala Cys Ser Ala Tyr Met Ser
225                 230                 235                 240
Asp Ala Val Pro Asp Gly Phe Ser Glu Asp Leu Gly Phe Asn Val
                245                 250                 255
Ala Ala Gly Gly Ser Met Leu Ile Asn Pro Ala Gly Ile Val Lys Ala
                260                 265                 270
Gly Pro Leu Val Gly Glu Glu Gly Leu Leu Thr Ala Glu Phe Gln Asp
            275                 280                 285
Asp Glu Arg Arg Ala Thr Lys Ala Tyr Phe Asp Ala Met Gly His Tyr
            290                 295                 300
Thr Arg Trp Asp Ala Val Ser Leu Ser Ile Asn Asp Glu Thr Leu Ala
305                 310                 315                 320
Pro Ser Gln Pro Arg Glu Pro Ser Lys Asn Pro Val Ala Gly Thr Ser
                325                 330                 335
Ser Leu Ser Ala Ala Gln Ala Gln Ala Val Ala Asp Glu Tyr Asp Val
                340                 345                 350
Pro Val Glu Ala Val Glu Ala Val Ala Asp Lys Leu Thr Asp
            355                 360                 365

<210> SEQ ID NO 73
<211> LENGTH: 1062
<212> TYPE: DNA
<213> ORGANISM: Hungatella hathewayi

<400> SEQUENCE: 73
atgtctaaaa aagaaaccgt taaagaagtt acccacacca tcggtgacac cctgccgaaa    60
ctgcgtgctg ctgctgttca ggctgctccg gttttcctga accgtgacgc taccgttcag   120
aaagttgctc gtctgaccaa agaagctaaa gacaacggtg ctgacctggt tgttttcccg   180
gaatctttca tcccgacctt cccgctgtgg tgcctgttcc tgccgccggt tgaccagcac   240
ccgttctaca acgtctgtt cgaaaacgct gttaccgttc gggtccggc tttccacgaa    300
ctgcagaaaa tcgctcgtga caactctatc ttcctgtctg ttggtatctg cgaaaaatct   360
acctctaact tcggtaccat gtggaacacc accctgctgt tcgaccgtga aggtaacatg   420
atcggtcacc accgtaaact gctgccgacc tggggtgaaa aactggtttg gtctttcggt   480
gacggttctt ctctgaacat ccacgacacc gaaatcggtc gtatcggttc tctgatctgc   540
ggtgaaaact ctaacaccct ggctcgttac gctctggttg ctcagggtga acaggttcac   600
atctctgttt acccgccgtg ctggccgacc aaccgtgaaa aggtaacta cgctgactgc   660
ctgcgtgttc gtacctgcgc tcacgctttc gaagctaaag ttttcaacat ctgctcttct   720
gcttctctgg acgaagacgc tatggaacag atgtctatgg gtgacccggc tctgaaagaa   780
tggctgcaca accagtcttg ggctctgacc atgatcgctg tccgaacgg tcagccgtgc   840
tgcccgtcta tcgaaacaa ccaggaaggt atcatctacg ctgactgcga catcgctaac   900
gaaatcaccg ctaaaggtat ccacgacatc gctggtgctt accagcgttt cgacgttttc   960
cagctgcacg ttaacaaaac cccgcgtgaa ccggcttact tctacgacga aggtatcggt  1020
gaatctcgtg aatacatccc gtacgaagaa gaagacaccg aa                     1062
```

<210> SEQ ID NO 74
<211> LENGTH: 354
<212> TYPE: PRT
<213> ORGANISM: Hungatella hathewayi

<400> SEQUENCE: 74

| | | | | | | | | | | | | | | | |
|---|---|---|---|---|---|---|---|---|---|---|---|---|---|---|---|
| Met | Ser | Lys | Lys | Glu | Thr | Val | Lys | Glu | Val | Thr | His | Thr | Ile | Gly | Asp |
| 1 | | | | 5 | | | | | 10 | | | | | 15 | |
| Thr | Leu | Pro | Lys | Leu | Arg | Ala | Ala | Val | Gln | Ala | Ala | Pro | Val | Phe | |
| | | | 20 | | | | | 25 | | | | | 30 | | |
| Leu | Asn | Arg | Asp | Ala | Thr | Val | Gln | Lys | Val | Ala | Arg | Leu | Thr | Lys | Glu |
| | | | 35 | | | | | 40 | | | | | 45 | | |
| Ala | Lys | Asp | Asn | Gly | Ala | Asp | Leu | Val | Val | Phe | Pro | Glu | Ser | Phe | Ile |
| | 50 | | | | | 55 | | | | | 60 | | | | |
| Pro | Thr | Phe | Pro | Leu | Trp | Cys | Leu | Phe | Leu | Pro | Pro | Val | Asp | Gln | His |
| 65 | | | | | 70 | | | | | 75 | | | | | 80 |
| Pro | Phe | Tyr | Lys | Arg | Leu | Phe | Glu | Asn | Ala | Val | Thr | Val | Pro | Gly | Pro |
| | | | | 85 | | | | | 90 | | | | | 95 | |
| Ala | Phe | His | Glu | Leu | Gln | Lys | Ile | Ala | Arg | Asp | Asn | Ser | Ile | Phe | Leu |
| | | | 100 | | | | | 105 | | | | | 110 | | |
| Ser | Val | Gly | Ile | Cys | Glu | Lys | Ser | Thr | Ser | Asn | Phe | Gly | Thr | Met | Trp |
| | | | 115 | | | | | 120 | | | | | 125 | | |
| Asn | Thr | Thr | Leu | Leu | Phe | Asp | Arg | Glu | Gly | Asn | Met | Ile | Gly | His | His |
| | 130 | | | | | 135 | | | | | 140 | | | | |
| Arg | Lys | Leu | Leu | Pro | Thr | Trp | Gly | Glu | Lys | Leu | Val | Trp | Ser | Phe | Gly |
| 145 | | | | | 150 | | | | | 155 | | | | | 160 |
| Asp | Gly | Ser | Ser | Leu | Asn | Ile | His | Asp | Thr | Glu | Ile | Gly | Arg | Ile | Gly |
| | | | | 165 | | | | | 170 | | | | | 175 | |
| Ser | Leu | Ile | Cys | Gly | Glu | Asn | Ser | Asn | Thr | Leu | Ala | Arg | Tyr | Ala | Leu |
| | | | 180 | | | | | 185 | | | | | 190 | | |
| Val | Ala | Gln | Gly | Glu | Gln | Val | His | Ile | Ser | Val | Tyr | Pro | Pro | Cys | Trp |
| | | | 195 | | | | | 200 | | | | | 205 | | |
| Pro | Thr | Asn | Arg | Glu | Lys | Gly | Asn | Tyr | Ala | Asp | Cys | Leu | Arg | Val | Arg |
| | 210 | | | | | 215 | | | | | 220 | | | | |
| Thr | Cys | Ala | His | Ala | Phe | Glu | Ala | Lys | Val | Phe | Asn | Ile | Cys | Ser | Ser |
| 225 | | | | | 230 | | | | | 235 | | | | | 240 |
| Ala | Ser | Leu | Asp | Glu | Asp | Ala | Met | Glu | Gln | Met | Ser | Met | Gly | Asp | Pro |
| | | | | 245 | | | | | 250 | | | | | 255 | |
| Ala | Leu | Lys | Glu | Trp | Leu | His | Asn | Gln | Ser | Trp | Ala | Leu | Thr | Met | Ile |
| | | | 260 | | | | | 265 | | | | | 270 | | |
| Ala | Gly | Pro | Asn | Gly | Gln | Pro | Cys | Cys | Pro | Ser | Ile | Glu | Asn | Asn | Gln |
| | | | 275 | | | | | 280 | | | | | 285 | | |
| Glu | Gly | Ile | Ile | Tyr | Ala | Asp | Cys | Asp | Ile | Ala | Asn | Glu | Ile | Thr | Ala |
| | 290 | | | | | 295 | | | | | 300 | | | | |
| Lys | Gly | Ile | His | Asp | Ile | Ala | Gly | Ala | Tyr | Gln | Arg | Phe | Asp | Val | Phe |
| 305 | | | | | 310 | | | | | 315 | | | | | 320 |
| Gln | Leu | His | Val | Asn | Lys | Thr | Pro | Arg | Glu | Pro | Ala | Tyr | Phe | Tyr | Asp |
| | | | | 325 | | | | | 330 | | | | | 335 | |
| Glu | Gly | Ile | Gly | Glu | Ser | Arg | Glu | Tyr | Ile | Pro | Tyr | Glu | Glu | Glu | Asp |
| | | | 340 | | | | | 345 | | | | | 350 | | |
| Thr | Glu | | | | | | | | | | | | | | |

<210> SEQ ID NO 75
<211> LENGTH: 5365

<212> TYPE: DNA
<213> ORGANISM: Artificial sequence
<220> FEATURE:
<223> OTHER INFORMATION: Plasmid

<400> SEQUENCE: 75

| | | | | | |
|---|---|---|---|---|---|
| cgatcaccac | aattcagcaa | attgtgaaca | tcatcacgtt | catctttccc | tggttgccaa | 60 |
| tggcccattt | tcctgtcagt | aacgagaagg | tcgcgaattc | aggcgctttt | tagactggtc | 120 |
| gtaatgaaca | attcttaaga | aggagatata | catatgcaga | caagaaaaat | cgtccgggca | 180 |
| gccgccgtac | aggccgcctc | tcccaactac | gatctggcaa | cgggtgttga | taaaaccatt | 240 |
| gagctggctc | gtcaggcccg | cgatgagggc | tgtgacctga | tcgtgtttgg | tgaaacctgg | 300 |
| ctgcccggat | atcccttcca | cgtctggctg | ggcgcaccgg | cctggtcgct | gaaatacagt | 360 |
| gcccgctact | atgccaactc | gctctcgctg | gacagtgcag | agtttcaacg | cattgcccag | 420 |
| gccgcacgga | ccttgggtat | tttcatcgca | ctgggttata | gcgagcgcag | cggcggcagc | 480 |
| ctttacctgg | gccaatgcct | gatcgacgac | aagggcgaga | tgctgtggtc | gcgtcgcaaa | 540 |
| ctcaaaccca | cgcatgtaga | gcgcaccgta | tttggtgaag | gttatgcccg | tgatctgatt | 600 |
| gtgtccgaca | cagaactggg | acgcgtcggt | gctctatgct | gctgggagca | tttgtcgccc | 660 |
| ttgagcaagt | acgcgctgta | ctcccagcat | gaagccattc | acattgctgc | ctggccgtcg | 720 |
| ttttcgctat | acagcgaaca | ggcccacgcc | tcagtgccaa | aggtgaacat | ggctgcctcg | 780 |
| caaatctatt | cggttgaagg | ccagtgcttt | accatcgccg | ccagcagtgt | ggtcacccaa | 840 |
| gagacgctag | acatgctgga | agtgggtgaa | cacaacgccc | ccttgctgaa | agtgggcggc | 900 |
| ggcagttcca | tgattttgc | gccggacgga | cgcacactgg | ctccctacct | gcctcacgat | 960 |
| gccgagggct | tgatcattgc | cgatctgaat | atggaggaga | ttgccttcgc | caaagcgatc | 1020 |
| aatgaccccg | taggccacta | ttccaaaccc | gaggccaccc | gtctggtgct | ggacttgggg | 1080 |
| caccgagacc | ccatgactcg | ggtgcactcc | aaaagcgtga | ccagggaaga | ggctcccgag | 1140 |
| caaggtgtgc | aaagcaagat | tgcctcagtc | gctatcagcc | atccacagga | ctcggacaca | 1200 |
| ctgctagtgc | aagagccgtc | cttgaggatc | cgtcgacctg | cagccaagct | tggctgtttt | 1260 |
| ggcggatgag | agaagatttt | cagcctgata | cagattaaat | cagaacgcag | aagcggtctg | 1320 |
| ataaaacaga | atttgcctgg | cggcagtagc | gcggtggtcc | cacctgaccc | catgccgaac | 1380 |
| tcagaagtga | aacgccgtag | cgccgatggt | agtgtggggt | ctccccatgc | gagagtaggg | 1440 |
| aactgccagg | catcaaataa | aacgaaaggc | tcagtcgaaa | gactgggcct | ttcgttttat | 1500 |
| ctgttgtttg | tcggtgaacg | ctctcctgag | taggacaaat | ccgccgggag | cggatttgaa | 1560 |
| cgttgcgaag | caacggcccg | gagggtggcg | ggcaggacgc | ccgccataaa | ctgccaggca | 1620 |
| tcaaattaag | cagaaggcca | tcctgacgga | tggcctttt | gcgtttctac | aaactctttt | 1680 |
| gtttattttt | ctaaatacat | tcaaatatgt | atccgctcat | gagacaataa | ccctgataaa | 1740 |
| tgcttcaata | atattgaaaa | aggaagagta | tgagtattca | acatttccgt | gtcgccctta | 1800 |
| ttccctttttt | tgcggcattt | tgccttcctg | tttttgctca | cccagaaacg | ctggtgaaag | 1860 |
| taaaagatgc | tgaagatcag | ttgggtgcac | gagtgggtta | catcgaactg | gatctcaaca | 1920 |
| gcggtaagat | ccttgagagt | tttcgccccg | aagaacgttt | tccaatgatg | agcacttta | 1980 |
| aagttctgct | atgtggcgcg | gtattatccc | gtgttgacgc | cgggcaagag | caactcggtc | 2040 |
| gccgcataca | ctattctcag | aatgacttgg | ttgagtactc | accagtcaca | gaaaagcatc | 2100 |
| ttacggatgg | catgacagta | agagaattat | gcagtgctgc | cataaccatg | agtgataaca | 2160 |

```
ctgcggccaa cttacttctg acaacgatcg gaggaccgaa ggagctaacc gcttttttgc     2220
acaacatggg ggatcatgta actcgccttg atcgttggga accggagctg aatgaagcca     2280
taccaaacga cgagcgtgac accacgatgc ctgtagcaat ggcaacaacg ttgcgcaaac     2340
tattaactgg cgaactactt actctagctt cccggcaaca attaatagac tggatggagg     2400
cggataaagt tgcaggacca cttctgcgct cggcccttcc ggctggctgg tttattgctg     2460
ataaatctgg agccggtgag cgtgggtctc gcggtatcat tgcagcactg gggccagatg     2520
gtaagccctc ccgtatcgta gttatctaca cgacggggag tcaggcaact atggatgaac     2580
gaaatagaca gatcgctgag ataggtgcct cactgattaa gcattggtaa ctgtcagacc     2640
aagtttactc atatatactt tagattgatt taaaacttca tttttaattt aaaaggatct     2700
aggtgaagat cctttttgat aatctcatga ccaaaatccc ttaacgtgag ttttcgttcc     2760
actgagcgtc agacccgta gaaaagatca aaggatcttc ttgagatcct ttttttctgc      2820
gcgtaatctg ctgcttgcaa acaaaaaaac caccgctacc agcggtggtt tgtttgccgg     2880
atcaagagct accaactctt tttccgaagg taactggctt cagcagagcg cagataccaa     2940
atactgtcct tctagtgtag ccgtagttag gccaccactt caagaactct gtagcaccgc     3000
ctacatacct cgctctgcta atcctgttac cagtggctgc tgccagtggc gataagtcgt     3060
gtcttaccgg gttggactca agacgatagt taccggataa ggcgcagcgg tcgggctgaa     3120
cggggggttc gtgcacacag cccagcttgg agcgaacgac ctacaccgaa ctgagatacc     3180
tacagcgtga gctatgagaa agcgccacgc ttcccgaagg gagaaaggcg gacaggtatc     3240
cggtaagcgg cagggtcgga acaggagagc gcacgaggga gcttccaggg ggaaacgcct     3300
ggtatcttta tagtcctgtc gggtttcgcc acctctgact tgagcgtcga ttttttgtgat    3360 gctcgtcagg gggcggagc ctatggaaaa acgccagcaa cgcggccttt ttacggttcc      3420
tggccttttg ctggcctttt gctcacatgt tctttcctgc gttatcccct gattctgtgg     3480
ataaccgtat taccgccttt gagtgagctg ataccgctcg ccgcagccga acgaccgagc     3540
gcagcgagtc agtgagcgag gaagcggaag agcgcctgat gcggtatttt ctccttacgc     3600
atctgtgcgg tatttcacac cgcatatatg gtgcactctc agtacaatct gctctgatgc     3660
cgcatagtta agccagtata cactccgcta tcgctacgtg actgggtcat ggctgcgccc     3720
cgacacccgc caacacccgc tgacgcgccc tgacgggctt gtctgctccc ggcatccgct     3780
tacagacaag ctgtgaccgt ctccgggagc tgcatgtgtc agaggttttc accgtcatca     3840
ccgaaacgcg cgaggcagct gcggtaaagc tcatcagcgt ggtcgtgaag cgattcacag     3900
atgtctgcct gttcatccgc gtccagctcg ttgagtttct ccagaagcgt taatgtctgg     3960
cttctgataa agcgggccat gttaagggcg gttttttcct gtttggtcac tgatgcctcc     4020
gtgtaagggg gatttctgtt catggggta atgataccga tgaaacgaga gaggatgctc      4080
acgatacggg ttactgatga tgaacatgcc cggttactgg aacgttgtga gggtaaacaa     4140
ctggcggtat ggatgcggcg ggaccagaga aaaatcactc agggtcaatg ccagcgcttc     4200
gttaatacag atgtaggtgt tccacagggt agccagcagc atcctgcgat gcagatccgg     4260
aacataatgg tgcagggcgc tgacttccgc gtttccagac tttacgaaac acggaaaccg     4320
aagaccattc atgttgttgc tcaggtcgca gacgttttgc agcagcagtc gcttcacgtt     4380
cgctcgcgta tcggtgattc attctgctaa ccagtaaggc aaccccgcca gcctagccgg     4440
gtcctcaacg acaggagcac gatcatgcgc acccgtggcc aggacccaac gctgcccgag     4500
atgcgccgcg tgcggctgct ggagatggcg gacgcgatgg atatgttctg ccaagggttg     4560
```

```
gtttgcgcat tcacagttct ccgcaagaat tgattggctc caattcttgg agtggtgaat    4620
ccgttagcga ggtgccgccg gcttccattc aggtcgaggt ggcccggctc catgcaccgc    4680
gacgcaacgc ggggaggcag acaaggtata gggcggcgcc tacaatccat gccaacccgt    4740
tccatgtgct cgccgaggcg gcataaatcg ccgtgacgat cagcggtcca atgatcgaag    4800
ttaggctggt aagagccgcg agcgatcctt gaagctgtcc ctgatggtcg tcatctacct    4860
gcctggacag catggcctgc aacgcgggca tcccgatgcc gccggaagcg agaagaatca    4920
taatggggaa ggccatccag cctcgcgtcg cgaacgccag caagacgtag cccagcgcgt    4980
cggccgccat gccggcgata atggcctgct tctcgccgaa acgtttggtg gcgggaccag    5040
tgacgaaggc ttgagcgagg gcgtgcaaga ttccgaatac cgcaagcgac aggccgatca    5100
tcgtcgcgct ccagcgaaag cggtcctcgc cgaaaatgac ccagacgct gccggcacct     5160 gtcctacgag ttgcatgata aagaagacag tcataagtgc ggcgacgata gtcatgcccc    5220
gcgcccaccg gaaggagctg actgggttga aggctctcaa gggcatcggt cgacgctctc    5280
ccttatgcga ctcctgcatt aggaagcagc ccagtagtag gttgaggccg ttgagcaccg    5340
ccgccgcaag gaatggtgca tgcat                                          5365
```

PROCESS FOR PRODUCING AMMONIUM (METH-) ACRYLATE

CROSS-REFERENCE TO RELATED APPLICATIONS

This application is a national stage application of PCT International Application No. PCT/EP2019/078158, filed on Oct. 17, 2019, which claims priority to European Application No. 18201231.0, filed on Oct. 18, 2018, the disclosures of which are hereby expressly incorporated by reference herein in their entireties.

The present invention relates to a process for preparing ammonium (meth-) acrylate, aqueous ammonium (meth-) acrylate solutions obtainable by such process, and (meth-) acrylic acid homopolymers or copolymers obtainable by polymerizing such ammonium (meth-) acrylate. The invention furthermore relates to a modular, relocatable bioconversion unit for manufacturing aqueous ammonium (meth-) acrylate solutions.

BACKGROUND OF THE INVENTION

Homopolymers of acrylic acid may be used for various applications such as surface coatings, adhesives, sealants, etc. Copolymers of (meth-) acrylic acid and for example acrylamide may be used for applications such as mining and oilfield applications, and agriculture. Examples include its use in the exploration and production of mineral oil, in particular, as thickener in aqueous injection fluids for enhanced oil recovery or as rheology modifier for aqueous drilling fluids. Further examples include its use as flocculating agent for tailings and slurries in mining activities.

The raw material for homo- and copolymers of acrylic acid is typically the monomer acrylic acid. In the case of copolymers in addition to acrylic acid the raw material would also include at least one further ethylenically unsaturated monomer that is co-polymerisable with acrylic acid, and typically this would frequently be acrylamide. In principal, there exists two different methods to produce acrylic acid on an industrial scale: Chemical synthesis and biological synthesis, wherein the biological synthesis methods are more and more on the rise due to milder reaction conditions and inherent process safety. Due to the milder reaction conditions and the quantitative conversion of the nitrile, expensive downstream processing steps such as distillation or ion exchange can be avoided in the biological synthesis, thus resulting in cheaper plants with drastically reduced plant footprint.

There are two distinct pathways for the enzymatic hydration of nitriles in plants and microorganisms that have been applied in industrial production of acrylic acid. One pathway comprises two enzymatic steps wherein a nitrile hydratase converts a nitrile to an amide which subsequently is hydrolysed by an amidase to yield acrylic acid (U.S. Pat. No. 6,670,158). The other pathway is a single-step reaction catalysed by nitrilases (U.S. Pat. No. 6,162,624), which is advantageous compared to the two-step reaction, because the latter requiring an extensive amount of equipment for the two stages. WO 97/21817 discloses suitable conditions for carrying out the enzymatic hydration of nitriles using nitrilases. US 2009/0311759 describes a process for producing acrylamide by allowing acrylonitrile to undergo a hydration reaction by the use of a microbial catalyst containing nitrile hydratase in an aqueous medium to obtain acrylamide reaction solution. The process includes a step of removing impurities from the reaction solution.

However, even when using a single-step reaction catalysed by nitrilases, for the obtained acrylic acid still further processing steps like purification and drying are necessary in order to obtain acrylic acid, which is suitable for the production of homo- and/or copolymers in acceptable quality. More specifically, without cleaning and drying before storage, aqueous ammonium (meth-) acrylate solutions could degrade, which could lead to reduced performance of the resulting polymers.

SUMMARY OF THE INVENTION

In the light of the prior art the technical problem underlying the present invention was the provision of a process for preparing aqueous ammonium (meth-) acrylate solutions that overcome the disadvantages of those methods known in the art. The process for preparing aqueous ammonium (meth-) acrylate solutions of the present invention comprises a relocatable bioconversion unit. Due to the conductions of the bioconversion in a relocatable bioconversion unit, cleaning and drying steps can be avoided. The method for preparing an aqueous ammonium (meth-) acrylate solution enables high product quality for subsequent polymer production and overcomes the disadvantages known in the art.

The problem is solved by the features of the independent claims. Preferred embodiments of the present invention are provided by the dependent claims.

The invention therefore relates to a process for producing aqueous ammonium (meth-) acrylate solutions, said process comprising the following steps:
  (a) adding the following components (i) to (iii) to a reactor to obtain a composition for bioconversion:
    (i) a biocatalyst capable of converting (meth-) acrylonitrile to ammonium (meth-) acrylate;
    (ii) (meth-) acrylonitrile;
    (iii) aqueous medium; and
  (b) performing a bioconversion on the composition obtained in step (a) in a reactor;
  wherein the reactor is a relocatable bioconversion unit. The composition obtained in step (a) is also called reaction mixture.

In a preferred embodiment the (meth-) acrylonitrile concentration of the composition at the end of the bioconversion is below 10.0% (w/w), is below 1.0% (w/w), is below 0.1% (w/w), preferably below 0.01% (w/w), more preferably below 0.001% (w/w), most preferably below 0.0001% (w/w) by weight of the (meth-) acrylonitrile in the aqueous medium.

In a preferred embodiment the concentration of ammonium (meth-) acrylate at the end of the bioconversion is at least 10% (w/w), at least 15% (w/w), at least 20% (w/w), at least 25% (w/w), at least 30% (w/w), at least 35% (w/w), preferably at least 40% (w/w), at least 45% (w/w), more preferably at least 50% (w/w), more preferably at least 51% (w/w), more preferably at least 52% (w/w), more preferably at least 53% (w/w), even more preferably at least 54% (w/w), most preferably at least 55% (w/w) by weight of the ammonium (meth-) acrylate monomers in the aqueous medium.

In a preferred embodiment the biocatalyst is an enzyme having nitrilase activity.

In a preferred embodiment the biocatalyst having nitrilase activity is one selected from the group consisting of an isolated nitrilase, a recombinant construct, a recombinant vector comprising the recombinant construct, a recombinant microorganism comprising the recombinant construct, and a recombinant microorganism comprising the recombinant vector.

In a preferred embodiment the biocatalyst is a recombinant microorganism selected from the group consisting of *Bacillus licheniformis, Bacillus pumilus, Bacillus subtilis, Escherichia coli, Saccharomyces cerevisiae, Rhodococcus rhodocrous*, and *Pichia pastoris*.

In a preferred embodiment the relocatable bioconversion unit comprises a reaction vessel having a volume from 10 m$^3$ to 150 m$^3$, means for mixing the reaction mixture and means for controlling the temperature of the reaction mixture. This may for instance be from about 20 m$^3$ to about 120 m$^3$, suitably from about 20 m$^3$ to about 100 m$^3$, preferably from about 20 m$^3$ to 50 m$^3$. The reaction vessel the reaction vessel may, for instance, be a single walled reaction vessel.

In an alternative embodiment the relocatable bioconversion unit comprises a double-walled reaction vessel having a volume from 10 m$^3$ to 150 m$^3$, means for mixing the reaction mixture and means for controlling the temperature of the reaction mixture. This may for instance be from about 20 m$^3$ to about 120 m$^3$, suitably from about 20 m$^3$ to about 100 m$^3$, preferably from about 20 m$^3$ to 50 m$^3$.

In a preferred embodiment the relocatable bioconversion unit comprises a frame, a double-walled reaction vessel mounted into the frame having a volume from 10 m$^3$ to 150 m$^3$, and an external temperature control circuit comprising at least a pump and a temperature control unit, wherein the reaction mixture is circulated by means of a pump from the reaction vessel into the temperature control unit and back into the reaction vessel, thereby simultaneously controlling the temperature and mixing the reaction mixture.

In a preferred embodiment the relocatable bioconversion unit comprises a frame, a single-walled reaction vessel mounted into the frame having a volume from 10 m$^3$ to 150 m$^3$, and an external temperature control circuit comprising at least a pump and a temperature control unit, wherein the reaction mixture is circulated by means of a pump from the reaction vessel into the temperature control unit and back into the reaction vessel, thereby simultaneously controlling the temperature and mixing the reaction mixture.

In a preferred embodiment the amount of reaction mixture cycled per hour through the temperature control circuit is from 100% to 1000% of the total volume of the reaction mixture in the bioconversion unit.

A further aspect of the invention relates to a reactor for manufacturing aqueous ammonium (meth-) acrylate solutions according to the process of the present invention, wherein the reactor is a relocatable bioconversion unit.

The reactor may comprise a stirrer. Suitably the reactor may comprise an external cooling circuit. It may be desirable for the reactor to comprise a stirrer and an external cooling circuit. It is preferable, however, for the reactor to comprise no stirrer. In a preferred embodiment the reactor comprises an external cooling circuit and the reactor comprises no stirrer. By stirrer we mean any active mixing device located in the reactor. Typically, a stirrer may be an impeller, an agitator mounted within the reactor or a moving device which is not fixed, such as a magnetic stirrer. By a reactor comprising no stirrer we mean that no active mixing device is located in the reactor.

In a preferred embodiment the reactor comprises
a relocatable storage unit for (meth-) acrylonitrile,
a relocatable bioconversion unit for hydrolyzing (meth-) acrylonitrile in water in the presence of a biocatalyst capable of converting (meth-) acrylonitrile to ammonium (meth-) acrylate,
optionally, a relocatable unit for removing the biocatalyst from an aqueous ammonium (meth-) acrylate solution,
optionally, a relocatable storage unit for an aqueous ammonium (meth-) acrylate solution, and
optionally, at least one relocatable unit for further processing an aqueous ammonium (meth-) acrylate solution.

In a preferred embodiment the reactor for manufacturing aqueous ammonium (meth-) acrylate solutions according to the present invention is used at a fixed production facility.

In a preferred embodiment the reactor for manufacturing aqueous ammonium (meth-) acrylate solutions according to the present invention is combined with a relocatable bioconversion unit for manufacturing an aqueous acrylamide solution.

A further aspect of the invention relates to aqueous ammonium (meth-) acrylate solutions obtainable by the process of the present invention.

A further aspect of the invention relates to (meth-) acrylate homopolymers or copolymers obtainable by polymerizing the ammonium (meth-) acrylate of the aqueous solution.

A further aspect of the invention relates to the use of aqueous ammonium (meth-) acrylate solutions prepared according to the present invention for preparing aqueous solutions of (meth-) acrylate homopolymers or copolymers.

A further aspect of the invention relates to the use of aqueous solutions of (meth-) acrylate homopolymers or copolymers according to the present invention as surface coatings, adhesives, sealants, for mining applications, oilfield applications, water treatment, waste water treatment, paper making or agricultural applications.

DETAILED DESCRIPTION OF THE INVENTION

With regards to the invention, the following can be stated specifically:

In a first aspect the invention relates to a process for producing ammonium (meth-) acrylate, said process comprising the following steps:
(a) adding the following components (i) to (iii) to a reactor to obtain a composition for bioconversion:
  (i) a biocatalyst capable of converting (meth-) acrylonitrile to ammonium (meth-) acrylate;
  (ii) (meth-) acrylonitrile;
  (iii) aqueous medium; and
(b) performing a bioconversion on the composition obtained in step (a) in a reactor; wherein the reactor is a relocatable bioconversion unit.

Surprisingly, it was found that using a relocatable bioconversion unit, aqueous ammonium (meth-) acrylate solutions are obtained, which are suitable for further processing to produce homo- and/or copolymers of (meth-) acrylic acid without drying the obtained aqueous ammonium (meth-) acrylate solutions. With that, drying as time consuming additional process step can be avoided. Surprising was also that the quality of the obtained homo- or copolymers of (meth-) acrylic acid are comparable with the quality of polymers prepared with acrylic acid, which has been cleaned and dried before polymerization. Therefore, a further advantage of the present invention is that for example better subsequent products/polymers can be obtained. Of advantage is also that with avoiding a drying step, the formation of ammonia gas during drying of aqueous ammonium (meth-) acrylate solutions can be avoided. In addition, for the production of copolymers comprising acrylic acid and acrylamide the same educt, namely acrylonitrile, can be used for the production of two different monomers. This offers the advantage of a more efficient sourcing and less transportation. Furthermore, with producing ammonium (meth-) acrylate in situ it is possible to avoid costly and risky transportation of caustic base, which would otherwise be necessary for neutralizing dried acrylic acid before polymerization. Also, risky transportation of caustic acrylic acid can be avoided. Beneficial is in addition the possibility to avoid a separation (e.g. centrifugation), a purification and/or drying step of the obtained aqueous ammonium (meth-) acrylate solution (ammonium (meth-) acrylate), which will make the further processing of the aqueous ammonium (meth-) acrylate solution according to the present invention easier. Also, a direct use of the aqueous ammonium (meth-) acrylate solution at the site of further processing and/or the use for a subsequent polymer production e.g. to form homopolymers of (meth-) acrylic acid and/or copolymers (e.g. of (meth-) acrylic acid and acrylamide) at the site of application is possible.

Ammonium (Meth-) Acrylate

As used herein, the term "ammonium (meth-) acrylate" in the context of this invention means ammonium (meth-) acrylate that may be synthesized by hydrolysis of (meth-) acrylonitrile using suitable catalysts. It is known in the art to use biocatalysts capable of converting (meth-) acrylonitrile to ammonium (meth-) acrylate (often referred to as "bio ammonium (meth-) acrylate"). Pure (meth-) acrylic acid is solid. However, typically ammonium (meth-) acrylate according to the present invention is made by bio catalysis and is provided as aqueous solution, for example as aqueous solution comprising about 50% by wt. of ammonium (meth-) acrylate. Ammonium (meth-) acrylate obtained by means of biocatalysts may still comprise traces of the biocatalyst. For the process according to the present invention an aqueous ammonium (meth-) acrylate solution is used which has been obtained by hydrolyzing (meth-) acrylonitrile in water in presence of a biocatalyst capable of converting (meth-) acrylonitrile to ammonium (meth-) acrylate. As will be detailed below, using biocatalysts for hydrolyzing (meth-) acrylonitrile has significant advantages for the present invention.

Biocatalyst

As used herein, the term "biocatalyst" in the context of this invention means nitrilase enzymes, which are capable of catalyzing the hydrolysis of (meth-) acrylonitrile to ammonium (meth-) acrylate. The conversion of (meth-) acrylonitrile to ammonium (meth-) acrylate using a biocatalyst may be called "bioconversion" or "bio-catalysis".

Preferably, the biocatalyst according to the present invention may be an enzyme with nitrilase activity comprising the sequence selected from the group consisting of an amino acid molecule of SEQ ID NO: 2, 4, 6, 8, 10, 12, 14, 18, 20, 22, 26, 28, 30, 32, 34, 38, 40, 42, 46, 48, 52, 54, 56, 60, 62, 64, 66 and 68 or a functional fragment thereof. Further preferred is that the biocatalyst is an enzyme with nitrilase activity comprising the sequence selected from the group consisting of an amino acid molecule encoded by a nucleic acid molecule of SEQ ID NO 1, 3, 5, 7, 9, 11, 13, 15, 17, 19, 21, 25, 27, 29, 31, 33, 37, 39, 41, 45, 47, 51, 53, 55, 59, 61, 63, 65 and 67 or a functional fragment thereof.

Preferably, the biocatalyst is an isolated nitrilase, a recombinant construct or a recombinant vector, which in particular is comprising said recombinant construct. Further preferred is that the biocatalyst is a recombinant microorganism comprising said recombinant construct or said recombinant vector.

Typically, nitrilase enzymes can be produced by a variety of microorganisms. Preferred microorganisms that can be used in the present invention include, but are not limited to, *Gluconobacter oxydans, Gluconobacter asaii, Achromobacter delmarvae, Achromobacter viscosus, Achromobacter lacticum, Agrobacterium tumefaciens, Agrobacterium radiobacter, Alcaligenes faecalis, Arthrobacter citreus, Arthrobacter tumescens, Arthrobacter paraffineus, Arthrobacter hydrocarboglutamicus, Arthrobacter oxydans, Aureobacterium saperdae, Azotobacter indicus, Brevibacterium ammoniagenes, Brevibacterium divaricatum, Brevibacterium lactofermentum, Brevibacterium flavum, Brevibacterium globosum, Brevibacterium fuscum, Brevibacterium ketoglutamicum, Brevibacterium helcolum, Brevibacterium pusillum, Brevibacterium testaceum, Brevibacterium roseum, Brevibacterium immariophilium, Brevibacterium linens, Brevibacterium protopharmiae, Corynebacterium acetophilum, Corynebacterium glutamicum, Corynebacterium callunae, Corynebacterium acetoacidophilum, Corynebacterium acetoglutamicum, Enterobacter aerogenes, Erwinia amylovora, Erwinia carotovora, Erwinia herbicola, Erwinia chrysanthemi, Flavobacterium peregrinum, Flavobacterium fucatum, Flavobacterium aurantinum, Flavobacterium rhenanum, Flavobacterium sewanense, Flavobacterium breve, Flavobacterium meningosepticum, Micrococcus sp. CCM825, Morganella morganii, Nocardia opaca, Nocardia rugosa, Planococcus eucinatus, Proteus rettgeri, Propionibacterium shermanii, Pseudomonas synxantha, Pseudomonas azotoformans, Pseudomonas jluorescens, Pseudomonas ovalis, Pseudomonas stutzeri, Pseudomonas acidovolans, Pseudomonas mucidolens, Pseudomonas testosteroni, Pseudomonas aeruginosa, Rhodococcus erythropolis, Rhodococcus rhodochrous, Rhodococcus sp. ATCC 15592, Rhodococcus sp. ATCC 19070, Sporosarcina ureae, Staphylococcus aureus, Vibrio metschnikovii, Vibrio tyrogenes, Actinomadura madurae, Actinomyces violaceochromogenes, Kitasatosporia parulosa, Streptomyces avermitilis, Streptomyces coelicolor, Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi, Streptomyces lavendulae, Streptomyces viridochromogenes, Aeromonas salmonicida, Bacillus pumilus, Bacillus circulans, Bacillus thiaminolyticus, Escherichia freundii, Microbacterium ammoniaphilum, Serratia marcescens, Salmonella typhimurium, Salmonella schottmulleri, Xanthomonas citri, Synechocystis sp., Synechococcus elongatus, Thermosynechococcus elongatus, Microcystis aeruginosa, Nostoc sp., N. commune, N. sphaericum, Nostoc punctiforme, Spirulina platensis, Lyngbya majuscula, L. lagerheimii, Phormidium tenue, Anabaena sp., Leptolyngbya sp* and so forth.

In some preferred embodiments, the microorganism is a eukaryotic cell. Suitable eukaryotic cells include yeast cells, as for example *Saccharomyces* spec, such as *Saccharomyces cerevisiae*, *Hansenula* spec, such as *Hansenula polymorpha*, *Schizosaccharomyces* spec, such as *Schizosaccharomyces pombe*, *Kluyveromyces* spec, such as *Kluyveromyces lactis* and *Kluyveromyces marxianus*, *Yarrowia* spec, such as *Yarrowia lipolytica*, *Pichia* spec, such as *Pichia methanolica*, *Pichia stipites* and *Pichia pastoris*, *Zygosaccharomyces* spec, such as *Zygosaccharomyces rouxii* and *Zygosaccharomyces bailii*, *Candida* spec, such as *Candida boidinii*, *Candida utilis*, *Candida freyschussii*, *Candida glabrata* and *Candida sonorensis*, *Schwanniomyces* spec, such as *Schwanniomyces occidentalis*, *Arxula* spec, such as *Arxula*

*adeninivorans, Ogataea* spec such as *Ogataea minuta, Klebsiella* spec, such as *Klebsiella pneumonia*.

A microorganism of the genus *Cupriavidus basilensis, Flavihumibacter solisilvae, Acidovorax facilis* 72W, *Pseudomonas* sp. RIT357, *Nocardia brasiliensis* NBRC 14402, *Pseudomonas fluorscens, Agrobacterium rubi, Candidatus Dadabacteria bacterium* CSP1-2, *Tepidicaulis marinus, Synechococcus* sp. CC9605, *Aquimarina atlantica, Arthrobacter* sp., *Sphingomonas wittichii* RW1, *Pseudomonas mandelii* JR-1, *Salinisphaera shabanensis* E1 L3A, *Smithella* sp. SDB, *Bradyrhizobium diazoefficiens, Actinobacteria bacterium* RBG_13_55_18, *Rhizobium* sp. YK2 or Bacterium YEK0313 expressing any of the nitrilases of the invention is another preferred embodiment of the invention.

Further, microorganisms suitable as biocatalyst for the enzymatic conversion of (meth-) acrylonitrile to ammonium (meth-) acrylate, which are known for a person skilled in the art, are able to be applied according to the present invention. Additionally, the specific methods known in the art of culturing (or cultivation, or fermentation) and/or storing the microorganism as well as the respective sequences of polynucleotides which are encoding the enzyme, particularly the nitrilase, are applicable in context of the present invention.

The term "isolated" as used herein means that a material has been removed by the hand of man and exists apart from its original, native environment and is therefore not a product of nature. An isolated material or molecule (such as a DNA molecule or enzyme) may exist in a purified form or may exist in a non-native environment such as, for example, in a transgenic host cell. For example, a naturally occurring nucleic acid molecule or polypeptide present in a living cell is not isolated, but the same nucleic acid molecule or polypeptide, separated from some or all of the coexisting materials in the natural system, is isolated. Such nucleic acid molecules can be part of a vector and/or such nucleic acid molecules or polypeptides could be part of a composition, and would be isolated in that such a vector or composition is not part of its original environment. Preferably, the term "isolated" when used in relation to a nucleic acid molecule, as in "an isolated nucleic acid sequence" refers to a nucleic acid sequence that is identified and separated from at least one contaminant nucleic acid molecule with which it is ordinarily associated in its natural source. Isolated nucleic acid molecule is nucleic acid molecule present in a form or setting that is different from that in which it is found in nature. In contrast, non-isolated nucleic acid molecules are nucleic acid molecules such as DNA and RNA, which are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs, which encode a multitude of proteins. However, an isolated nucleic acid sequence comprising for example SEQ ID NO: 1 includes, by way of example, such nucleic acid sequences in cells which ordinarily contain SEQ ID NO: 1 where the nucleic acid sequence is in a genomic or plasmid location different from that of natural cells, or is otherwise flanked by a different nucleic acid sequence than that found in nature. The isolated nucleic acid sequence may be present in single- or double-stranded form. When an isolated nucleic acid sequence is to be utilized to express a protein, the nucleic acid sequence will contain at a minimum at least a portion of the sense or coding strand (i.e., the nucleic acid sequence may be single-stranded). Alternatively, it may contain both the sense and anti-sense strands (i.e., the nucleic acid sequence may be double-stranded).

The term "nitrilase" as used herein refers to an enzyme catalyzing the reaction from meth-acrylonitrile to ammonium meth-acrylate and/or the reaction from acrylonitrile to ammonium acrylate. It also encompasses enzymes that are catalyzing additional reactions despite those mentioned before.

As used herein, the term "nitrilase producing microorganism" or "microorganism" or "biocatalysts" or the like in the context of this invention have the meaning to be able to produce (i.e. they encode and express) the enzyme nitrilase either per se (naturally) or they have been genetically modified respectively. Microorganisms which have been "genetically modified" means that these microorganisms have been manipulated such that they have acquired the capability to express the required enzyme nitrilase, e.g. by way of incorporation of a naturally and/or modified nitrile hydratase gene or gene cluster or the like. Produced products of the microorganisms that can be used in the context of the present invention are also contemplated, e.g. suspensions obtained by partial or complete cell disruption of the microorganisms.

The terms "nitrilase producing microorganism" or "microorganism" or "biocatalysts" or the like, include the cells and/or the processed product thereof as such, and/or suspensions containing such microorganisms and/or processed products. It is also envisaged that the microorganisms and/or processed products thereof are further treated before they are employed in the embodiments of the present invention. "Further treated" thereby includes for example washing steps and/or steps to concentrate the microorganism etc. It is also envisaged that the microorganisms that are employed in the embodiments of the present invention have been pre-treated by a for example drying step. Also known methods for cultivating of the microorganisms and how to optimize the cultivation conditions via for example addition of urea or cobalt are compassed by the embodiments of the present invention. Advantageously, the microorganism can be grown in a medium containing urea, acetonitrile or acrylonitrile as an inducer of the nitrilase.

As used herein, the term "vector" refers to a nucleic acid molecule capable of transporting another nucleic acid molecule to which it has been linked. One type of vector is a genomic integrated vector, or "integrated vector", which can become integrated into the genomic DNA of the host cell. Another type of vector is an episomal vector, i.e., a plasmid or a nucleic acid molecule capable of extra-chromosomal replication. Vectors capable of directing the expression of genes to which they are operatively linked are referred to herein as "expression vectors". In the present specification, "plasmid" and "vector" are used interchangeably unless otherwise clear from the context.

The term "recombinant microorganism" includes microorganisms which have been genetically modified such that they exhibit an altered or different genotype and/or phenotype (e. g., when the genetic modification affects coding nucleic acid sequences of the microorganism) as compared to the wild type microorganism from which it was derived. A recombinant microorganism comprises at least one recombinant nucleic acid molecule.

The term "recombinant" with respect to nucleic acid molecules refers to nucleic acid molecules produced by man using recombinant nucleic acid techniques. The term comprises nucleic acid molecules which as such do not exist in nature or do not exist in the organism from which the nucleic acid molecule is derived, but are modified, changed, mutated or otherwise manipulated by man. Preferably, a "recombinant nucleic acid molecule" is a non-naturally occurring nucleic acid molecule that differs in sequence from a naturally occurring nucleic acid molecule by at least one nucleic acid. A "recombinant nucleic acid molecules" may also comprise a "recombinant construct" which comprises, preferably operably linked, a sequence of nucleic acid molecules not naturally occurring in that order. Preferred methods for producing said recombinant nucleic acid molecules may comprise cloning techniques, directed or non-directed mutagenesis, gene synthesis or recombination techniques.

Preferably, the biocatalyst for converting (meth-) acrylonitrile to ammonium (meth-) acrylate may be obtained from culturing the microorganism in a suitable growth medium. The growth medium, also called fermentation (culture) medium, fermentation broth, fermentation mixture, or the like, may comprise typical components like sugars, polysaccharides. For storage of the microorganism, the fermentation broth preferably is removed in order to prevent putrefaction, which could result in a reduction of nitrile hydratase activity. Preferably, the storage does not influence biocatalytic activity or does not lead to a reduction in biocatalytic activity. The biocatalyst may be stored in presence of the fermentation broth components. Preferred in the sense of the present invention is that the biocatalyst may be stored in form of a frozen suspension and may be thawed before use. Further, the biocatalyst may be stored in dried form using freeze-drying, spray drying, heat drying, vacuum drying, fluidized bed drying and/or spray granulation.

The biocatalysts that are used according to the present invention can for example be cultured under any conditions suitable for the purpose in accordance with any of the known methods, for instance as described in the mentioned prior art of this specification. The biocatalyst may be used as a whole cell catalyst for the generation of acid from nitrile. The biocatalyst may be (partly) immobilized for instance entrapped in a gel or it may be used for example as a free cell suspension. For immobilization well known standard methods can be applied like for example entrapment cross linkage such as glutaraldehyde-polyethyleneimine (GA-PEI) crosslinking, cross linking to a matrix and/or carrier binding etc., including variations and/or combinations of the aforementioned methods. Alternatively, the nitrilase enzyme may be extracted and for instance may be used directly in the process for preparing the amide. When using inactivated or partly inactivated cells, such cells may be inactivated by thermal or chemical treatment.

In a preferred embodiment, the microorganisms are whole cells. The whole cells may be pre-treated by a drying step. The microorganisms that are employed in the context of the present invention may in a preferred embodiment also be used in an aqueous suspension and in a more preferred embodiment are free whole cells in an aqueous suspension. The term "aqueous suspension" thereby includes all kinds of liquids, such as buffers or culture medium that are suitable to keep microorganisms in suspension. Such liquids are well-known to the skilled person and include for example storage buffers at suitable pH such as storage buffers which are used to store microorganisms, TRIS-based buffers, phosphate based buffers, saline based buffers, water in all quality grades such as distilled water, pure water, tap water, or sea water, culture medium, growing medium, nutrient solutions, or fermentation broths, for example the fermentation broth that was used to culture the microorganisms. During storage for example the aqueous suspension is frozen and thawed before use.

The biocatalyst may be provided as powder, as granulate or as aqueous suspension to the reactor for bioconversion. If provided as powder or granulate it is frequently advisable to prepare an aqueous suspension before adding the catalyst into the reactor/bioconversion unit. In an embodiment, the biocatalyst suspension may be conducted by suspending the biocatalyst powder in water in a vessel comprising at least a mixing device, for example a stirrer, one or more inlets for water, the biocatalyst and optionally further additives and one outlet for the biocatalyst suspension. The volume of the vessel may be for example from 0.1 $m^3$ to 1 $m^3$. The concentration of the biocatalyst in the aqueous biocatalyst suspension may be for example from 1% to 30% by wt., for example from 5 to 15% by wt. relating to the total of all components of the aqueous suspension. A biocatalyst suspension may be added directly to the bioconversion unit. In another embodiment, a concentrated suspension may be diluted before adding it to the bioconversion unit/reactor where the bioconversion takes place.

Bioconversion

The term "bioconversion" as used herein in the context with any one of the methods of the present invention in general denotes a reaction, wherein (meth-) acrylonitrile is converted to ammonium (meth-) acrylate in the presence of aqueous medium and a biocatalyst. As used herein, the term "composition" includes all components present in the reactor, such as, for example, the biocatalyst, (meth-) acrylonitrile, ammonium (meth-) acrylate and water. The composition may also be called reaction mixture.

Particularly, the bioconversion is performed by contacting a mixture comprising aqueous medium and (meth-) acrylonitrile with the biocatalyst. The term "contacting" is not specifically limited and includes for example bringing into contact with, mixing, admixing, shaking, pouring into, flowing into, or incorporating into. It is thus only decisive that the mentioned ingredients come into contact with each other no matter how that contact is achieved.

Aqueous medium comprises all kinds of aqueous liquids, such as buffers at suitable pH, TRIS-based buffers, phosphate based buffers, saline based buffers, water in all quality grades such as distilled water, pure water, tap water, or sea water. The buffer pH is for example in the range of 4 to 9.

Therefore, in one embodiment the present invention relates to a process for producing ammonium (meth-) acrylate, said process comprising the following steps:
(a) adding the following components (i) to (iii) to a reactor to obtain a composition for bioconversion:
 (i) a biocatalyst capable of converting (meth-) acrylonitrile to ammonium (meth-) acrylate;
 (ii) (meth-) acrylonitrile;
 (iii) aqueous medium comprising water; and
(b) performing a bioconversion on the composition obtained in step (a) in a reactor;
wherein the reactor is a relocatable bioconversion unit.

The addition of components (i) to (iii) in step (a) may take place in any order or sequence. Also preparing a pre-mix of some or all components (i) to (iii) is possible to obtain a composition for bioconversion according to step (a). The bioconversion can for example be conducted under any conditions suitable for the purpose in accordance with any of the known methods.

When adding the biocatalyst to the reactor in any one of the methods (process) of the present invention, the biocatalyst may be taken directly from the fermentation broth. Alternatively, in accordance with any one of the methods described herein, the biocatalyst may have been dried before being added to the reactor. In this context the term "before"

does not necessarily mean that the biocatalyst has been dried and is then directly added to the reactor. It is rather sufficient that the biocatalyst has undergone a drying step at any time before it is added to the reactor, independently of whether further steps between the drying and the addition are performed or not. As non-limiting examples, such further steps between the drying step and the addition to the reactor may be storage or reconstitution. However, it is also possible to add the biocatalyst to the reactor directly after drying. According to any one of the methods of the present invention a dried biocatalyst may be added to the reactor. This means that the biocatalyst is added to the reactor in a dried form. In particular, the biocatalyst may have the form of a powder or a granule. As an alternative to adding a dried biocatalyst to the reactor, the dried biocatalyst may be reconstituted before being added to the reactor. For example, the biocatalyst may be reconstituted by suspending in an aqueous composition. With this respect, the aqueous composition may be water or a buffer. As a further alternative, a biocatalyst in form of a matrix bound microorganism may be added to the reactor.

The conversion of (meth-) acrylonitrile to ammonium (meth-) acrylate may be carried out by any of a batch process and a continuous process, and the conversion may be carried out by selecting its reaction system from reaction systems such as suspended bed, a fixed bed, a fluidized bed and the like or by combining different reaction systems according to the form of the catalyst. Particularly, the method of the present invention may be carried out using a semi-batch process. In particular, the term "semi-batch process" as used herein may comprise that an aqueous ammonium (meth-) acrylate solution is produced in a discontinuous manner. In yet another embodiment, the biocatalyst is recovered from the reaction mixture after the bioconversion and re-used in a subsequent bioconversion reaction.

According to a non-limiting example for carrying out such a semi-batch process water, a certain amount of (meth-) acrylonitrile and the biocatalyst are placed in the bioconversion unit. Further (meth-) acrylonitrile is then added during the bioconversion until a desired content of ammonium (meth-) acrylate of the composition is reached. After such desired content of ammonium (meth-) acrylate is reached, the obtained composition is for example partly or entirely recovered from the reactor, before new reactants are placed therein. In particular, in any one of the methods of the present invention the (meth-) acrylonitrile may be fed such that the content of (meth-) acrylonitrile during step (b) is maintained substantially constant at a predetermined value. In general, in any one of the methods of the present invention the (meth-) acrylonitrile content and/or the ammonium (meth-) acrylate content during step (b) may be monitored. Methods of monitoring the contents are not limited and include Fourier Transform Infrared Spectroscopy (FTIR). In another embodiment, the heat-balance of the reaction may be used for monitoring the process. This means that monitoring via heat-balance method takes place by measuring the heat energy of the system during bioconversion and by calculating the loss of heat energy during the reaction in order to monitor the process.

Although the conversion of (meth-) acrylonitrile to the ammonium (meth-) acrylate may preferably be carried out at atmospheric pressure, it may be carried out under pressure in order to increase solubility of acrylonitrile in the aqueous medium. Because biocatalysts are temperature sensitive and the hydrolysis is an exothermic reaction temperature control is important. The reaction temperature is not specifically restricted provided that it is not lower than the freezing point of the aqueous medium. However, it is desirable to carry out the bioconversion at a temperature of usually 0 to 50° C., preferably 10 to 40° C., more preferably 15 to 30° C. It is possible that the temperature may vary over time during the bioconversion reaction. Further suitable conditions for the bioconversion according to the present invention are for example at least 15° C., at least 20° C., at least 24° C. or at least 28° C. Preferably the aqueous medium with the composition for bioconversion is incubated between including 27° C. and 33° C., more preferably the aqueous medium is incubated between including 28° C. and 30° C. Most preferably the aqueous medium is incubated at 28° C. The aqueous medium may also be incubated at 38° C., 39° C., 40° C., 41° C., 42° C., 43° C., 44° C., 45° C., 46° C., 47° C., 48° C., 49° C. or 50° C.

At the start of the process of the invention, the aqueous medium may comprise at least 0.05% (meth-) acrylonitrile, preferably at least 0.1% (meth-) acrylonitrile, more preferably at least 0.5% (meth-) acrylonitrile, most preferably at least 1.0% (meth-) acrylonitrile (w/w). Throughout the bioconversion (incubation) the concentration of (meth-) acrylonitrile may be kept at a concentration of about 0.5% to 1.5%, preferably about 1.0% (meth-) acrylonitrile by continuous feeding of (meth-) acrylonitrile. Alternatively, the concentration of (meth-) acrylonitrile in the aqueous medium may be 5% or 6% at the start of the incubation and might be kept at that concentration or no further (meth-) acrylonitrile may be added during bioconversion (incubation).

It is preferred, that the concentration of (meth-) acrylonitrile during the bioconversion should not exceed 6% by wt. and may for example be in the range from 0.1% by wt. to 6% by wt., preferably from 0.2% by wt. to 5% by wt., more preferably from 0.3% by wt. to 4% by wt., even more preferably from 0.5% by wt. to 3% by wt., still more preferably from 0.8% by wt. to 2% by wt. and most preferably from 1% by wt. to 1.5% by wt., relating to the total of all components of the aqueous mixture. It is possible that the concentration may vary over time during the bioconversion reaction. In order to obtain more concentrated solutions of ammonium (meth-) acrylate the total amount of (meth-) acrylonitrile should not be added all at once but it should be added stepwise or even continuously keeping the abovementioned concentration limits in mind.

The concentration of ammonium (meth-) acrylate in the obtained solution (aqueous medium) is in the range from 10% to 80%, preferably in the range from 20% to 70%, more preferably in the range from 30% to 65%, even more preferably in the range from 40% to 60%, most preferably in the range from 45% to 55% by weight, based on the complete weight of the reaction solution. The reaction should be carried out in such a manner that the final concentration of (meth-) acrylonitrile in the final ammonium (meth-) acrylate solution obtained does not exceed 0.1% by weight relating to the total of all components of the aqueous solution.

Typical reaction times may be from 2 h to 20 h, in particular 4 h to 12 h, for example 6 h to 10 h. After completion of the addition of (meth-) acrylonitrile, the reactor contents are allowed to further circulate for some time to complete the reaction, for example for 1 hour to 3 hours. The remaining contents of (meth-) acrylonitrile should preferably be less than 100 ppm, based on the complete weight of the reaction solution. Further preferred bioconversion times (incubation times) of the aqueous medium may be at least 5 h, at least 10 h or at least 12 h. Preferably the bioconversion (incubation) time is at least 18 h, for example about 24 h or about 30 h. More preferably the bioconversion (incubation) time is about 36 h or about 42 h. Most preferably, the bioconversion (incubation) time is about 48 h. Depending on the nitrilase used and the reaction rate of said nitrilase, the bioconversion (incubation) time may also exceed 48 h.

The present invention further relates to aqueous ammonium (meth-) acrylate solutions obtainable or being obtained by any one of the methods described and provided herein. An aqueous ammonium (meth-) acrylate solution, in particular an aqueous ammonium (meth-) acrylate solution obtainable or being obtained by any one of the methods described herein, may have a concentration of ammonium (meth-) acrylate at the end of the bioconversion of at least 10% (w/w), at least 15% (w/w), at least 20% (w/w), at least 25% (w/w), at least 30% (w/w), at least 35% (w/w), preferably at least 40% (w/w), at least 45% (w/w), more preferably at least 50% (w/w), more preferably at least 51% (w/w), more preferably at least 52% (w/w), more preferably at least 53% (w/w), even more preferably at least 54% (w/w), most preferably at least 55% (w/w) by weight of the ammonium (meth-) acrylate monomers in the aqueous medium.

In any one of the aqueous ammonium (meth-) acrylate solutions, the ammonium (meth-) acrylate content concentration may be determined using HPLC.

Bioconversion Unit

The hydrolysis of (meth-) acrylonitrile to ammonium (meth-) acrylate by means of a biocatalyst is performed in a suitable bioconversion unit (also called reactor). Suitable reactors for performing the bioconversion are known to the skilled artisan. Examples comprise vessels of any shape, for example cylindrical or spherical vessels, or tube reactors. Such reactors comprise particularly a pumping circuit comprising a heat-exchanger.

The bioconversion unit comprises a reaction vessel. The volume of the reaction vessel is not specifically limited and may range from 10 $m^3$ to 150 $m^3$, for example it may be from about 20 $m^3$ to about 120 $m^3$, suitably from about 20 $m^3$ to about 100 $m^3$, preferably about 20 $m^3$ to 50 $m^3$. Preferably, the reaction vessel should be double walled and should be horizontal. Such a construction avoids installing a pit for the collection of any leakage thereby ensuring an easier and quicker relocation of the reaction unit.

The bioconversion unit furthermore comprises means for controlling the temperature of the contents of the vessel. The hydrolysis of (meth-) acrylonitrile to ammonium (meth-) acrylate is an exothermal reaction and therefore heat generated in course of the reaction should be removed in order to maintain an optimum temperature for bioconversion. The bioconversion unit furthermore usually comprises means for measurement and control, for example means for controlling the temperature or for controlling the pressure in the vessel.

For temperature control, the preferred bioconversion unit comprises an external temperature control circuit comprising a pump which pumps the aqueous reactor contents from the storage vessel through a heat exchanger and back into the storage vessel, preferably via an injection nozzle.

In one embodiment, a separate, relocatable temperature control unit is used comprising pump and heat exchanger and which is connected with the bioconversion unit by pipes or flexible tubes. In a preferred embodiment, the temperature control circuit is integrated into the bioconversion unit. It may—for example—be located at one end of the unit next to the reaction vessel.

It has been found, that the external temperature control circuit described above may also be used as means for mixing. The stream of the aqueous reaction mixture which passes through the temperature control circuit and which is injected back into the reaction vessel causes a circulation of the aqueous reaction mixture within the reaction vessel which is sufficient to mix the aqueous reaction mixture.

Preferably, no stirrer is used for the mobile bioconversion unit (i.e. reaction vessel). A stirrer is an additional mechanical device, which increases the technical complexity. When using the external temperature control cycle for mixing instead of a stirrer, the technical complexity can be reduced while still sufficient mixing during bioconversion can be ensured. Advantageously, without a stirrer a transportation step is easier, since no stirrer as additional technical component has to be removed before transportation of the mobile bioconversion unit. Further, a bioconversion unit without a stirrer offers more flexibility in form, shape, mechanical stability requirements and size for the bioconversion unit. In particular, a horizontal set-up for the relocatable bioconversion unit can be realized easier without a stirrer and with mixing just via the external temperature control cycle.

Having no stirrer in the bioconversion reactor offers the advantage of reduced engineering costs and less effort in process control. A further advantage is that with having difficult construction requirements for constructing a bio ammonium (meth-) acrylate production unit, with the present invention the bioconversion manufacturing unit can be built much simpler, with less effort and leads to a less complex bioconversion reactor construction. Based on the state of the art, if bioconversion reactors are not vertical designed but horizontal, this would require more stirrer.

Advantageously, with the present invention and mixing by the external cooling circuit, stirrers are no longer needed. Unexpectedly, the external cooling circuit is sufficient also with horizontal and/or vertical reactors to obtain a satisfactory mixture of the reaction composition/reaction mixture. It is possible to do mixing without a stirrer when producing ammonium (meth-) acrylate from (meth-) acrylonitrile by a biocatalyst method. Additionally, the reduced equipment complexity offers the possibility to conduct the bioconversion in a relocatable unit.

Adding (meth-) acrylonitrile to the contents of the bioconversion unit may be performed in various ways. It may be added into the reaction vessel or it may be added into the temperature control circuit, for example after the pump and before the heat exchanger or after the heat exchanger. Injecting (meth-) acrylonitrile into the temperature control circuit ensures good mixing of the reaction mixture with freshly added (meth-) acrylonitrile. Preferably, (meth-) acrylonitrile is added between pump and heat exchanger.

The amount of reaction mixture cycled per hour through the temperature control circuit is chosen such that sufficient mixing to the contents of the reactor as well as sufficient temperature control is achieved. In one embodiment, the amount of reaction mixture cycled per hour through the temperature control circuit may be from 100% to 1000% of the total volume of the reaction mixture in the bioconversion unit, in particular from 200% to 1000% and for example from 500% to 800%. Further possible is that the amount of reaction mixture cycled per hour through the temperature control circuit is from 100% to 10000%, preferably from 100% to 5000%.

Off-gases of the bioconversion unit may comprise acrylonitrile, acrylic acid and acrylamide. If necessary, according to the applicable rules such off-gases may be treated in a manner known in the art. For example, it may be possible to combust the off-gases.

In one embodiment, all off-gases containing acrylonitrile, acrylic acid and acrylamide may be washed in a scrubber. The scrubber vessel may have a volume of 1 m³ to 100 m³, preferably a volume of 5 m³ to 100 m³, more preferably a volume of 10 m³ to 100 m³. It may be for example an ISOtank or relocatable storage vessel, preferably a double walled vessel. The scrubber water may preferably be collected in a tank and it may be re-used for next bioconversion batch.

In another embodiment of the invention, for temperature control an external temperature control circuit, for example a cooling circuit is used, which comprises a pump which pumps the monomer from the storage vessel through a heat exchanger and back into the storage vessel.

The temperature control circuit may be a separate, relocatable temperature control unit comprising pump and heat exchanger and which is connected with the storage vessel by pipes or flexible tubes.

Modular, Relocatable Units

In one embodiment of the invention, aqueous solutions of bio ammonium (meth-) acrylate for use in the method according to the present invention may be manufactured at a fixed chemical plant, and may be shipped to another location for further processing. However, in another preferred embodiment of the present invention the manufacture of bio ammonium (meth-) acrylate may be performed in a modular, relocatable plant. Further preferred is for example a relocatable bioconversion unit, which can be combined with installations and/or units of a fixed chemical plant. Such combination of an existing plant with a modular, relocatable bioconversion unit offers flexibility in building a production line based on case specific needs. Such production line at a certain plant can be adjusted easily in case the production requirements change. The existing plant for example may be a fixed polymerization plant for homopolymers of (meth-) acrylic acid and/or copolymers of for example (meth-) acrylic acid and acrylamide. So, the combination of a relocatable bioconversion unit offers the possibility of combining the manufacturing of bio ammonium (meth-) acrylate with units for further processing the ammonium (meth-) acrylate obtained from a relocatable bioconversion unit.

Particularly, in the light of the present invention it is possible to reduce the food print and complexity of the bio ammonium (meth-) acrylate manufacturing site. Having a bioconversion reactor without a stirrer/no agitating element reduces the engineering and processing control significantly. Further, no drying, cleaning and/or separation (e.g. centrifugation) facility for ammonium (meth-) acrylate is needed. The obtained aqueous ammonium (meth-) acrylate solution can be used directly for further processing. Therefore, in a preferred embodiment of the invention, the bioconversion unit/bioconversion reactor is a relocatable bioconversion unit. In one embodiment, the relocatable bioconversion unit is similar to the storage unit for (meth-) acrylonitrile, which also may be relocatable. Therefore, it is possible to using largely the same equipment for storing the (meth-) acrylonitrile and for the bioconversion step. This contributes to an economic process for manufacturing aqueous ammonium (meth-) acrylate solutions.

Due to the flexibility of having a relocatable bioconversion unit/bioconversion reactor without a mechanical stirrer/agitating device and without installations for cleaning and/or drying, it is possible to conduct the method for production of an aqueous ammonium (meth-) acrylate solution at the location where the further processing for example to a polymer takes place.

Manufacturing bio ammonium (meth-) acrylate directly at the site of further processing the ammonium (meth-) acrylate to for example polyacrylic acids saves significant transport costs. (Meth-) acrylonitrile is a liquid and may be transported as pure compound to the site of further processing. The molecular weight of ammonium (meth-) acrylate is about 30 to 40% higher than that of (meth-) acrylonitrile and ammonium (meth-) acrylate is typically provided as about 50% aqueous solution. So, for a 50% aqueous solution of ammonium (meth-) acrylate the mass to be transported is about 2.5-fold as much as compared to transporting pure (meth-) acrylonitrile. Transporting pure, solid acrylic acid means transporting only about 30 to 40% more mass as compared to transporting pure (meth-) acrylonitrile, however, additional equipment for handling and dissolving the solid (meth-) acrylic acid is necessary at the location where further processing takes place.

Furthermore, (meth-) acrylic acid is caustic and it is therefore an advantage to reduce the transportation distance or amount of (meth-) acrylic acid to be transported in order to reduce the risk of accidents when transporting acrylic acid. A bioconversion according to the present invention in a relocatable bioconversion unit enables that advantage.

(Meth-) acrylonitrile for bio-catalysis may be stored in one or more than one relocatable storage units. The storage unit comprises a storage vessel. The volume of the storage vessel is not specifically limited and may range from 50 m³ to 150 m³, for example it may be about 100 m³. Preferably, the storage vessel should be single walled or double walled and should be horizontal. Such a construction avoids installing a pit for the collection of any leakage thereby ensuring an easier and quicker relocation of the storage unit. Single walled or double-walled vessels may be placed on every good bearing soil. The storage unit furthermore comprises means for charging and discharging the vessel, means for controlling the pressure in the vessel, for example a valve for settling low-pressure or overpressure, and means for controlling the temperature of the (meth-) acrylonitrile which preferably should not exceed 25° C. It furthermore may comprise means for measurement and control to the extent necessary.

Examples of relocatable storage units comprise relocatable cuboid, storage tanks, preferably double-walled tanks or single walled tanks. Further, any considerable form, shape and size of container is suitable and applicable for the storage and/or provision of acrylonitrile in the sense of the present invention. Particularly, standard iso-tanks are applicable for the storage and/or provision of (meth-) acrylonitrile. Other examples comprise tank containers having a cuboid frame, preferably a frame according to the ISO 668 norm mentioned above and one or more storage vessels mounted into the frame. Such normed tank containers may be stacked and transported on trucks, railcars or ships in the same manner closed intermodal containers.

Several different relocatable units may be bundled together to have a relocatable plant. Each relocatable unit may have certain functions. Examples of such relocatable units comprise units for storing and optionally cooling monomers and/or other raw materials, hydrolyzing (meth-) acrylonitrile, mixing monomers, further processing the ammonium (meth-) acrylate to for example an aqueous solution of a copolymer of (meth-) acrylic acid and acrylamide. For performing different processes, individual units may be connected with each other in a suitable manner thereby obtaining a production line. Also bundling a relocatable bioconversion unit with non-relocatable units is possible.

"Relocatable unit" means that the unit is transportable basically as a whole and that is it not necessary to disassemble the entire unit into individual parts for transport. Transport may happen on trucks, railcars or ships.

In one embodiment, such modular, relocatable units are containerized units which may be transported in the same manner as closed intermodal containers for example on trucks, railcars or ships. Intermodal containers are large standardized (according to ISO 668) shipping containers, in particular designed and built for intermodal freight transport. Such containers are also known as ISO containers. Such ISO containers may have external dimensions of a height of ~2.59 m, a width of ~2.44 m and a length of ~6.05 m. Larger ISO containers have external dimensions of a height of ~2.59 m, a width of ~2.44 m and a length of ~12.19 m.

In another embodiment, the relocatable units are combined, thereby obtaining modular production plants for performing different processes according to the present invention. Such a modular construction using relocatable units provides the advantage, that the plants may be easily relocated if aqueous ammonium (meth-) acrylate solutions are no longer needed at one location but at another location.

At the site of manufacturing the aqueous ammonium (meth-) acrylate solution, at the site of further processing the ammonium (meth-) acrylate to obtain subsequent further products (e.g. poly (meth-) acrylate) and/or at the site of applying/using for example aqueous solutions of (meth-) acrylic acid/acrylamide copolymers (e.g. for oilfield or mining applications) different relocatable units according to the present invention may be used and combined, for example:
- a relocatable storage unit for (meth-) acrylonitrile,
- a relocatable bioconversion unit for hydrolyzing (meth-) acrylonitrile in water in the presence of a biocatalyst capable of converting (meth-) acrylonitrile to ammonium (meth-) acrylate,
- a relocatable unit for removing the biocatalyst from an aqueous ammonium (meth-) acrylate solution,
- a relocatable storage unit for an aqueous ammonium (meth-) acrylate solution,
- relocatable units for further processing ammonium (meth-) acrylate with other water-soluble, monoethylenically unsaturated monomers different from (meth-) acrylic acid,
- a relocatable unit for polymerization to obtain aqueous solutions of (meth-) acrylic acid homo- or copolymers, and/or
- a relocatable unit for subsequent applications.

Further Processing of Ammonium (Meth-) Acrylate

After having obtained the aqueous ammonium (meth-) acrylate solution further processing is possible. Further processing steps are mixing the aqueous ammonium (meth-) acrylate solution with other monomers in order to prepare a monomer solution which is suitable for a subsequent polymerization step to obtain homopolymers or copolymers deriving from ammonium (meth-) acrylate. Further processing also comprises processing the obtained ammonium (meth-) acrylate to other acrylic monomers or to produce acrylic acid or salts thereof (e.g. sodium acrylate) to be used for instance as a polymerizable monomer. Due to the benefits of a bioconversion reaction (particularly, without a stirrer or without mechanical agitation device) it is in particular possible to use the bioconversion reactor as make-up and/or storage device for a monomer solution, which could subsequently be used for a polymerization reaction. The different further processing steps may be performed at different locations. For example, each further processing step may be performed at a different location. Alternatively, all or some of the further processing steps may be performed at the same location, in particular at the location of use of either the aqueous ammonium (meth-) acrylate solution or at the location of use of the resulting polymer solution. If performed at the same location, it is possible to connect the different modular units/modular reactors with each other as needed to perform for example the different steps comprising the bioconversion of (meth-) acrylonitrile to ammonium (meth-) acrylate and subsequent preparation of a monomer solution and polymerization to obtain homo- or copolymers of (meth-) acrylic acid directly after another.

Biomass Removal

After bioconversion, the reaction vessel comprises an aqueous solution of ammonium (meth-) acrylate, which still comprises the biocatalyst suspended therein. The biocatalyst preferably becomes removed completely, essentially completely, or partially before polymerization, however, removing the biocatalyst may not be absolutely necessary in every case. Whether it is necessary to remove the biocatalyst substantially depends on two factors, namely whether remaining biocatalyst negatively affects polymerization and/or the properties of the polymer obtained and/or the biocatalyst negatively affects the application of the obtained polymer solution. In one embodiment, at least 75%, preferably at least 90% by weight of the biomass-relating to the total of the biomass present-should be removed.

The method for removing the biocatalyst is not specifically limited. Separation of the biocatalyst may take place by for example filtration or centrifugation. In other embodiments, active carbon may be used for separation purpose.

Procedurally, for removing the biocatalyst there are several options.

In one embodiment, the aqueous ammonium (meth-) acrylate solution comprising the biocatalyst is removed from the bioconversion unit, passed through a unit for removing the biocatalyst, and thereafter the aqueous ammonium (meth-) acrylate solution is filled into a suitable storage unit for ammonium (meth-) acrylate, for example a relocatable storage unit for ammonium (meth-) acrylate as described above.

In another embodiment, the aqueous ammonium (meth-) acrylate solution comprising the biocatalyst is removed from the bioconversion unit, passed through a unit for removing the biocatalyst and thereafter the aqueous ammonium (meth-) acrylate solution is filled directly into a monomer make-up unit for further processing, i.e. without intermediate storing in an ammonium (meth-) acrylate storage unit.

In another embodiment, the aqueous ammonium (meth-) acrylate solution comprising the biocatalyst is removed from the bioconversion unit and is filled directly, i.e. without removing the biocatalyst, into the monomer make-up unit. In said embodiment, the biocatalyst is still present in course of monomer make-up for further processing and is removed after preparing an aqueous monomer solution.

In another embodiment it is even possible that the biocatalyst is not removed from the aqueous monomer solution and the biocatalyst is present during further processing. This non-removal of the biocatalyst is of advantage, because the processing step of removing the biocatalyst can be avoided which therefore leads to less process steps and makes the overall process simpler.

In another embodiment, the aqueous ammonium (meth-) acrylate solution comprising the biocatalyst is removed from the bioconversion unit, passed through a unit for removing the biocatalyst and thereafter filled back into the bioconversion unit. In order to ensure complete discharge of the bioconversion unit before re-filling it, the unit for removing the biocatalyst should comprise a buffer vessel having a volume sufficient for absorbing the contents of the bioconversion unit.

The above-mentioned methods for biocatalyst removal are for example applicable for partwise and/or complete removal of the biocatalyst. Further, it is preferred, that the completely or partly removed biocatalyst may be reused for a subsequent bioconversion reaction.

In a preferred embodiment, the aqueous ammonium (meth-) acrylate solution does no longer comprise the biocatalyst. However, in another embodiment the ammonium (meth-) acrylate solution still comprises the biomass. In said embodiment, the biocatalyst may be removed after preparing an aqueous monomer solution for further processing in the same manner as described above or it may not be removed. Criteria for deciding in which cases it may not be necessary to remove the biocatalyst have already been mentioned above.

Provision of Acrylamide

In the context of the present invention, acrylamide may be used as comonomer besides (meth-) acrylic acid. Basically, any kind of acrylamide may be used for the process according to the present invention, for example acrylamide obtained by catalytic oxidation of propene. It is also possible to use crude acrylamide, which has not been purified. In one embodiment of the invention acrylamide available by enzymatic hydrolysis of acrylonitrile may be used for carrying out the process according of the present invention (hereinafter also "bio acrylamide"). In a preferred embodiment of the present invention the manufacture of acrylamide by enzymatic hydrolysis of acrylonitrile is also performed in a modular/relocatable bioconversion unit. Suitable enzymes have been disclosed in the literature (e.g. WO 2005054456, WO 2005054489), and the publications describes also suitable conditions for carrying out the reaction. The manufacture of bio acrylamide may be carried out using stirred tank reactors or loop reactors, and in particular, the relocatable bioconversion unit described above may also be used. Manufacturing bio-acrylamide at the same location as manufacturing ammonium (meth-) acrylate also saves transport costs. Further beneficial is that for enzymatic production of acrylamide and ammonium (meth-) acrylate the same starting material, namely (meth-) acrylonitrile, can be used, which offers advantages regarding sourcing and transportation.

Aqueous Monomer Solution

In course of further processing, an aqueous monomer solution comprising at least water, ammonium (meth-) acrylate and optionally further water-soluble, monoethylenically unsaturated monomers is prepared. Basically, the kind and amount of water-soluble, monoethylenically unsaturated comonomers to be used besides acrylic acid is not limited and depends on the desired properties and the desired use of the aqueous solutions of poly (meth-) acrylates to be manufactured. Typical monomers fall under the definitions of neutral comonomers, anionic comonomers, cationic comonomers and/or associative comonomers, which an artisan knows from the state of the art and is also applicable in the context of the present invention.

Examples of neutral comonomers are comprising hydroxyl and/or ether groups, for example hydroxyethyl (meth)acrylate, hydroxypropyl(meth)acrylate, allyl alcohol, hydroxyvinylethylether, hydroxyvinylpropylether, hydroxyvinylbutylether, polyethylene glycol (meth)acrylate, N-vinylformamide, N-vinylacetamide, N-vinylpyrrolidone or N-vinylcaprolactam, and vinyl esters, for example vinylformate or vinyl acetate. Examples of neutral comonomers also comprise acrylamide, methacrylamide, N-methyl(meth)acrylamide, N,N'-dimethyl(meth)acrylamide, N-methylol (meth)acrylamide. Preference is given to acrylamide, methacrylamide, N-vinylpyrrolidone.

Examples of anionic comonomers may be selected from water-soluble, monoethylenically unsaturated monomers comprising at least one acidic group, or salts thereof. The acidic groups are preferably selected from the group of $-COOH$, $-SO_3H$ and $-PO_3H_2$ or salts thereof. Preference is given to monomers comprising COOH groups and/or $-SO_3H$ groups or salts thereof. Suitable counterions include especially alkali metal ions such as $Li^+$, $Na^+$ or $K^+$, and also ammonium ions such as $NH_4^+$ or ammonium ions having organic radicals. Examples of ammonium ions having organic radicals include $[NH(CH_3)_3]^+$, $[NH_2(CH_3)_2]^+$, $[NH_3(CH_3)]^+$, $[NH(C_2H_5)_3]^+$, $[NH_2(C_2H_5)_2]^+$, $[NH_3(C_2H_5)]^+$, $[NH_3(CH_2CH_2OH)]^+$, $[H_3N-CH_2CH_2-NH_3]^{2+}$ or $[H(H_3C)_2N-CH_2CH_2CH_2NH_3]^{2+}$.

Examples of anionic comonomers comprising $-COOH$ groups include crotonic acid, itaconic acid, maleic acid or fumaric acid or salts thereof. Examples of comonomers comprising $-SO_3H$ groups or salts thereof include vinylsulfonic acid, allylsulfonic acid, 2-acrylamido-2-methylpropanesulfonic acid (ATBS), 2-methacrylamido-2-methylpropanesulfonic acid, 2-acrylamidobutanesulfonic acid, 3-acrylamido-3-methylbutanesulfonic acid or 2-acrylamido-2,4,4-trimethylpentanesulfonic acid. Preference is given to 2-acrylamido-2-methylpropanesulfonic acid (ATBS) or salts thereof. Examples of monomers comprising $-PO_3H_2$ groups or salts thereof include vinylphosphonic acid, allylphosphonic acid, N-(meth)acrylamidoalkylphosphonic acids or (meth)acryloyloxyalkylphosphonic acids, preferably vinylphosphonic acid.

Examples of cationic comonomers may be selected from water-soluble, monoethylenically unsaturated monomers comprising cationic groups. Suitable cationic monomers include especially monomers having ammonium groups, especially ammonium derivatives of N-(ω-aminoalkyl) (meth)acrylamides or ω-aminoalkyl(meth)-acrylates such as 2-trimethylammonioethyl acrylate chloride $H_2C=CH-CO-CH_2CH_2N+(CH_3)_3$ $Cl^-$ (DMA3Q). Further examples have been mentioned in WO 2015/158517 A1 page 8, lines 15 to 37. Preference is given to DMA3Q.

Associative monomers impart hydrophobically associating properties to polyacrylates and/or polyacrylamides. Associative monomers to be used in the context of this invention are water-soluble, monoethylenically unsaturated monomers having at least one hydrophilic group and at least one, preferably terminal, hydrophobic group. Examples of associative monomers have been described for example in WO 2010/133527, WO 2012/069478, WO 2015/086468 or WO 2015/158517. "Hydrophobically associating copolymers" are understood by a person skilled in the art to mean water-soluble copolymers which, as well as hydrophilic units (in a sufficient amount to assure water solubility), have hydrophobic groups in lateral or terminal positions. In aqueous solution, the hydrophobic groups can associate with one another. Because of this associative interaction, there is an increase in the viscosity of the aqueous polymer solution compared to a polymer of the same kind that merely does not have any associative groups.

Examples of suitable associative monomers comprise monomers having the general formula $H_2C=C(R^1)-R^2-R^3$ (I) wherein $R^1$ is H or methyl, $R^2$ is a linking hydrophilic group and $R^3$ is a terminal hydrophobic group. Further examples comprise having the general formula $H_2C=C$ $(R^1)$—$R^2$-$R^3$—$R^4$ (II) wherein $R^1$, $R^2$ and $R^3$ are each as defined above, and $R^4$ is a hydrophilic group.

The linking hydrophilic $R^2$ group may be a group comprising ethylene oxide units, for example a group comprising 5 to 80 ethylene oxide units, which is joined to the $H_2C=C(R^1)$— group in a suitable manner, for example by means of a single bond or of a suitable linking group. In another embodiment, the hydrophilic linking group $R^2$ may be a group comprising quaternary ammonium groups.

In one embodiment, the associative monomers are monomers of the general formula $H_2C=C(R^1)$—O—$(CH_2CH_2O)_k$—$R^{3a}$ (III) or $H_2C=C(R^5)$—(C=O)—O—$(CH_2CH_2O)_k$—$R^{3a}$ (IV), wherein $R^1$ has the meaning defined above and k is a number from 10 to 80, for example, 20 to 40. $R^{3a}$ is an aliphatic and/or aromatic, straight-chain or branched hydrocarbyl radical having 8 to 40 carbon atoms, preferably 12 to 32 carbon atoms.

Examples of such groups include n-octyl, n-decyl, n-dodecyl, n-tetradecyl, n-hexadecyl or n-octadecyl groups. In a further embodiment, the groups are aromatic groups, especially substituted phenyl radicals, especially distyrylphenyl groups and/or tristyrylphenyl groups.

In another embodiment, the associative monomers are monomers of the general formula $H_2C=C(R^1)$—O—$(CH_2)_n$—O—$(CH_2CH_2O)_x$—$(CH_2$—$CH(R^5)O)_y$—$(CH_2CH_2O)_zH$ (V), wherein $R^1$ is defined as above and the $R^5$ radicals are each independently selected from hydrocarbyl radicals comprising at least 2 carbon atoms, preferably from ethyl or propyl groups. In formula (V) n is a natural number from 2 to 6, for example 4, x is a number from 10 to 50, preferably from 12 to 40, and for example, from 20 to 30 and y is a number from 5 to 30, preferably 8 to 25. In formula (V), z is a number from 0 to 5, for example 1 to 4, i.e. the terminal block of ethylene oxide units is thus merely optionally present. In an embodiment of the invention, it is possible to use at least two monomers (V), wherein the $R^1$ and $R^5$ radicals and indices n, x and y are each the same, but in one of the monomers z=0 while z>0 in the other, preferably 1 to 4.

In another embodiment, the associative monomers are cationic monomers. Examples of cationic associative monomers have been disclosed in WO 2015/158517 A1, page 11, line 20 to page 12, lines 14 to 42. In one embodiment, the cationic monomers having the general formula $H_2C=C(R^1)$—C(=O)O—$(CH_2)_k$—$N^+(CH_3)(CH_3)(R^6)$ $X^-$ (VI) or $H_2C=C(R^1)$—C(=O)N($R^1$)—$(CH_2)_k$—$N^+(CH_3)(CH_3)(R^6)$ $X^-$ (VII) may be used, wherein $R^1$ has the meaning as defined above, k is 2 or 3, $R^6$ is a hydrocarbyl group, preferably an aliphatic hydrocarbyl group, having 8 to 18 carbon atoms, and $X^-$ is a negatively charged counterion, preferably $Cl^-$ and/or $Br^-$.

Besides water-soluble monoethylenically unsaturated monomers, also water-soluble, ethylenically unsaturated monomers having more than one ethylenic group may be used as further comonomers. Monomers of this kind can be used in special cases in order to achieve easy crosslinking of the polymers. The amount thereof should generally not exceed 2% by weight, preferably 1% by weight and especially 0.5% by weight, based on the sum total of all the monomers. More preferably, the monomers to be used in the present invention are only monoethylenically unsaturated monomers.

Besides the monomers, further additives and auxiliaries may be added to the aqueous monomer solution. Furthermore, before polymerization also suitable initiators for radical polymerization may be added. Examples of such further additives and auxiliaries comprise complexing agents, defoamers, surfactants, stabilizers, and bases or acids for adjusting the pH value. In certain embodiments of the invention, the pH-value of the aqueous monomer solution is adjusted to values from pH 5 to pH 7, for example pH 6 to pH 7. Preferably, it is also possible that the pH adjustment takes place in-situ, which means that via adjusting the acrylic acid content in the aqueous monomer solutions the pH can be adjusted. This adjustment can take place directly without addition of further pH adjusting additives during the reaction. This adjustment can also take place directly during the reaction by addition of for example a suitable buffer.

In one embodiment, the aqueous monomer solution comprises at least one stabilizer for the prevention of polymer degradation. Such stabilizers for the prevention of polymer degradation are what are called "free-radical scavengers", i.e. compounds which can react with free radicals (for example free radicals formed by heat, light, redox processes), such that said radicals can no longer attack and hence degrade the polymer. Using such kind of stabilizers for the stabilization of aqueous solutions of polyacrylates and/or polyacrylamides basically is known in the art, as disclosed for example in WO 2015/158517 A1, WO 2016/131940 A1, or WO 2016/131941 A1.

The stabilizers may be selected from the group of non-polymerizable stabilizers and polymerizable stabilizers. Polymerizable stabilizers comprise a monoethylenically unsaturated group and become incorporated into the polymer chain in course of polymerization. Non-polymerizable stabilizers don't comprise such monoethylenically unsaturated groups and are not incorporated into the polymer chain.

In one embodiment of the invention, stabilizers are non-polymerizable stabilizers selected from the group of sulfur compounds, sterically hindered amines, N-oxides, nitroso compounds, aromatic hydroxyl compounds or ketones. Examples of sulfur compounds include thiourea, substituted thioureas such as N,N'-dimethylthiourea, N,N'-diethylthiourea, N,N'-diphenylthiourea, thiocyanates, for example ammonium thiocyanate or potassium thiocyanate, tetramethylthiuram disulfide, and mercaptans such as 2-mercaptobenzothiazole or 2-mercaptobenzimidazole or salts thereof, for example the sodium salts, sodium dimethyldithiocarbamate, 2,2'-dithiobis(benzo-thiazole), 4,4'-thiobis(6-t-butyl-m-cresol). Further examples include dicyandiamide, guanidine, cyanamide, paramethoxyphenol, 2,6-di-t-butyl-4-methylphenol, butylhydroxyanisole, 8-hydroxyquinoline, 2,5-di(t-amyl)-hydroquinone, 5-hydroxy-1,4-naphthoquinone, 2,5-di(t-amyl)hydroquinone, dimedone, propyl 3,4,5-trihydroxy-benzoate, ammonium N-nitrosophenylhydroxylamine, 4-hydroxy-2,2,6,6-tetramethy-oxylpiperidine, (N-(1,3-dimethylbutyl)-N'-phenyl-p-phenylenediamine and 1,2,2,6,6-pentamethyl-4-piperidinol. Preference is given to sterically hindered amines such as 1,2,2,6,6-pentamethyl-4-piperidinol and sulfur compounds, preferably mercapto compounds, especially 2-mercaptobenzothiazole or 2-mercaptobenzimidazole or the respective salts thereof, for example the sodium salts, and particular preference is given to 2-mercaptobenzothiazole or salts thereof, for example the sodium salts. The amount of such non-polymerizable stabilizers—if present—may be from 0.1% to 2.0% by weight, relating to the total of all monomers in the aqueous monomer solution, preferably from 0.15% to 1.0% by weight and more preferably from 0.2% to 0.75% by weight.

In another embodiment of the invention, the stabilizers are polymerizable stabilizers substituted by a monoethylenically unsaturated group. With other words, such stabilizers are also monomers (C). Examples of stabilizers comprising monoethylenically unsaturated groups comprise (meth) acrylic acid esters of 1,2,2,6, -pentamethyl-4-piperidinol or other monoethylenically unsaturated groups comprising 1,2, 2,6,6-pentamethyl-piperidin-4-yl groups. Specific examples of suitable polymerizable stabilizers are disclosed in WO 2015/024865 A1, page 22, lines 9 to 19. In one embodiment of the invention, the stabilizer is a (meth)acrylic acid ester of 1,2,2,6,6-pentamethyl-4-piperidinol. The amount of polymerizable stabilizers—if present—may be from 0.01 to 2% by weight, based on the sum total of all the monomers in the aqueous monomer solution, preferably from 0.02% to 1% by weight, more preferably from 0.05% to 0.5% by weight.

In one embodiment, the aqueous monomer solution comprises at least one non-polymerizable surfactant. Examples of suitable surfactants including preferred amounts have been disclosed in WO 2015/158517 A1, page 19, line, 23 to page 20, line 27. In the manufacture of hydrophobically associating polyacrylamides, the surfactants lead to a distinct improvement of the product properties. If present, such non-polymerizable surfactant may be used in an amount of 0.1 to 5% by weight, for example 0.5 to 3% by weight based on the amount of all the monomers used.

As used herein, the term "water-soluble monomers" in the context of this invention means that the monomers are to be soluble in the aqueous monomer solution to be used for polymerization in the desired use concentration. It is thus not absolutely necessary that the monomers to be used are miscible with water without any gap; instead, it is sufficient if they meet the minimum requirement mentioned. It is to be noted that the presence of acrylamide and/or acrylic acid in the monomer solution might enhance the solubility of other monomers as compared to water only. In general, the solubility of the water-soluble monomers in water at room temperature should be at least 50 g/l, preferably at least 100 g/l.

Besides water, the aqueous monomer solution may also comprise additionally water-miscible organic solvents. However, as a rule the amount of water should be at least 70% by wt. relating to the total of all solvents used, preferably at least 85% by wt. and more preferably at least 95% by wt. In one embodiment, only water is used as solvent.

Depending on the chemical nature, the water-soluble, monoethylenically unsaturated monomers to be used may be provided as pure monomers or as aqueous solutions for further processing. It is also possible to provide a mixture of two or more water-soluble, monoethylenically unsaturated monomers, in aqueous solution or as pure monomers for further processing. Acrylic acid, acrylamide and other water-soluble, monoethylenically unsaturated monomers such as 2-acrylamido-2-methylpropane-sulfonic acid (ATBS), or 2-trimethylammonioethyl acrylate chloride $H_2C=CHCO-CH_2CH_2N^+(CH_3)_3$ $Cl^-$ (DMA3Q), or mixtures thereof preferably may be stored in suitable storage units. The monomers may be provided by road tankers, ISO tanks, or rail cars and pumped into relocatable storage units.

The aqueous monomer solution for polymerization comprises water and 5% to 45% by weight, preferably 15% to 45% by weight of water-soluble, monoethylenically unsaturated monomers, relating to the total of all components of the aqueous monomer solution. The water-soluble, monoethylenically unsaturated monomers comprise at least ammonium (meth-) acrylate, which preferably is manufactured as described above.

In one embodiment of the invention, the monomer concentration is from 8% by weight to 24.9% by weight, preferably from 15% by weight to 24.9% by weight, for example from 20 to 24.9% by weight, relating to the total of all components of the aqueous monomer solution. The monomer concentration may be selected by the skilled artisan according to his/her needs. For preparing the aqueous monomer solution, the water-soluble, monoethylenically unsaturated monomers to be used are mixed with each other. All monomers and optionally additives may be mixed with each other in a single step but it may also be possible to mix some monomers and add further monomers in a second step. Also, water for adjusting the concentration of the monomers may be added. Water eventually used for rinsing lines in course of transferring the monomer solution into the polymerization unit, needs to be taken into consideration when adjusting the concentration.

Preferably, the preparation of the aqueous monomer solution is performed in a relocatable monomer make-up unit. In one embodiment, the monomer make-up may be the unit which is similar to the bioconversion unit as described above. Using largely the same equipment for storing (meth-) acrylonitrile, for the bioconversion step and for further processing ammonium (meth-) acrylate contributes to an economic process for manufacturing aqueous ammonium (meth-) acrylate solutions. It is possible that the bioconversion unit may also be used for monomer make-up.

If the monomer make-up vessel is different to the bioconversion unit, it may be equipped with a stirrer for mixing the components of the aqueous monomer solution with each other. However, in the same manner as with the bioreactor, the external temperature control circuit may be used as means for mixing. The stream of the aqueous monomer mixture which passes through the temperature control circuit and which is injected back into the monomer make-up vessel causes a circulation of the aqueous reaction mixture within the reaction vessel which is sufficient to mix the aqueous reaction mixture.

Polymers

Furthermore, the present invention relates to an (meth-) acrylic acid homopolymer or copolymer obtainable or being obtained by polymerizing the ammonium (meth-) acrylate of the aqueous solution as described herein. With this respect, in case of a homopolymer the term "polymerizing" refers to a homopolymerization reaction, while in case of a copolymer the term "polymerizing" refers to a copolymerization reaction. The homopolymerization or copolymerization may be performed using an aqueous ammonium (meth-) acrylate solution obtainable or being obtained by any one of the methods described herein. Preferably, an aqueous ammonium (meth-) acrylate solution may be used, from which the biocatalyst has been separated prior to the polymerization.

As used herein, the term "poly (meth-) acrylates" and/or "poly (meth-) acrylic acid" as used herein means water-soluble homopolymers of (meth-) acrylic acid, or water-soluble copolymers comprising at least 10%, preferably at least 20%, and more preferably at least 30% by weight of (meth-) acrylic acid and at least one additional water-soluble, monoethylenically unsaturated monomer different from (meth-) acrylic acid, wherein the amounts relate to the total amount of all monomers in the polymer. Copolymers are preferred. Copolymers may for example also comprise terpolymers of three different monomers.

(Meth-) acrylic acid homopolymers are, for example, used as surface coatings, adhesives, sealants, etc. In particular, use of (meth-) acrylic acid/acrylamide copolymers is made in tertiary oil recovery, which is also denoted as enhanced oil recovery. With this respect, in methods of tertiary oil recovery an aqueous solution of the polymer may be injected into the rock in order to promote oil displacement and thus increase the yield of crude oil. The present invention is therefore also related to an aqueous solution of any (meth-) acrylic acid/acrylamide copolymer described herein. As water for the aqueous solution seawater may be used.

Although the invention has been described with respect to specific embodiments and examples, it should be appreciated that other embodiments utilizing the concept of the present invention are possible without departing from the scope of the invention. The present invention is defined by the claimed elements, and any and all modifications, variations, or equivalents that fall within the true spirit and scope of the underlying principles.

FIGURES

The invention is further described by the figures. These are not intended to limit the scope of the invention

DETAILED DESCRIPTION OF THE FIGURE

Figure 1:
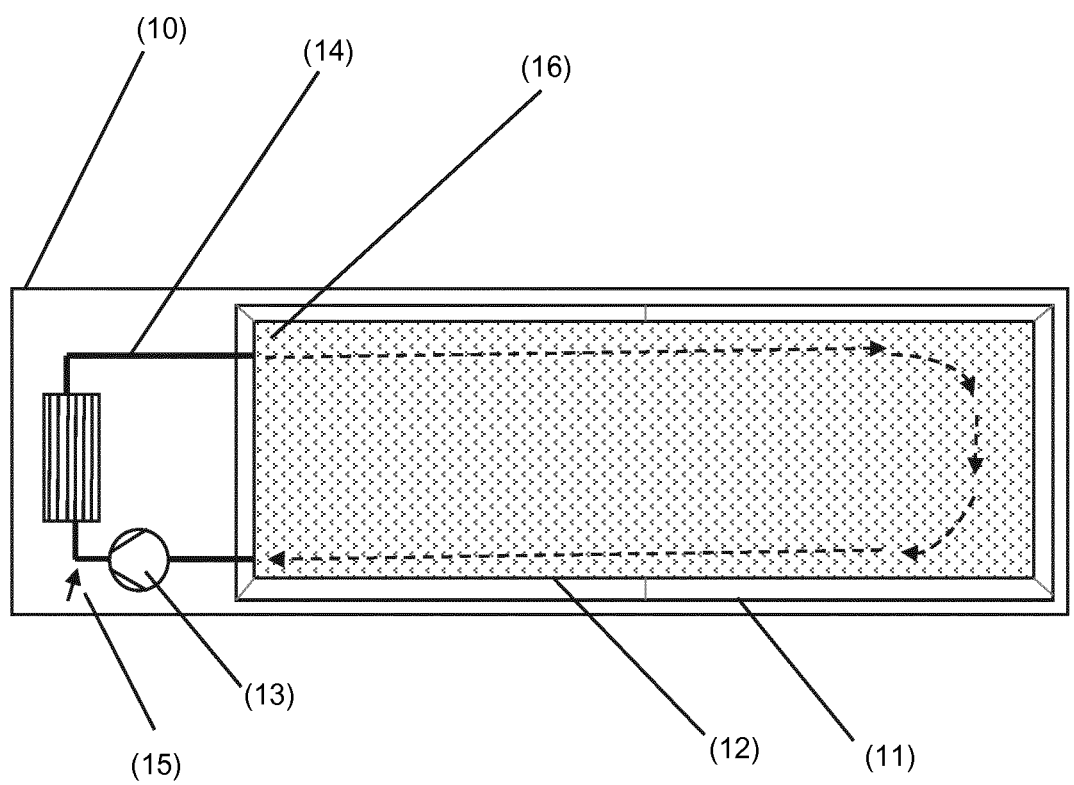
FIG. 1: Schematic representation of a bio ammonium (meth-) acrylate reactor

FIG. 1 schematically represents an embodiment of the relocatable bioconversion unit with an integrated temperature control circuit. The bioconversion unit comprises a frame (10), a double-walled reaction vessel mounted into the frame comprising an outer wall (11) and an inner wall (12). Preferred volumes of the reaction vessel have already been mentioned. In other embodiments, the reaction vessel is self-supporting and there is no frame (10). The reaction vessel is filled with the reaction mixture. The bioconversion unit furthermore comprises an external temperature control circuit comprising at least a pump (13) and a temperature control unit (14). The reaction mixture is circulated by means of a pump (13) from the reaction vessel to the temperature control unit (14) and is injected back into the storage vessel, preferably via an injection nozzle (16). In the depicted embodiment, (meth-) acrylonitrile is injected into the temperature control circuit thereby ensuring good mixing (15). It may be added before or after the temperature control unit. FIG. 1 shows an embodiment in which (meth-) acrylonitrile is added into the temperature control circuit between the pump and the heat exchanger. The stream of reaction mixture injected back into the reaction vessel causes a circulation of the reaction mixture in the reaction vessel which ensures sufficient mixing of the contents of the reaction mixture. No stirrer is installed.

Figure 2:
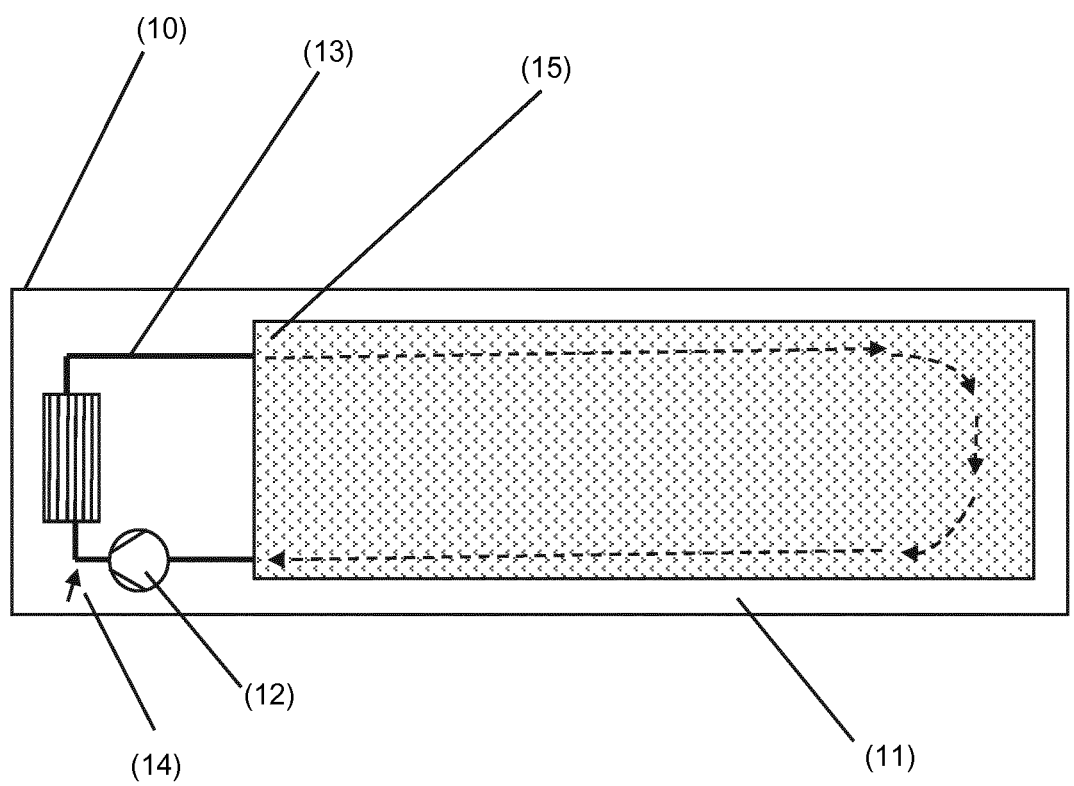
FIG. 2: Schematic representation of a bio ammonium (meth-) acrylate reactor having eight single walled reaction vessel.

FIG. 2 schematically represents an embodiment of the relocatable bioconversion unit with an integrated temperature control circuit. The bioconversion unit comprises a frame (10), a reaction vessel mounted into the frame comprising a single wall (11). Preferred volumes of the reaction vessel have already been mentioned. In other embodiments, the reaction vessel is self-supporting and there is no frame (10). The reaction vessel is filled with the reaction mixture. The bioconversion unit, furthermore, comprises an external temperature control circuit comprising at least a pump (12) and a temperature control circuit (13). The reaction mixture is circulated by means of a pump (12) from the reaction vessel to the temperature control unit (13) and is injected back into the storage vessel, preferably via an injection nozzle (15). In the depicted embodiment, (meth-) acrylonitrile is injected into the temperature control circuit thereby ensuring good mixing (14). It may be added before or after the temperature control unit. No stirrer is installed.

EXAMPLES

The invention is further described by the following examples. The examples relate to practical and in some cases preferred embodiments of the invention that do not limit the scope of the invention.

Example 1 (Comparative)

Copolymer of Purified Ammonium Acrylate and Acrylamide ($NH_4AA/AM$):
Copolymer comprising 70.54 wt. % (75.0 mol %) of acrylamide and 29.46 wt. % (25 mol %) of ammonium acrylate, stabilized with 0.25 wt. % Na-MBT (relating to polymer).

A 5 L beaker with magnetic stirrer, pH meter and thermometer was initially charged with 550.14 g of a 43% aqueous solution of ammonium acrylate (purified/centrifugated), and then the following were added successively: 1800 g of distilled water, 1089.29 g of acrylamide (52% by weight in water, bio acrylamide) 10.5 g of a 5% aqueous solution of diethylenetriaminepentaacetic acid pentasodium salt, and 4 g of a 50% aqueous solution of the stabilizer sodium 2-mercaptobenzothiazole (Na-MBT).

After adjustment to pH 6.4 with a 20% by weight solution of sulfuric acid and addition of the rest of the water to attain the desired monomer concentration of 23% by weight (total amount of water 1824.37 g minus the amount of water already added, minus the amount of acid required), the monomer solution was adjusted to the initiation temperature of 0° C. The solution was transferred to a Dewar vessel, the temperature sensor for the temperature recording was inserted, and the flask was purged with nitrogen for 45 minutes. The polymerization was initiated with 21 g of a 10% aqueous solution of the water-soluble azo initiator 2,2'-azobis(2-methylpropionamidine) dihydrochloride (Wako V-50; 10 h t½ in water 56° C.), 1.75 g of a 1% t-butyl hydroperoxide solution and 1.05 g of a 1% sodium sulfite solution. With the onset of the polymerization, the temperature rose to 60° C. within about 50 min. A solid polymer gel was obtained.

After the polymerization, the gel was incubated overnight at 60° C. and the gel block was comminuted with the aid of a meat grinder. The comminuted aqueous polyacrylamide gel was kept for further testing without drying.

Example 2 (Inventive)

Copolymer of Crude (Unpurified) Ammonium Acrylate and Acrylamide ($cNH_4AA/AM$):
Copolymer comprising 70.54 wt. % (75.0 mol %) of acrylamide and 29.46 wt. % (25 mol %) of crude (unpurified/non-centrifugated) ammonium acrylate (ammonium acrylate is used directly after synthesis without a cleaning step), stabilized with 0.25 wt. % Na-MBT (relating to polymer)

A 1 L screw glass bottle with magnetic stirrer, pH meter and thermometer was initially charged with 62.87 g of a 43% aqueous solution of crude ammonium acrylate, and then the following were added successively: 200 g of distilled water, 124.49 g of acrylamide (52% by weight in water, bio acrylamide) 1.2 g of a 5% aqueous solution of diethylenetriaminepentaacetic acid pentasodium salt, and 0.46 g of a 50% aqueous solution of the stabilizer sodium 2-mercaptobenzothiazole (Na-MBT).

After adjustment to pH 6.4 with a 10% by weight solution of sulfuric acid and addition of the rest of the water to attain the desired monomer concentration of 23% by weight (total amount of water 208.50 g minus the amount of water already added, minus the amount of acid required), the monomer solution was adjusted to the initiation temperature of 0° C. The solution was transferred to Dewar vessel, the temperature sensor for the temperature recording was inserted, and the flask was purged with nitrogen for 45 minutes. The polymerization was initiated with 2.40 g of a 10% aqueous solution of the water-soluble azo initiator 2,2'-azobis(2-methylpropionamidine) dihydrochloride (Wako V-50; 10 h t½ in water 56° C.), 0.20 g of a 1% t-BHP solution and 0.12 g of a 1% sodium sulfite solution. With the onset of the polymerization, the temperature rose to 55° C. within about 120 min. A solid polymer gel was obtained. After the polymerization, the gel was incubated 3 hours at 60° C. The comminuted aqueous polyacrylamide gel was kept for further testing without drying.

Testing

Gel Fraction/Solid Content

A 5000 ppm polymer solution in pH 7 buffer is diluted to 1000 ppm with pH 7 buffer. The gel fraction is given as mL of gel residue on the sieve when 250 g 1000 ppm polymer solution are filtered over 200 μm sieve and consequently washed with 2 l of tab water.

Viscosity of the Polymers in Aqueous Solution

Measurements were performed in "pH 7 buffer": For 10 l of pH 7 buffer fully dissolve 583.3±0.1 g sodium chloride, 161.3±0.1 g disodium hydrogenphosphate·12H$_2$O and 7.80±0.01 g sodium dihydrogenphosphate·2H$_2$O in 10 l dist. or deionized water. A 5000 ppm polymer solution was obtained by dissolving the appropriate amount of aqueous polymer gel in pH 7 buffer until being fully dissolved. Viscosity measurements were performed at a Brookfield RS rheometer with single gap geometry.

Filtration Ratio

Determination of MPFR (Millipore Filtration Ratio)

The filterability of the polymer solutions was characterized using the MPFR value (Millipore filtration ratio). The MPFR value characterizes the deviation of a polymer solution from ideal filtration characteristics, i.e. when there is no reduction of the filtration rate with increasing filtration. Such a reduction of the filtration rate may result from the blockage of the filter in course of filtration.

To determine the MPFR values, about 200 g of the relevant polyacrylamide solution having a concentration of 1000 ppm were filtered through a polycarbonate filter have a pore size of 5 μm at a pressure of 2 bar and the amount of filtrate was recorded as a function of time.

The MPFR value was calculated by the following formula $$\text{MPFR} = (t_{180\,g} - t_{160\,g})/(t_{80\,g} - t_{60\,g}).$$

$T_{x\,g}$ is the time at which the amount solution specified passed the filter, i.e. $t_{180g}$ is the time at which 180 g of the polyacrylamide solution passed the filter. According to API RP 63 ("Recommended Practices for Evaluation of Polymers Used in Enhanced Oil Recovery Operations", American Petroleum Institute), values of less than 1.3 are acceptable.

Long-Term Storage 100 g of the gel was sealed under vacuum in a plastic bag and stored at 60° C. for one week. Subsequently, the gel was cooled tor room temperature and used for further testing.

Results

TABLE 1

| ID | $T_{max}$ [° C.] | Solid content [%] | Viscosity[1] [mPas] | MPFR[2] |
|---|---|---|---|---|
| Example 1 (comparative) | 58.4 | 24.72 | 65 | 1.15 |
| Example 2 (inventive) | 52.8 | 23.97 | 66 | 1.10 |
| Example 2 (inventive), stored for one week at 60° C. | 52.8 | 27.01 | 63 | 1.20 |

[1]@ 5000 ppm; pH = 7 buffer, rt; 100 s$^{-1}$
[2]@ 1000 ppm; pH = 7 buffer

CONCLUSION

From table 1 it becomes obvious that the polymer of the inventive example shows similar properties and performance as the polymer of the comparative example. Unexpectedly, it is possible to produce a polymer, a copolymer of acrylamide and ammonium (meth-) acrylate, wherein the ammonium (meth-) acrylate is obtained in form of an aqueous ammonium (meth-) acrylate solution from the process of the present invention. From the MPFR value is become clear that the inventive polymer and the comparative polymer show similar properties. Both MPFR values are below 1.3 and with that in the acceptable range. Consequently, it is a surprise that with the process of the present invention for examples aqueous ammonium (meth-) acrylate solutions can be produced, which are suitable for further processing to polymers without a cleaning and/or drying step. Surprisingly, the resulting polymers of the present invention do not degrade during storage for one week at 60° C.

The invention claimed is:

1. A process for producing ammonium (meth-) acrylate, said process comprising the following steps:
   (a) adding the following components (i) to (iii) to a reactor to obtain a composition for bioconversion:
   (i) a biocatalyst capable of converting (meth-) acrylonitrile to ammonium (meth-) acrylate;
   (ii) (meth-) acrylonitrile;
   (iii) aqueous medium; and
   (b) performing a bioconversion on the composition obtained in step (a) in a reactor;
   wherein the reactor is a relocatable bioconversion unit, the unit comprising:
   a single walled reaction vessel, the vessel having;
      a volume from 10 m$^3$ to 150 m$^3$;
      means for mixing the composition of step (a); and
      means for controlling the temperature of the composition of step (a).

2. Process according to claim 1, wherein the (meth-) acrylonitrile concentration of the composition at the end of the bioconversion is below 10.0% (w/w) by weight of the (meth-) acrylonitrile in the aqueous medium.

3. Process according to claim 1, wherein the concentration of ammonium (meth-) acrylate at the end of the bioconversion is at least 10% (w/w) by weight of the ammonium (meth-) acrylate monomers in the aqueous medium.

4. Process according to claim 1, wherein the biocatalyst is an enzyme having nitrilase activity.

5. Process according to claim 1, wherein the biocatalyst having nitrilase activity is one selected from the group consisting of an isolated nitrilase, a recombinant construct, a recombinant vector comprising the recombinant construct, a recombinant microorganism comprising the recombinant construct, and a recombinant microorganism comprising the recombinant vector.

6. Process according to claim 1, wherein the biocatalyst is a recombinant microorganism selected from the group consisting of *Bacillus licheniformis*, *Bacillus pumilus*, *Bacillus subtilis*, *Escherichia coli*, *Saccharomyces cerevisiae*, *Rhodococcus rhodocrous*, and *Pichia pastoris*.

7. Process according to claim 1, wherein the relocatable bioconversion unit comprises a frame, a double-walled reaction vessel mounted into the frame having a volume from 10 m$^3$ to 150 m$^3$, and an external temperature control circuit comprising at least a pump and a temperature control unit, wherein the composition of step (a) is circulated by means of a pump from the reaction vessel into the temperature control unit and back into the reaction vessel, thereby simultaneously controlling the temperature and mixing the composition of step (a).

8. Process according to any of claim 1, wherein the relocatable bioconversion unit comprises a frame, a single walled reaction vessel mounted into the frame having a volume from 10 m$^3$ to 150 m$^3$, and an external temperature control circuit comprising at least a pump and a temperature control unit, wherein the composition of step (a) is circulated by means of a pump from the reaction vessel into the temperature control unit and back into the reaction vessel, thereby simultaneously controlling the temperature and mixing the composition of step (a).

9. Process according to claim 8, wherein the amount of the composition of step (a) cycled per hour through the temperature control circuit is from 100% to 1000% of the total volume of the composition of step (a) in the bioconversion unit.

* * * * *